United States Patent
Palmer et al.

(10) Patent No.: US 6,503,245 B2
(45) Date of Patent: Jan. 7, 2003

(54) METHOD OF PERFORMING PORT OFF-PUMP BEATING HEART CORONARY ARTERY BYPASS SURGERY

(75) Inventors: Matthew A. Palmer, Miami, FL (US); Javier E. Castañeda, Miami, FL (US); Jose Luis Francese, Springs, FL (US); Ralph de la Torre, Charlestown, MA (US)

(73) Assignee: Medcanica, Inc., Miami, FL (US)

( * ) Notice: Subject to any disclaimer, the term of this patent is extended or adjusted under 35 U.S.C. 154(b) by 143 days.

(21) Appl. No.: 09/733,498

(22) Filed: Dec. 8, 2000

(65) Prior Publication Data

US 2002/0042595 A1 Apr. 11, 2002

Related U.S. Application Data

(63) Continuation-in-part of application No. 09/686,696, filed on Oct. 11, 2000, and a continuation-in-part of application No. 09/686,530, filed on Oct. 11, 2000.

(51) Int. Cl.$^7$ .............................................. A61B 17/00
(52) U.S. Cl. ........................ 606/1; 604/513; 604/539; 604/164.04; 128/898
(58) Field of Search .......................... 128/898; 600/201, 600/208, 210, 215, 235; 606/108, 1; 604/513, 533, 539, 174, 164.04

(56) References Cited

U.S. PATENT DOCUMENTS

| | | | |
|---|---|---|---|
| 5,104,383 A | 4/1992 | Shichman | 604/167 |
| 5,147,316 A | 9/1992 | Castillenti | 604/164 |
| 5,176,648 A | 1/1993 | Holmes et al. | 604/164 |

(List continued on next page.)

FOREIGN PATENT DOCUMENTS

| | | |
|---|---|---|
| CA | 2216893 | 7/1997 |
| DE | 29707567 U1 | 7/1997 |
| EP | 0336 526 A1 | 10/1989 |
| EP | 0356410 A1 | 2/1990 |
| EP | 0630629 A1 | 12/1994 |
| EP | 0791330 A2 | 8/1997 |
| EP | 0820721 A1 | 1/1998 |
| FR | 1019217 | 1/1953 |
| WO | WO87/04081 | 7/1987 |
| WO | WO94/14383 | 7/1994 |

(List continued on next page.)

OTHER PUBLICATIONS

Pilling Surgical Instruments 1993 catalogue, p. 304, designs for Miscellaneous Heart Instruments.
Article entitled "Left Anterior Descending Coronary Artery Grafting via Left Anterior Small Thoracotomy without Cardiopulmonary Bypass" by Calafiore et al., in the 1996 Journal, The Society of Thoracic Surgeons, pp. 1658–1665.
Article entitled "Coronary Artery Bypass without Cardiopulmonary Bypass" by Pfister et al, in the 1992 Journal, The Society of Thoracic Surgeons, pp. 1085–1092.

(List continued on next page.)

*Primary Examiner*—Linda C. M. Dvorak
*Assistant Examiner*—Jocelyn Ram
(74) *Attorney, Agent, or Firm*—David P. Gordon; David S. Jacobson; Thomas A. Gallagher

(57) ABSTRACT

A method for performing through-port off-pump beating heart coronary artery bypass surgery is provided. A port device is positioned in the chest wall and directed as necessary. A heart stabilizer is coupled to the port, and operated to apply a compressive force against the heart wall surrounding a location the required bypass such that the location is substantially immobilized. An instrument stabilizer includes a cannula which is inserted through a hole in the chest cavity, and the distal tip of the cannula is located adjacent the surgical site. The instrument stabilizer dampens movement of a surgical instrument, e.g., a scalpel or needle holder, extended therethrough. Once the bypass procedure is complete, the instruments, heart stabilizer, instrument stabilizers, and port are removed from the body of the patient.

20 Claims, 42 Drawing Sheets

U.S. PATENT DOCUMENTS

| | | | |
|---|---|---|---|
| 5,364,367 A | 11/1994 | Banks et al. | 604/174 |
| 5,374,277 A | 12/1994 | Hassler | 606/207 |
| 5,375,588 A | 12/1994 | Yoon | 128/4 |
| 5,389,081 A | 2/1995 | Castro | 604/167 |
| 5,391,156 A * | 2/1995 | Hildwein et al. | 411/503 |
| 5,407,427 A | 4/1995 | Zhu et al. | 604/26 |
| 5,445,615 A | 8/1995 | Yoon | 604/96 |
| 5,447,515 A | 9/1995 | Robicsek | 606/158 |
| 5,452,733 A | 9/1995 | Sterman et al. | 128/898 |
| 5,472,429 A | 12/1995 | Yoon | 604/178 |
| 5,476,479 A | 12/1995 | Green et al. | 606/205 |
| 5,490,843 A | 2/1996 | Hildewein | 604/164 |
| 5,540,648 A | 7/1996 | Yoon | 600/114 |
| 5,545,179 A | 8/1996 | Williamson, IV | 606/213 |
| 5,571,072 A | 11/1996 | Kronner | 600/102 |
| 5,582,577 A | 12/1996 | Lund et al. | 600/204 |
| 5,613,937 A | 3/1997 | Garrison et al. | 600/201 |
| 5,637,097 A | 6/1997 | Yoon | 604/174 |
| 5,653,718 A | 8/1997 | Yoon | 606/148 |
| 5,685,857 A | 11/1997 | Negus | 604/170 |
| 5,688,247 A | 11/1997 | Haindl | 604/175 |
| 5,707,362 A | 1/1998 | Yoon | 604/164 |
| 5,713,869 A | 2/1998 | Morejon | 604/174 |
| 5,725,553 A | 3/1998 | Moenning | 606/213 |
| 5,735,290 A | 4/1998 | Sterman et al. | 128/898 |
| 5,749,892 A | 5/1998 | Vierra et al. | 600/204 |
| 5,782,813 A | 7/1998 | Yoon | 604/174 |
| 5,799,661 A | 9/1998 | Boyd et al. | 128/898 |
| 5,807,243 A * | 9/1998 | Vierra et al. | 128/898 |
| 5,817,062 A | 10/1998 | Flom | 604/174 |
| 5,820,555 A | 10/1998 | Watkins, III | 600/204 |
| 5,823,946 A | 10/1998 | Chin | 600/604 |
| 5,836,913 A | 11/1998 | Orth et al. | 604/107 |
| 5,865,730 A | 2/1999 | Fox et al. | 600/228 |
| 5,865,809 A | 2/1999 | Moenning et al. | 604/174 |
| 5,865,817 A | 2/1999 | Moenning et al. | 604/283 |
| 5,894,843 A | 4/1999 | Benetti et al. | 128/898 |
| 5,976,080 A | 11/1999 | Farascioni | 600/213 |
| 5,980,455 A | 11/1999 | Daniel et al. | 600/235 |
| 6,007,486 A * | 12/1999 | Hunt et al. | 600/205 |
| 6,015,378 A | 1/2000 | Borst et al. | 600/37 |
| 6,017,304 A | 1/2000 | Vierra et al. | 600/204 |
| 6,019,722 A | 2/2000 | Spence et al. | 600/210 |
| 6,027,476 A | 2/2000 | Sterman et al. | 604/966 |
| 6,033,362 A | 3/2000 | Cohn | 600/213 |
| 6,033,426 A | 3/2000 | Kaji | 606/213 |
| 6,036,641 A | 3/2000 | Taylor et al. | 600/231 |
| 6,039,725 A | 3/2000 | Moenning et al. | 606/1 |
| 6,045,536 A | 4/2000 | Meier et al. | 604/174 |
| 6,050,266 A * | 4/2000 | Benetti et al. | 128/898 |
| 6,056,689 A | 5/2000 | Lenox et al. | 600/217 |
| 6,056,766 A | 5/2000 | Thompson et al. | 606/185 |
| 6,063,021 A | 5/2000 | Hossain et al. | 600/37 |
| 6,110,187 A | 8/2000 | Donlon | 606/151 |
| 6,113,534 A | 9/2000 | Koros et al. | 600/213 |
| 6,132,370 A | 10/2000 | Furnish et al. | 600/235 |
| 6,139,492 A | 10/2000 | Vierra et al. | 600/204 |
| 6,193,652 B1 * | 2/2001 | Berky et al. | 600/201 |
| 6,398,726 B1 * | 6/2002 | Ramans et al. | 600/228 |

FOREIGN PATENT DOCUMENTS

| | | |
|---|---|---|
| WO | WO95/15715 | 6/1995 |
| WO | WO95/17127 | 6/1995 |
| WO | WO96/04854 | 2/1996 |
| WO | WO97/10753 | 3/1997 |
| WO | WO97/20524 | 6/1997 |
| WO | WO97/27807 | 8/1997 |
| WO | WO98/25549 | 6/1998 |
| WO | WO99/11201 | 3/1999 |

OTHER PUBLICATIONS

Article entitled "Snaring of the Target Vessel in Less Invasive Bypass Operations does not cause Endothelial Dysfunction", by Perrault et al., in the 1997 Journal, The Society of Thoracic Surgeons, pp. 751–755.

Article entitled "Triple Coronary Artery Revascularization on the Stabilized Beating Heart: Initial Experience", by Cartier et al., from the Department of Cardiovascular Surgery and the Dept. of Anesthesiology, Montreal Heart Institute, Sep. 19, 1997, pp. 283–288.

Article entitled "Direct Myocardial Revascularization by Saphenous Vein Graft" by Favaloro et al. in the Aug. 1970, vol. 10, Journal of The Society of Thoracic Surgeons, pp. 97–111.

Editorial entitled "Coronary Surgery without Cardiopulmonary bypass", in British Heart Journal, 1995; 73:pp. 203–205.

Article entitled "The Cardiac Rag– simple exposure of the heart" by Badellino et al., vol. 15, No. 2, 1988 in the Texas Heart Institute Journal, pp. 134–135.

Letter to the Editor in Archives of Surgery, vol. 115, No. 9, Sep. 1980, on "New Use for an Old Clamp", 4 pages.

J Cardiovasc Surgery, 30, 1989, pp. 996–997, Technical Comments article entitled "Internal mammary artery dissection: A three dimensional sternal retractor" by Roux et al.

Article entitled "Off–Bypass Coronary Grafting via Minithoracotomy using Mechanical Epicardial Stabilization", by Cremer et al., in the 1997 Journal, The Society of Thoracic Surgeons, pp. 579–583.

Article entitled "Single coronary bypass grafting– a comparison between minimally invasive "off pump" techniques and conventional procedures", by Bonattie et al., in the European Journal of Cardio–thoracic Surgery 17 (Suppl 1), 1998, pp. S7–S12.

Article entitled "Less Invasive Coronary Surgery: Consensus from the Oxford Meeting", by Westaby et al., in the 1996 Journal, The Society of Thoracic Surgeons, pp. 924–931.

Article entitled "Mini–Sternotomy for Coronary Artery Bypass Grafting", by Arom et al., in the 1996 Journal, The Society of Thoracic Surgeons, pp. 1271–1272.

Article entitled "Limited Access Myocardial Revascularization" by Cooley, in the Texas Heart Institute Journal, vol. 23, No. 2, 1996, pp. 81–84.

Letter to the Editor on Mini–Sternotomy for Coronary Artery Bypass Grafting by A. Cohen et al., 1996, pp. 1884–1885, Journal, The Society of Thoracic Surgeons.

Article entitled "Fabric Heart Retractor for Coronary Artery Bypass Operations" by Kazama et al. in the 1993 Journal, The Society of Thoracic Surgeons, pp. 1582–1583.

Article entitled "Minimally Invasive Coronary Artery Bypass Grafting" by Calafiore et al. in the 1996 Journal, The Society of Thoracic Surgeons, pp. 1545–1548.

Article entitled "Improved Visualization of the Internal Mammary Artery with a New Retractor System" by Pittman et al. in the 1989 Journal, The Society of Thoracic Surgeons, pp. 869–870.

Article entitled "A Modified Sternal Retractor" by Ancalmo et al. from the Dept. of Surgery, Alton Ochsner Medical Foundation and Ochsner Clinic, New Orleans, LA, Aug. 8, 1975., p. 174.

Article entitled "A Versatile Retractor For Use In Harvesting The Internal Mammary Artery And Performing Standard Cardiac Operations" by Phillips et al., in the J Thoracic Cardiovasc Surg 1989, vol. 97, pp. 633–635.

Article entitled "Surgical Management of Diseased Intracavitary Coronary Arteries" by Ochsner et al. in The Annals of Thoracic Surgery, vol. 38, No. 4, Oct. 1984, pp. 356–362.

Article entitled "Technique of internal mammary–coronary artery anastomosis" by Green, in the Journal of Thoracic Surgery, vol. 78, 1979, pp. 455–459.

Article entitled "Graduated probes for coronary bypass surgery" by Parsonner et al., in the Journal of Thoracic and Cardiovascular Surgery, vol. 68, No. 3, Sep. 1974, pp. 424–427.

Article entitled "A Modified Sternal Retractor for Exposure of the Internal Mammary Artery" by McKeown et al., in the Society of Thoracic Surgeons, 1980, p. 619.

Article entitled "A New Concept in Sternal Retraction: Application for Internal Mammary Artery Dissection and Valve Replacement Surgery" by Chaux et al., in the Annals of Thoracic Surgery, vol. 42, Oct. 1986, pp. 473–474.

Article entitled "Cardiac Retractor for Coronary Bypass Operations" by Rousou et al., in The Society of Thoracic Surgeons, 1991, pp. 877–878.

Article entitled A New Retractor to Aid in Coronary Artery Surgery: by DelRossi et al., in the in the Annals of Thoracic Surgery, vol. 36, No. 1, Jul. 1983.

Article entitled "New Helper Instrument in Cardiac Surgery" by Roux et al., in the Society of Thoracic Surgeons, 1989, pp. 505–596.

Article entitled "Aortic Spoon–Jaw Clamp for Aorto–Saphenous Vein Anastomosis" by Robicsek, in the Journal of Card Surg, 1995; vol. 10, pp. 583–585.

Article entitled "Techniques of dissecting the internal mammary after using the Moussalli bar" by Hasan et al. , the European J Cardio–thorac Surg, 1990, vol. 4, pp. 571–572.

Article entitled "Self–Retaining Epicardial Retractor For Aortocoronary Bypass Surgery" by Parsonnet et al., in the Journal of Thoracic and Cardiovascular Surgery, 1979, pp. 629–630.

Article entitled Coronary Artery bypass Grafting without Cardiopulomnary Bypass and Without Interruption of Native Coronary Flow Using a Novel Anastomosis Site Restraining Device ("Octopus"), by Borst et al., JACC, vol. 27, No. 6, May 1996, pp. 1356–1364.

Article entitled "A New Internal Mammary Artery Retractor" by Bugge, in the Thorac.cardiovasc. Surgeon, vol. 38, 1990, pp. 316–317.

Article entitled "A Simple, Inexpensive Method of Heart Retraction During Coronary Artery Bypass Surgery" by Angelini, in the Ann Thorac Surg, vol. 46, pp. 246–247, Aug. 1988.

Article entitled A New Device for Exposing the Circumflex Coronary Artery: by Matsuura et al., in the Society of Thoracic Surgeons, 1995, pp. 1249–1250.

Article entitled "Application of a Special vasal devaricator during coronary surgery" by Vigano, in the Minerva Cardioangiologica, Jul. 1975, pp. 370–371.

Translation of "Heart Retractor for Use in Anastomosis in Coronary Artery By–pass Surgery" by Eguchi, from the Japanese Journal of Thoracic Surgery, vol. 40, No. 1, 1987, 4 pages.

Japanese article (title tranlated) on "A Special Retractor for Stabilizing the Heart During Circumflex Coronary Grafting" by Eguchi, 1987, 2 pages.

Article entitled "Revascularization of the Circumflex Coronary Artery—A New Instrument and a Technical Method– " by Murata, in the Japanese Journal of Thoracic Surgery, 1989, vol. 42, No. 2, 6 pages.

* cited by examiner

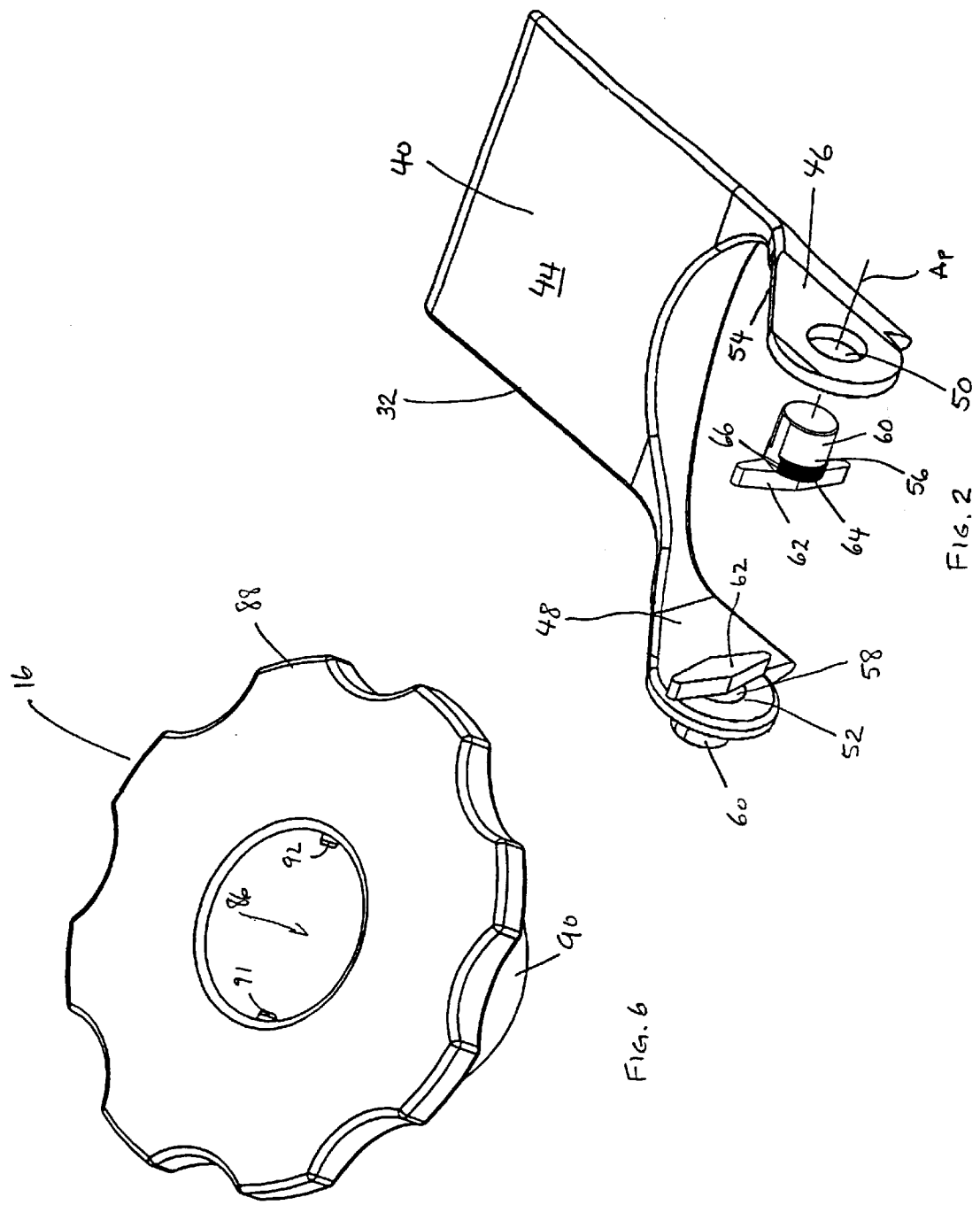

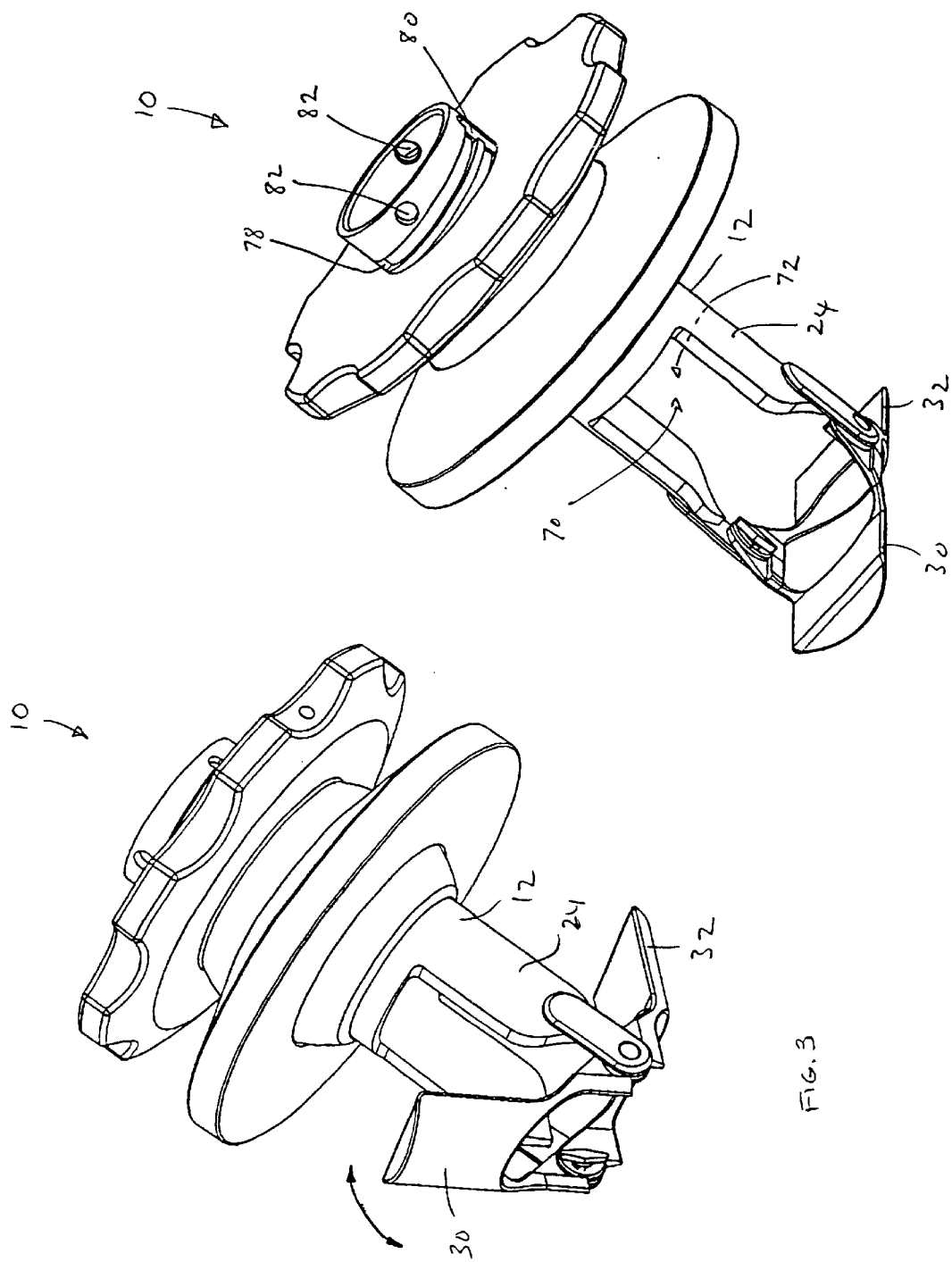

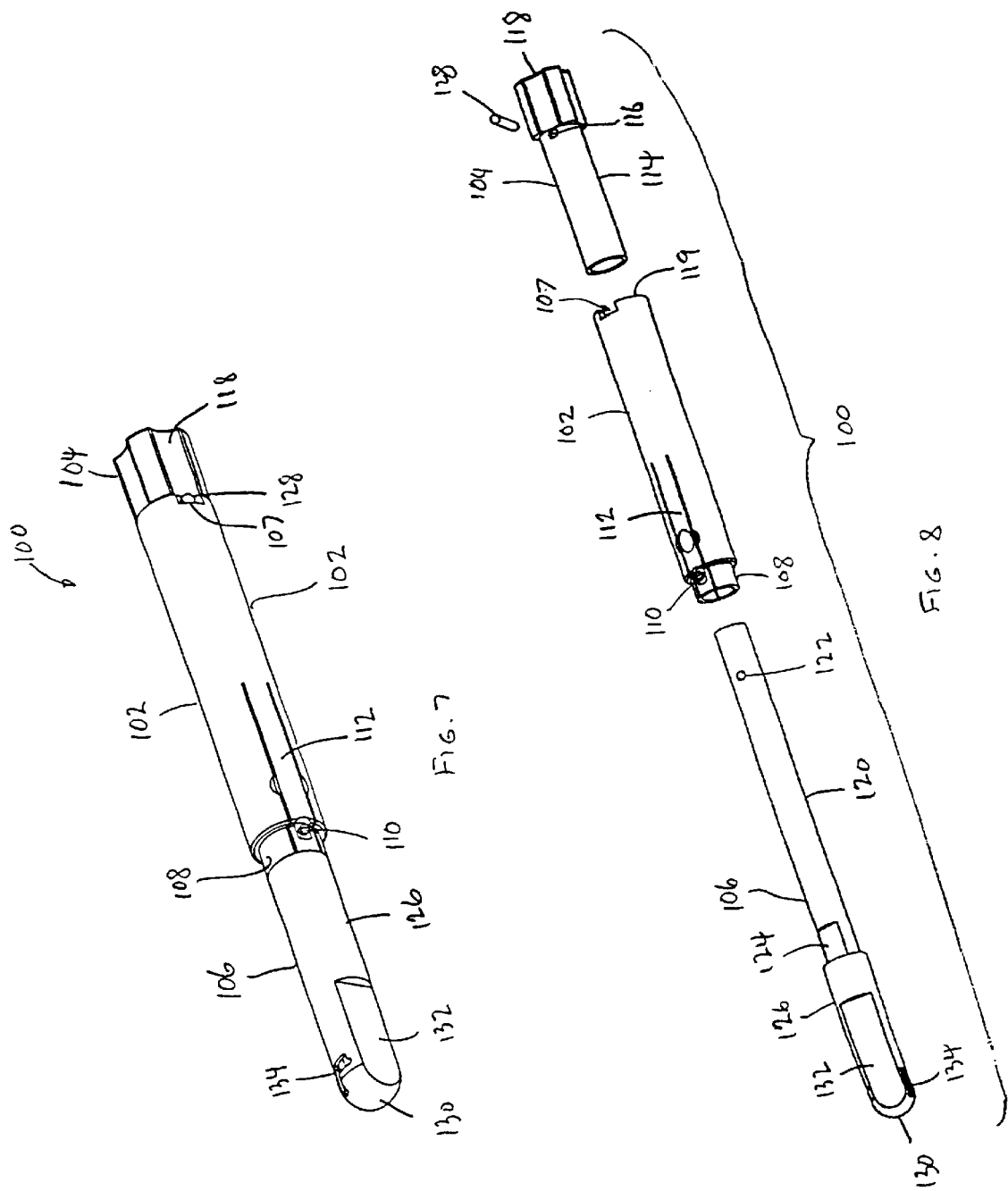

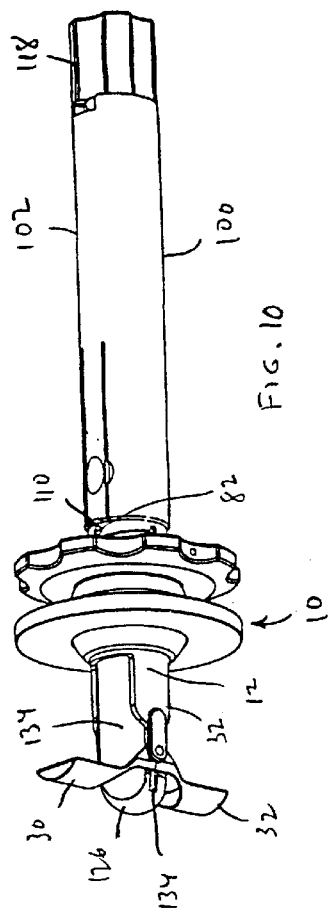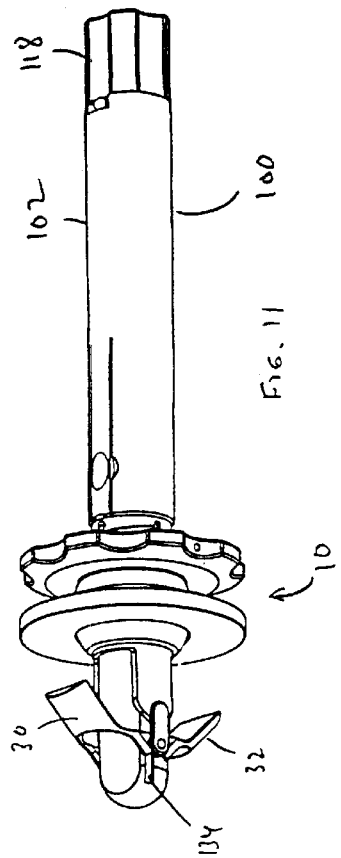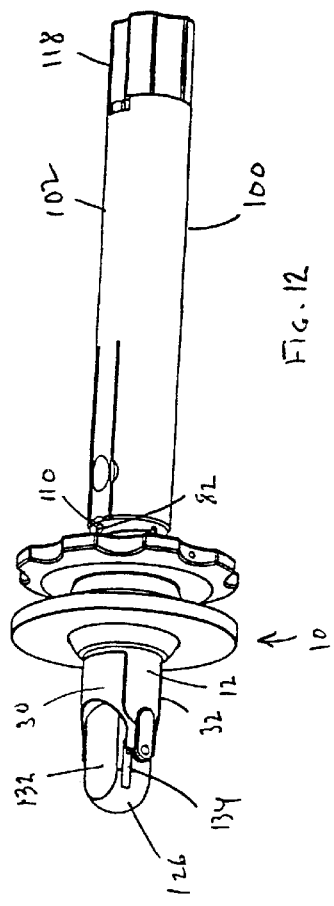

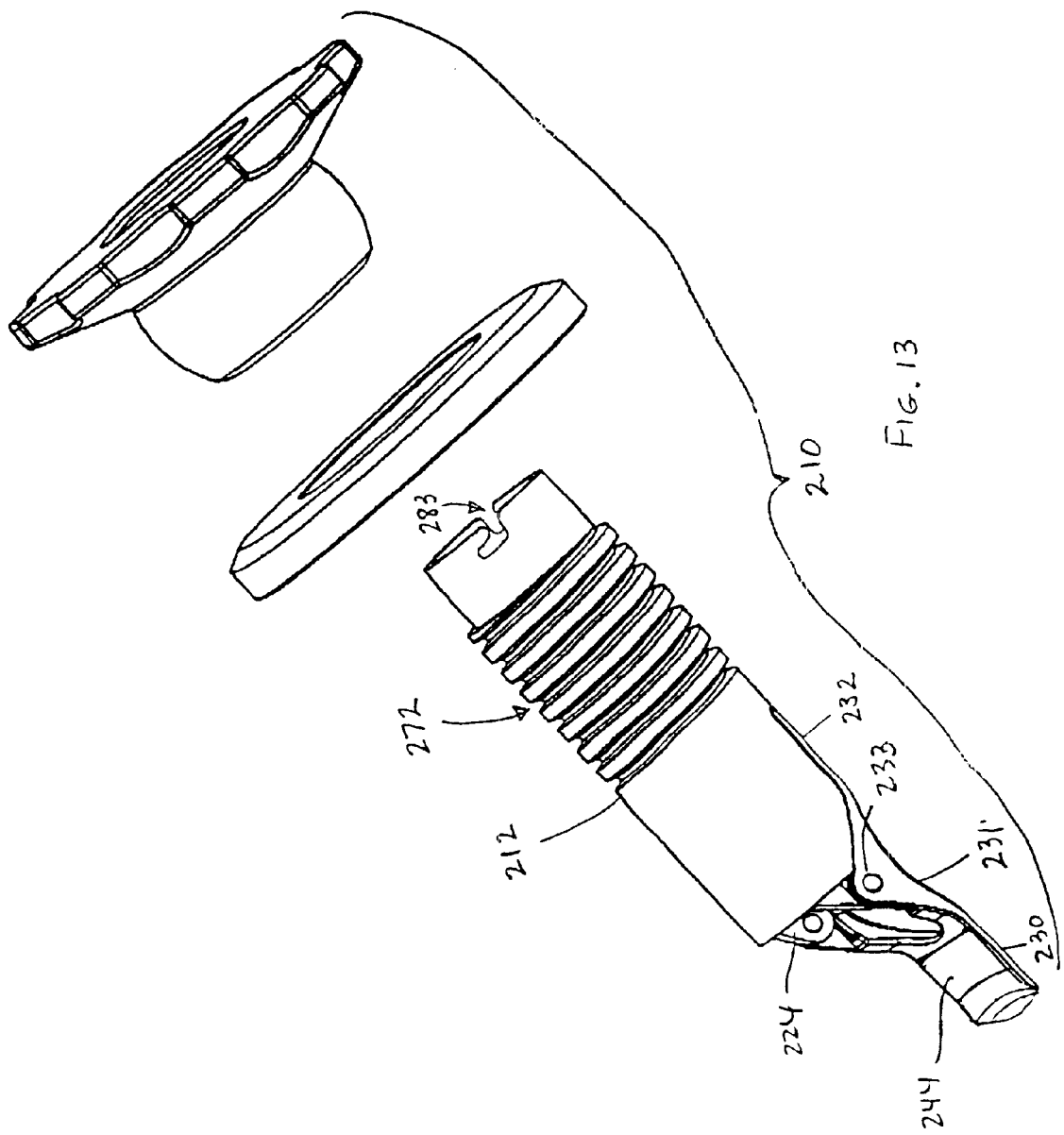

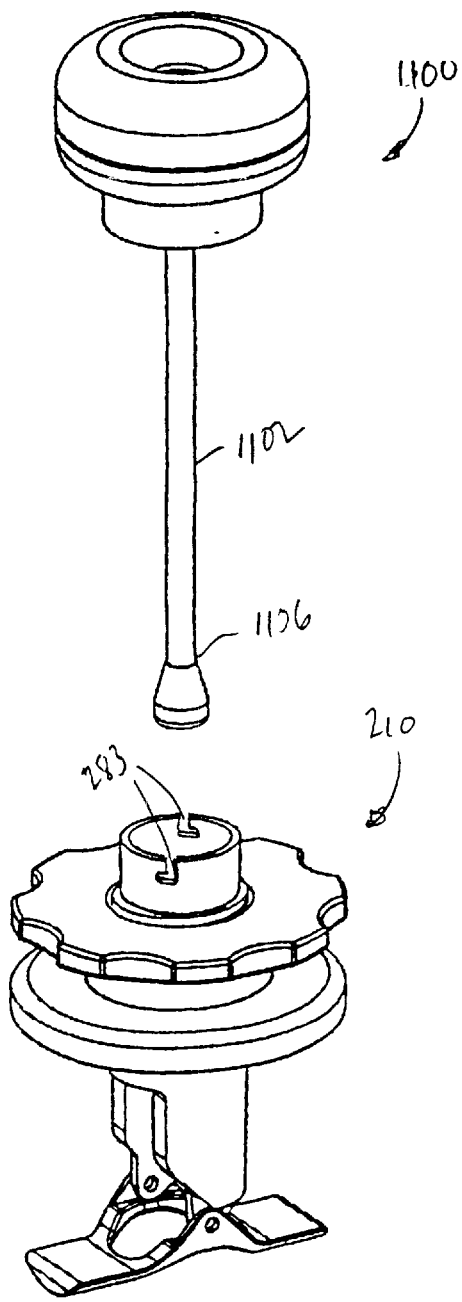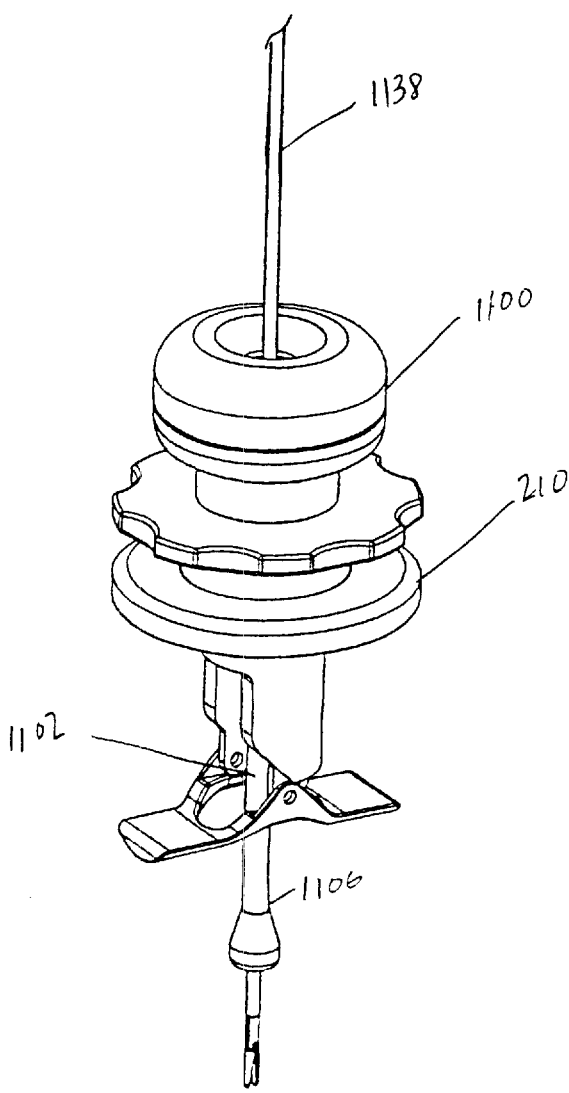
FIG. 38
FIG. 39

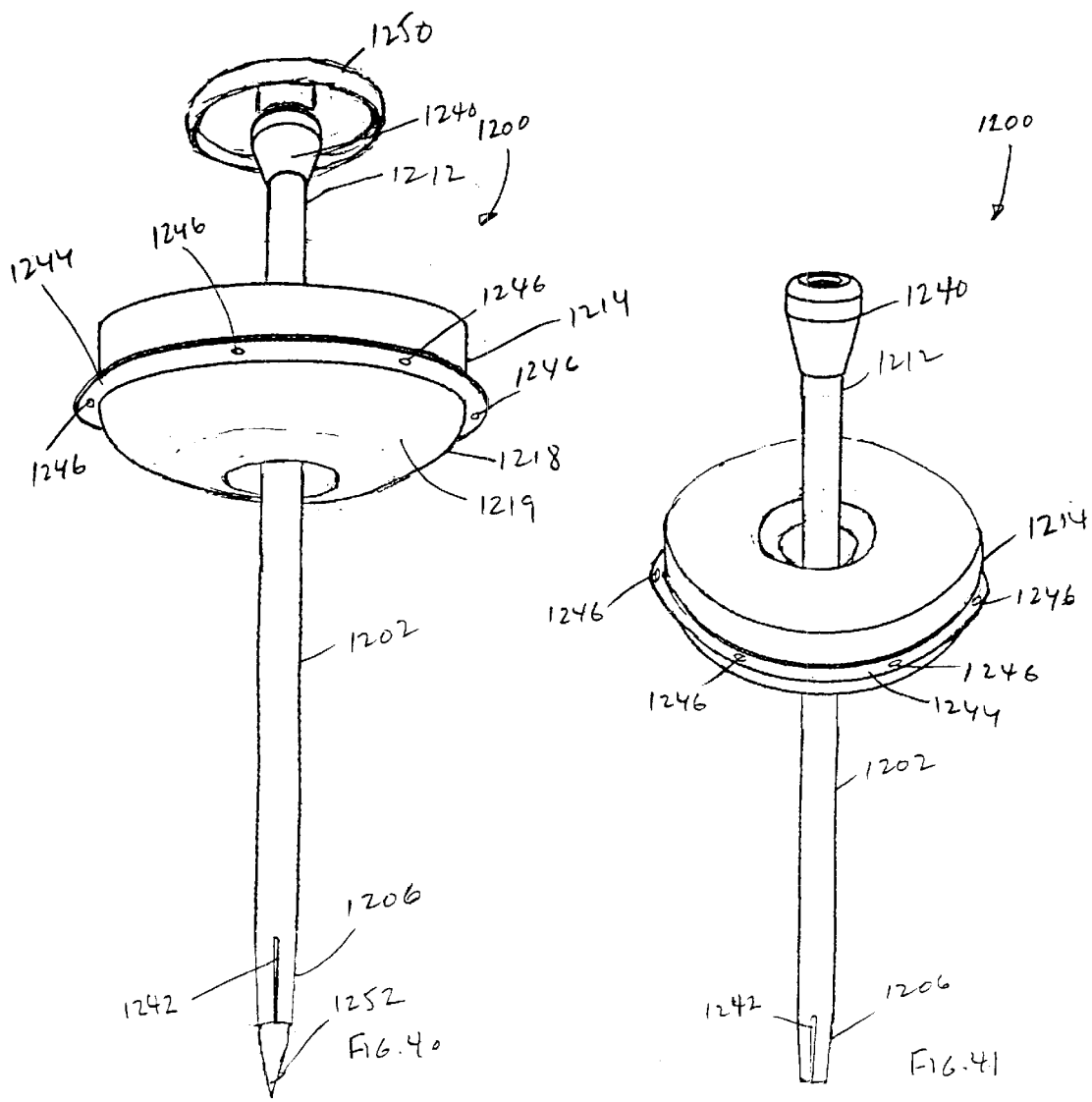

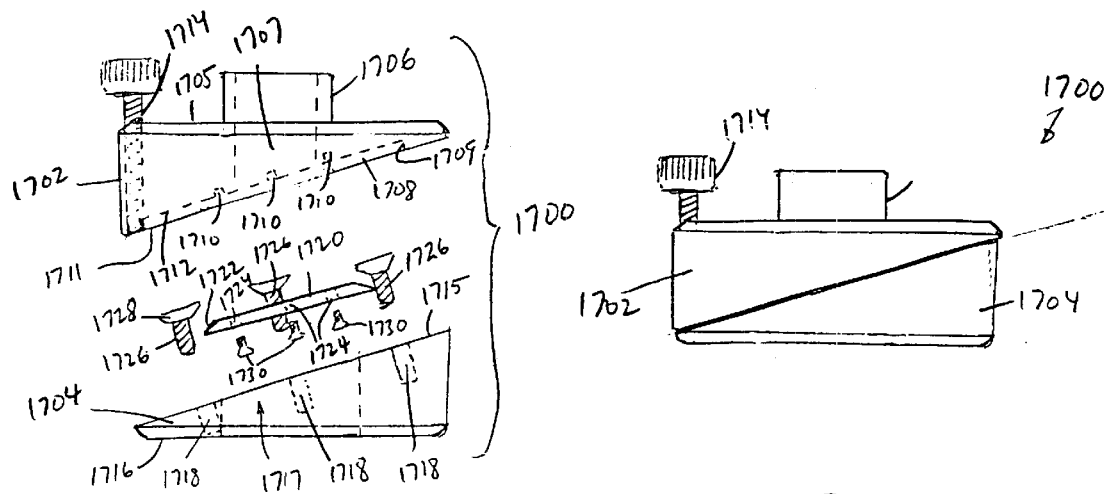
FIG. 50
FIG. 49
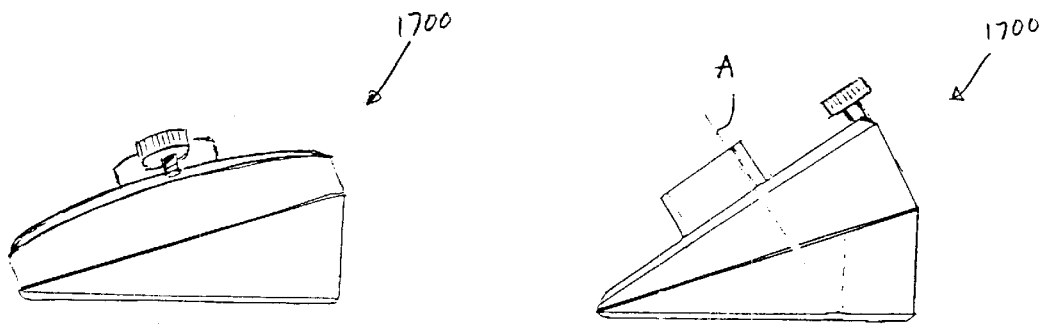
FIG. 51
FIG. 52

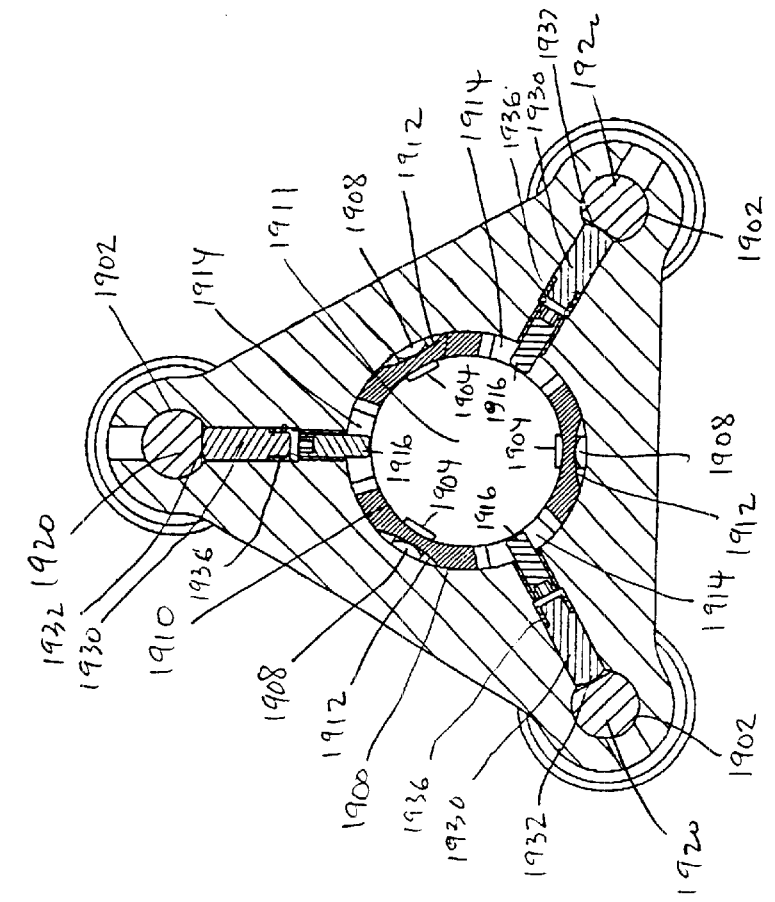
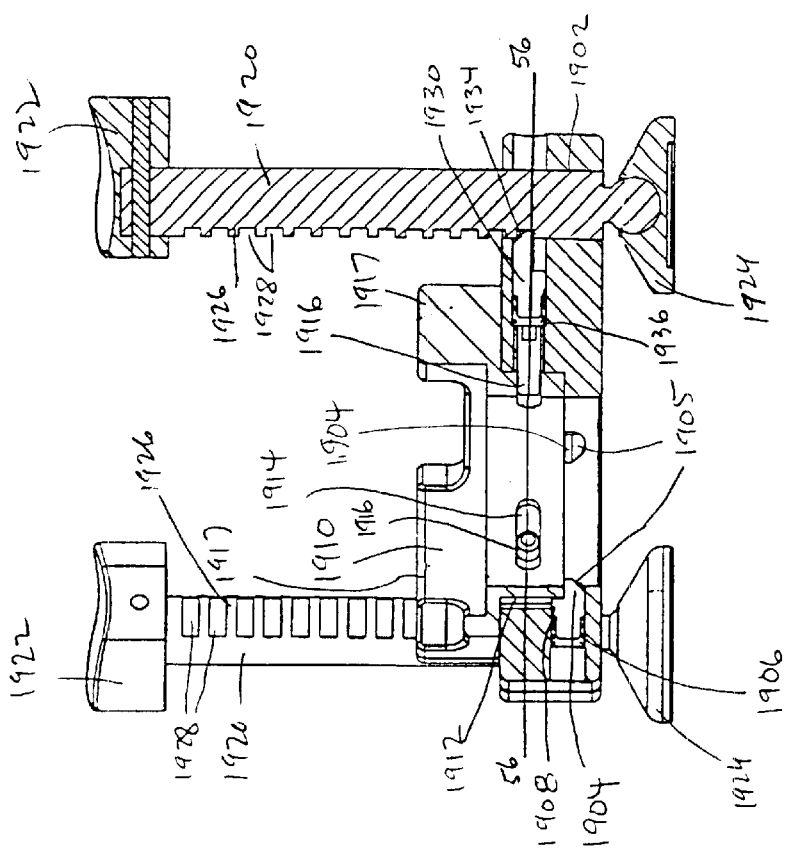

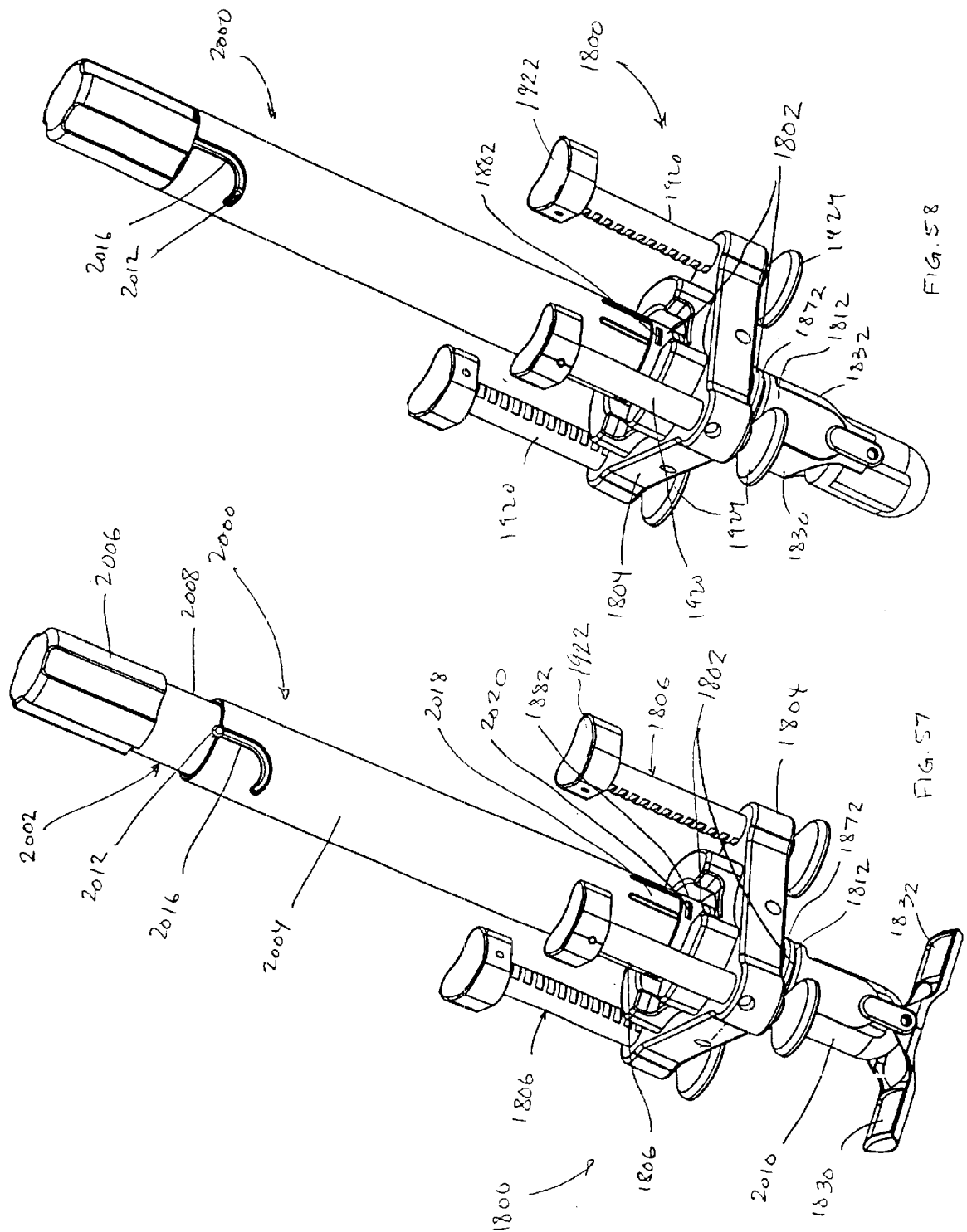

METHOD OF PERFORMING PORT OFF-PUMP BEATING HEART CORONARY ARTERY BYPASS SURGERY

This application is a continuation-in-part of U.S. Ser. No. 09/686,696, filed Oct. 11, 2000 and entitled "Port Device for Port Off-Pump Beating Heart Coronary Artery Bypass Surgery System", and U.S. Ser. No. 09/686,530, filed Oct. 11, 2000 and entitled "Port Off-Pump Beating Heart Coronary Artery Bypass Heart Stabilization System", each which is hereby incorporated by reference herein in its entirety.

BACKGROUND OF THE INVENTION

1. Field of the Invention

This invention relates broadly to surgical methods. More particularly, this invention relates to a method for performing coronary artery bypass surgery.

2. State of the Art

Substantially all coronary artery bypass (CAB) procedures are performed via an open chest method. In the procedure, the chest is opened through an, incision in the middle of the chest, called a sternotomy, and the ribs are retracted and held stably open with a retractor. This provides a sufficient amount of access to the heart. The heart is then arrested and the blood flow is rerouted through a heart-lung machine. The bypass procedure is then performed, and once complete, the heart is then restarted and blood is permitted to flow through the "bypass". While this procedure is the norm, it is far from desirable. First, arresting the heart is a dangerous procedure and can lead to serious complications and even death. Second, the procedure requires a sternotomy, which is painful and traumatic. Because of this incision the recovery time is relatively long and the patient is left with a permanent large scar.

More recently, some surgeons have performed coronary artery bypass surgery on a beating heart. The chest is opened via a sternotomy and retracted. Using a device called a heart stabilizer, the surgical site on the heart is essentially immobilized for suturing. The heart stabilizer is typically anchored to the retractors which are in turn anchored to the walls of the chest at the site of the incision. Direct access to the surgical site as well as immobilization of the surgical site are key to the surgery. These factors allow the surgeon to perform a suture or other operation with precision. While the methodology is effective and eliminates the potential complications of arresting the heart, the drawbacks associated with the sternotomy remain.

It has recently been proposed by others to perform a closed chest bypass procedure on the beating heart. However, the proposal has not been followed by any concrete directions on how to satisfactorily perform the procedure. In addition, the inventors of the present application have recognized that the closed chest procedure has a number of hurdles to overcome. First, it is necessary to stabilize the heart such that the location requiring the bypass does not significantly move during the procedure. Second, while open chest procedure are accompanied by a retractor and instrument supporting framework, in a closed chest procedure, there is no such framework for holding the instruments required for the procedure. In addition, there is no suitable stable port device adapted to securely support instruments passing therethrough. Third, when performing any surgery through a port, the instruments used to work at the surgical site are relatively long compared to open chest instruments. The distance from the surgeons's hand to the tip of the instrument where the work is being performed can be many times greater than in conventional surgery. This increase in length amplifies normal hand tremor and any errors in motion.

SUMMARY OF THE INVENTION

It is therefore an object of the invention to provide a less traumatic instrument access to the surgical site.

It is another object of the invention to provide a port device which is easy to insert into the body.

It is a further object of the invention to provide a port device with a high degree of stability.

It is an additional object of the invention to provide a heart stabilizer which can be inserted through the port device and which is adapted to stabilize a portion of a beating heart such that coronary artery bypass surgery can be performed on the portion of the heart.

It is also an additional object of the invention to provide a heart stabilizer which can be manipulated via a proximal handle external of the port device.

It is still another object of the invention to provide an instrument stabilization system which minimizes unwanted motion of the tips of instrument performing the procedure.

It is still a further object of the invention to provide an instrument stabilization system which can be coupled to the port device.

It is yet another object of the invention to provide a system of components which cohesively operates together to facilitate port off-pump coronary artery bypass surgery on a beating heart.

It is yet a further object of the invention to provide a method of performing port off-pump coronary artery bypass surgery on a beating heart.

In accord with these objects, which will be discussed in detail below, a system for performing port off-pump beating heart coronary artery bypass surgery is provided. The system includes three primary subsystems: a port device, a heart stabilizer, and an instrument stabilizer.

The port device is insertable between the ribs of the patient and functions as an entry way for each instrument necessary for the procedure, e.g., optics, graspers, needle holders, suction/irrigation tubes, stabilizers. According to a preferred aspect of the invention, the port device includes a tubular body having proximal and distal portions and intended to be inserted through a pair of ribs in a chest wall of a patient. The proximal portion of the tubular body includes a plurality of thread grooves extending at least partially about a circumference of the body as well as a means to permit the heart stabilizer, the instrument stabilizer, or another device to be releasably secured to the port. The distal portion of the tubular body is coupled to a swivel adapted to be moved between a first orientation in which the swivel extends in substantially a same direction as the body, and a second orientation at an angle relative to, and preferably substantially perpendicular to, the first orientation.

According to certain embodiments of the port device, a washer is positioned on the body between the swivel and the proximal portion of the body, and a locknut is threadably engaged in the thread grooves. When the tubular body is inserted between two ribs in the chest wall of the patient, the swivel is then opened into the second orientation and the washer is moved along the body to position the chest wall between the swivel and the washer. The locknut is then tightened about the body to clamp the washer against the chest wall and stably secure the tubular body within the chest wall.

According to other embodiments of the port device, a platform movable along the length of the port body includes adjustable legs and feet. The legs are adjusted such that the feet contact the chest wall and clamp the chest wall between the feet and the swivel. In addition, the legs may be adjusted to provide the body in a desired angle relative to the chest wall. According to preferred aspects of these embodiments of the port device, the platform may be ratcheted relative to the port body and the feet may be ratcheted relative to the platform to permit rapid adjustment of the port relative to the patient. In addition, preferably three legs are provided to aid in stability of the port on the body of the patient.

According to various aspects of the several embodiments of the port, the port may include a thread system adapted to permit quick locking of the locknut against the washer or the platform along the body, one or two swivels, and/or a ball joint permitting angular orientation of the port to permit the port to be directed toward a desired location such as the surgical site. In addition, the swivel or swivels may be spring biased to move from the first orientation to the second orientation, or an introducer device may be provided to mechanically move the swivel or swivels between the first and second orientations.

The heart stabilizer preferably includes a shaft and two jointed arms coupled to a distal end of the shaft. At the end of each arm is a rotatable foot adapted to be angled relative to the heart wall contour and apply pressure against the wall of the heart to effectively eliminate motion of the heart wall between the feet. The stabilizer is adapted to provide a stabilized area sufficiently large to allow an accurate anastomosis to be performed. According to preferred aspects of the invention, the stabilizer is particularly adapted to be collapsible (foldable) to be inserted through the port device and locked longitudinally relative thereto. The stabilizer is also preferably adapted to be automatically deployed into its final configuration by release of a lock actuated at a proximal portion of the stabilizer extending outside the port. In addition, the stabilizer is adapted to automatically fold when being pulled back through the port.

According to various embodiments of the heart stabilizer, the feet of the stabilizer may be further adapted to facilitate immobilization of the heart wall between the feet. In addition to compressive forces, the feet may apply suction, chemical agents, electrical current, or thermal cooling to enhance the heart wall immobilization.

According to another aspect of the invention, the instrument stabilizer is adapted to minimize unwanted motion at the distal end of a surgical instrument extending through the instrument stabilizer by applying a biasing force to the tip of the instrument. The instrument stabilizer may be coupled to a port or may be coupled directly to a patient, e.g., with sutures. According to a preferred embodiment, the instrument stabilizer preferably includes a cannula (tubular member) through which an instrument can extend, and a preferably distal contact element, e.g., an O-ring or a tapered diameter of the cannula, adapted to be in a close fit about the instrument and which provides proximal and distal stabilization. The instrument stabilizer also includes a proximal housing that includes a mechanism which applies a stabilizing force to the tubular member for movements transverse to the axis of the cannula. The mechanism which applies the force may be, by way of example, one or more of elastic bands, springs, struts, etc. When the surgical instrument is extended through the cannula and contacts the contact element, movement of the cannula and consequently the surgical instrument is damped by the stabilization force on the cannula. According to another embodiment, a mechanism which applies a stabilization force may be attached to a shaft of another instrument, e.g., the shaft of the heart stabilizer. According to yet another embodiment, the cannula is provided with a valve to permit the instrument stabilizer to be used for surgical procedures requiring insufflation of the body cavity in which the instrument stabilizer is inserted.

A stabilizer swivel may be used with an instrument stabilizer to angularly direct the cannula of the instrument stabilizer relative to the body of the patient. The stabilizer swivel includes upper and lower wedges rotatably coupled to each. Each wedge includes an opening through which the cannula may be extended. Relative rotational configurations of the wedges operate to orient the opening of the upper wedge relative to the lower wedge and the surface on which the lower wedge is seated.

The above-described components together define a surgical system for performing port off-pump beating heart coronary artery bypass surgery. According to a preferred method which utilizes the system, a port device is stably positioned, e.g. clamped, in the chest wall and directed as necessary for operation on the heart wall. A heart stabilizer is coupled to the port, and operated to apply a compressive force against the heart wall surrounding a location of the required bypass such that the location is substantially immobilized. An instrument stabilizer is inserted through a puncture hole in the chest cavity, and the distal tip of the cannula of the stabilizer is located adjacent to the surgical site. A first surgical instrument, e.g., a scalpel or needle holder, is passed through the cannula and operated to perform at least a portion of the procedure. If other surgical instruments are required, the first instrument may be removed and other instruments may be extended therethrough. Alternatively, an instrument stabilizer may be provided for each instrument. Once the bypass procedure is complete, the instruments and instrument stabilizers are removed from the locus of the surgery, and the heart stabilizer is also removed through its port. Then, the clamping forces on the port is loosened and the port is withdrawn from the chest wall. Finally, the incision and puncture holes in which the port and instrument stabilizer were located are closed. This method eliminates the need for many open heart procedures, as well as the need to stop the heart.

Additional objects and advantages of the invention will become apparent to those skilled in the art upon reference to the detailed description taken in conjunction with the provided figures.

BRIEF DESCRIPTION OF THE DRAWINGS

FIG. 2 is a partially disassembled top perspective view of a swivel and pivot axles according to the first embodiment of a port device according to the invention;

FIG. 3 is a bottom perspective view of the first embodiment of the port device according to the invention, shown with the swivels in a partly open configuration;

FIG. 4 is a top perspective view of the first embodiment of the port device according to the invention, shown with the swivels in an open configuration;

FIG. 6 is a top perspective view of a locking nut according to a first embodiment of a port device according to the invention;

FIG. 7 is a front perspective view of an introducer according to the invention;

FIG. 8 is an exploded perspective view of the introducer of FIG. 7;

FIG. 10 is a side perspective view of introducer coupled to the port device according to the invention, with the swivels shown in an open configuration;

FIG. 11 is a view similar to FIG. 10 with the swivels shown in a partly closed configuration;

FIG. 12 is a view similar to FIG. 10 with the swivels shown in a closed configuration;

FIG. 13 is an exploded side perspective view of a second embodiment of a port device according to the invention, with the swivel shown in a closed configuration;

FIG. 38 is an exploded perspective view of the first embodiment of the instrument stabilizer aligned with a port device according to the invention;

FIG. 39 is a perspective view of the first embodiment of the instrument stabilizer coupled to a port device, and a surgical instrument extending through the instrument stabilizer and port device;

FIG. 40 is a lower perspective view of a second embodiment of the instrument stabilizer of the invention, shown in with a trocar extending within the stabilizer;

FIG. 41 is an upper perspective view of the second embodiment of the instrument stabilizer of the invention;

FIG. 49 is a side view of a stabilizer swivel according to the invention and in a normal direction;

FIG. 50 is an exploded view of the stabilizer swivel according to the invention;

FIG. 51 is a side view of the stabilizer swivel in a first angular orientation;

FIG. 52 is a side view of the stabilizer swivel in a second angular orientation;

FIG. 55 is a longitudinal section view of the fifth embodiment of the port device, shown without the port tube;

FIG. 56 is a transverse section across line 56—56 in FIG. 55 of the fifth embodiment of the port device, shown without the port tube;

FIG. 57 is a perspective view of the fifth embodiment of the port device, shown with an introducer inserted therein for movement of the port swivels, the introducer positioned such that the swivels are in an open position; and FIG. 58 is a perspective view of the fifth embodiment of the port device, shown with an introducer inserted therein for movement of the port swivels, the introducer positioned such that the swivels are in a closed position.

DETAILED DESCRIPTION OF THE PREFERRED EMBODIMENTS

According to the invention, a system is provided for performing port off-pump beating heart coronary artery bypass surgery. The system includes a port device and a heart stabilizer.

Figure 1:
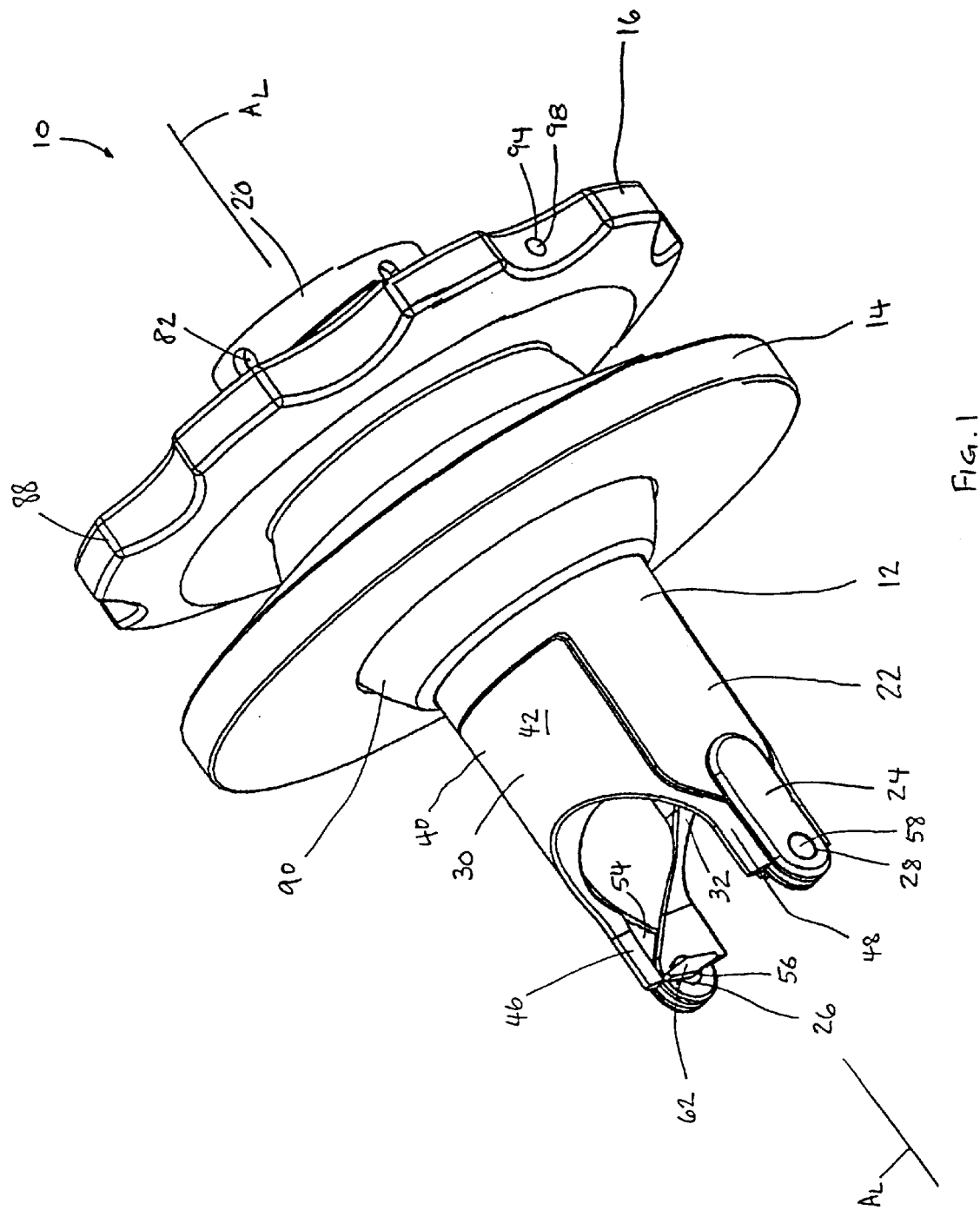
FIG. 1 is a bottom perspective view of a first embodiment of a port device according to the invention, shown with the swivels in a closed configuration.

Turning now to FIG. 1, a first embodiment of the port device 10 includes a tubular body 12, a washer 14 slidably mounted on the tubular body and a locknut 16 threadably coupled to the body 12 proximal of the washer 14. The tubular body 12 includes a proximal portion 20 and a distal portion 22. The distal portion 22 includes a clevis 24 defining two coaxial pivot bores 26, 28, and a pair of clamping swivels 30, 32 are rotatably coupled to the clevis 24 at the pivot bores 26, 28.

Referring to FIGS. 1 and 2 and with reference to swivel 32, each swivel includes a wing portion 40 with a preferably curved outer surface 42 and a preferably substantially planar inner contact surface 44, and two arms 46, 48 each including an axle bore 50, 52. One arm 46 of each swivel includes an inner recess 54 adapted to permit interleaving of the swivels about the clevis 24. Each arm 46, 48 of the swivel is coupled to the tubular body 12 with an axle member 56, 58 which extends through a respective axle bore 50, 52 and pivot bore 26, 28, and defines a pivot axis $A_P$. With reference to axle member 56, each axle member includes a relatively cylindrical first portion 60, an elongate trapezoidal-shaped lever 62, and an interference portion 64 between the first portion and lever portion. The interference portion 64 is slightly larger in diameter than the first portion 62 and includes knurls 66 or other gripping structure. The interference portion 64 of axle member 56 engages arm 46 about a respective axle bore, and the first portion 60 extends into the clevis bore 26, in which it is freely rotatable, while the interference portion 64 of axle member 58 engages arm 48 about a respective axle bore. As such, each axle member 56, 58 is fixedly attached to only one of the swivels and the swivel pivots about it. Then, as each swivels rotates about the clevis, a respective lever is also rotated and, similarly, rotation of the individual levers results in independent rotation of the swivels. The swivels 30, 32 are rotatable from a closed orientation (FIG. 1) in which the swivels extend substantially parallel to the body 12 through intermediate orientations (e.g., FIG. 3), and into a open orientation in which the swivels 30, 32 extend preferably perpendicular to the first orientation (FIG. 4). When in the first orientation, the swivels 30, 32 preferably complete the openings 72, 74 (FIG. 4) defined by the clevis 24, and the curvature of the outer surfaces 42 of the swivels provide the outer surface of the distal portion 22 with a substantially smooth surface. In addition, in the first orientation, the levers 62 are preferably oriented transverse the longitudinal axis AL of the body 12.

Figure 5:
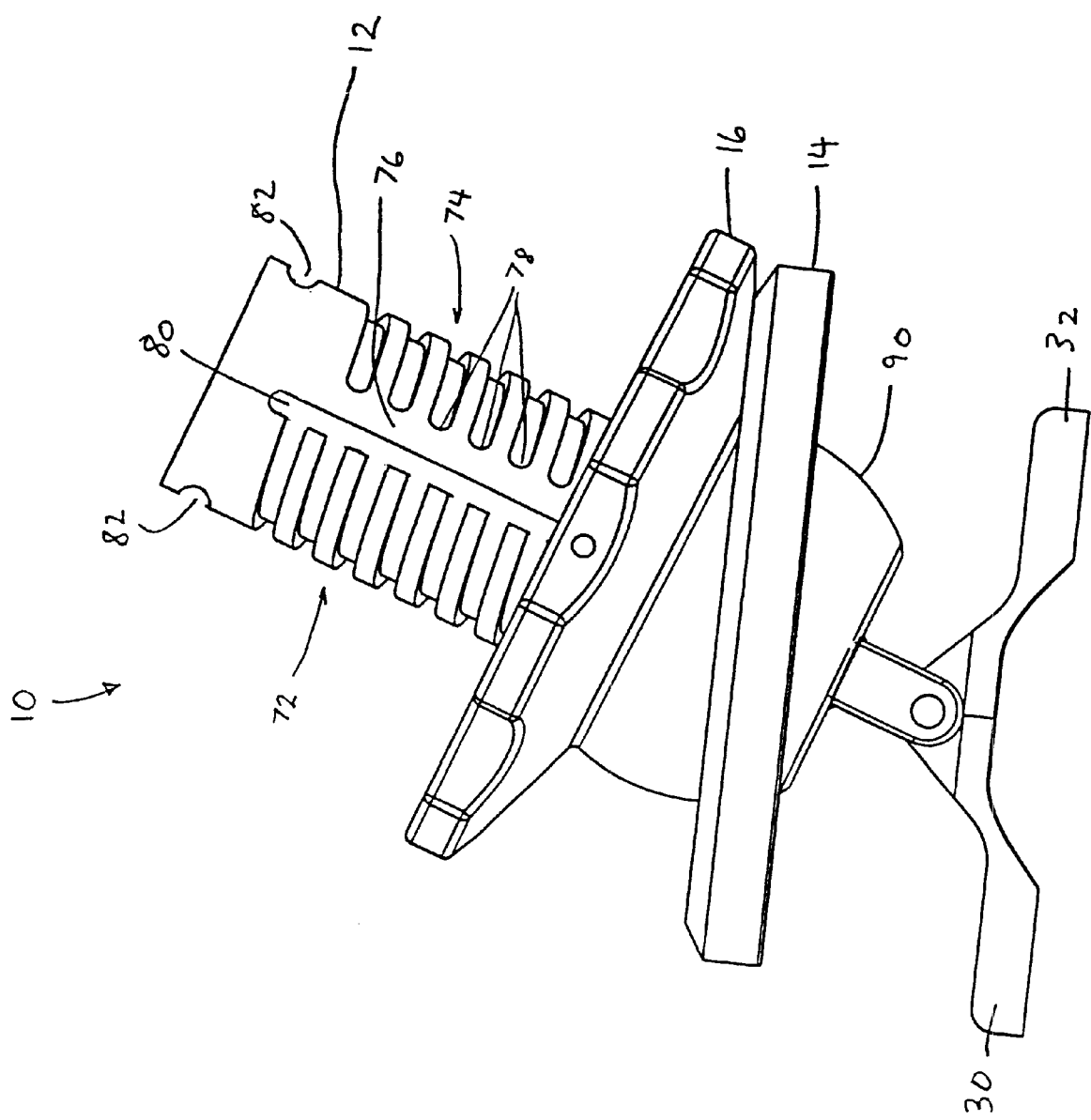
FIG. 5 is a side elevation view of the first embodiment of the port device according to the invention, shown with the swivels in an open configuration, and the port body angled relative to the washer.

Referring to FIG. 5, the proximal portion 20 of the tubular body 12 includes first and second sets of interrupted helical threads (grooves) 72, 74 extending along diametrically opposite sides of the body. The interruption 76 in the threads creates stops 78 after substantially 180° of rotation. A longitudinal groove 80 connects each set of threads 72, 74 together. The locknut 16, as described hereinafter, travels in the longitudinal grooves 80 and the threads 72, 74.

Referring now to FIGS. 1, 4 and 5, the proximal end 20 of the body 12 includes a coupling structure, e.g., the holes 82 of a ball latch, for removably coupling thereto the heart stabilizer the hereinafter described port introducer, or other device, as described in detail below.

The washer 14 is preferably disc-shaped and has a central opening 84 permitting the washer to fit about the tubular body 12 and provides an external clamping structure which operates in conjunction with the swivels 30, 32 to clamp human tissue therebetween, as described further below.

Referring to FIGS. 1 and 6, the locknut 16 includes a central opening 86, a handle portion 88, and a ball portion 90. Two nubs 91, 92 radially extend into the central opening and are sized to ride within the threads 72, 72, 74 and longitudinal grooves 80 on the proximal portion of the tubular body 12 (FIG. 5). As such, when each nub 91, 92 is positioned within a respective longitudinal groove 80, the locknut 16 may be moved quickly over the port body 12 and then rotated to thread the nubs 91, 92 into the threads 72, 74 to secure the locknut 16 at a desired location 10 over the body 12. One preferred manner of forming the nubs 91, 92 includes providing two diametrically opposite radial holes 94 in the handle portion 86 and inserting peg 98 into each radial hole such that the pegs extend into the central opening 86 to form the nubs. The ball portion 90 is a truncated sphere in shape and defines a diameter slightly larger than the diameter of the central opening 84 of the washer 14. Referring to FIGS. 1 and 5, the washer 14 is thereby adapted to articulate on the ball portion 90 of the locknut 16.

Figure 9:
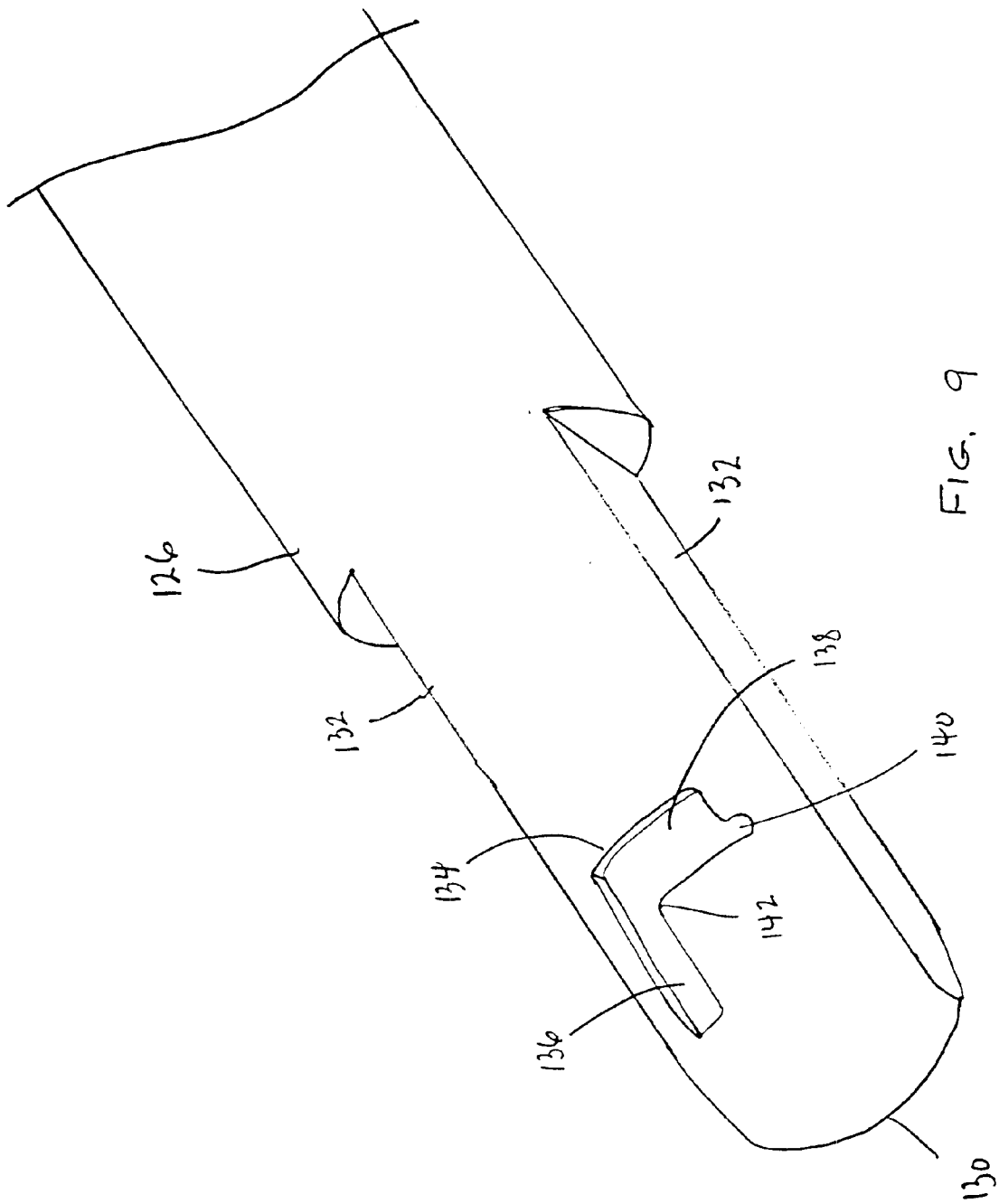
FIG. 9 is an enlarged perspective view of the distal end of the introducer of FIG. 7.

Turning now to FIGS. 7 and 8, an introducer 100 adapted to introduce the port device into an incision in the chest wall and also to effect movement of the swivels between closed and open configurations is shown. The introducer 100 includes a central tubular handle 102, a proximal cap 104, and a mandrel 106 extending through the handle 102 and coupled to the cap 104. The handle 102 includes a proximal stop notch 107, and distal smaller diameter portion 108 including two diametrically-opposed hemispherical latch elements 110 for engagement within holes 82 of the port body 12, and which together form a ball latch. The latch elements 110 are provided on fingers 112 of the handle 102, which under radial force are moved radially inward. The cap 104 includes a tubular portion 114 provided with a radial hole 116, and a knob 118 which is relatively larger in diameter than the tubular portion. The tubular portion 114 of the cap 104 extends into the handle and the knob 118 seats on the proximal end 119 of the handle. The mandrel 106 includes a cylindrical shaft 120 provided with a radial bore 122 and two diametrically-opposed distal planar portions 124, and a distal actuator 126. The shaft 120 extends through the handle 102 and into the cap 104. A crosspin 128 is positioned through the radial hole 116 and into radial bore 122 securing the shaft 120 of the mandrel 106 and the cap 104 together. In addition, the crosspin 128 extends into the stop notch 107 limiting rotation of the knob (and mandrel) relative to the handle 102. The planar portions 124 provide space to permit radial movement of the latch elements 110 when the fingers 112 of the handle 102 are compressed. Referring to FIGS. 7 through 9, the actuator 126 of the mandrel 106 includes a preferably blunt end 130 and a pair of diametrically-opposed substantially planar sides 132 about the end 130. A pair of diametrically-opposed actuation grooves 134 are provided between the planar sides 132. The actuation grooves 134 are generally L-shaped and include a longitudinal portion 136 which terminates at the blunt end 130, and a transverse portion 138. The transverse portion 138 includes a notch 140.

Referring now to FIG. 10, the introducer 100 is coupled to the port device 10 by opening the swivels 30, 32 of the port device and inserting the actuator 126 of the introducer until the ball latch engages; i.e., the proximal end of the port device rides over the latch elements 110 until the latch elements catch in the holes 82 in the port body 12. With the swivels 30, 32 in the open configuration, the levers 62 (FIG. 2) are also aligned within respective longitudinal portions 136 of the actuation grooves 134 and reside therein. More particularly, the pivot axis $A_P$ of the levers 62 are located just proximal of the inner corners 142 of the grooves (FIGS. 2 and 9). Referring to FIGS. 2, 9, 11 and 12, while keeping the handle 102 fixed, the knob 118 is rotated in a clockwise direction (causing movement of the grooves 134 relative to the levers 62. The corners 142 contact the levers 62 and rotate the levers into the transverse portions of each of the grooves, thereby effecting closing of the swivels about the port body 12. One end of each lever engages a notch 140 in its respective groove 134 to "lock" the levers (and swivels) in the closed position until the knob is rotated in an opposite direction. The amount of the rotation of the knob 118 relative to the handle 102 required to effectuate the closing is relatively limited, e.g., approximately twenty-four degrees with groove 134, and contact of the crosspin 128 against the top notch 107 limits the movement.

The introducer may be provided with other shaped grooves, the rotation of which effects movement of the levers and swivels. For example, referring to FIG. 31, the J-groove 134a on the introducer 100a operates to close (or open) the swivels by clockwise rotation of approximately 45°.

The planar sides 132 of the actuator 126 are so shaped such that the swivels 30, 32 may rest thereagainst when the swivels are in the closed configuration (FIG. 12) and thereby permit the outer surface of the swivels to effectively complete the circumference of the tubular body of the port device.

Once the swivels are locked in a closed configuration about the introducer 100, the introducer may be manipulated to introduce the port device 10 into an incision in a chest wall, preferably between two ribs, or an incision in another area of human tissue. To secure the port within the incision, the knob 118 is rotated in a counter-clockwise direction, releasing the ends of the levers from the notch 140 and causing the levers to ride against their respective walls of longitudinal portions 136 and rotate about their pivot axis $A_P$. This results in aligning the levers 62 within the longitudinal portions 136 of the grooves 134 and moving the swivels into the open configuration (FIG. 10). In the open configuration, it is preferable that the swivels each be located under a respective rib. The port body 12 is pulled back to contact the ribs and then the washer 14 is moved against the outer surface of the tissue surrounding the incision. The nut 16 is advanced through the longitudinal grooves 80 to contact and press against the washer and then threadably rotated within the threads 72, 74 to lock against the washer. The swivels and washer thereby provide a clamping action about the ribs and tissue and stably secure the tubular body 12 of the port device within the chest wall.

The introducer 100 is then released from the port body 12 by depressing the fingers 112 of the handle 102. Finally, the introducer is withdrawn leaving an open port through which a surgical instrument other device may be introduced, and to which a device may be securely coupled. It will be appreciated that due to the articulating relationship of the ball portion 90 of the lock nut 16 and the washer 14, the tubular port 12 may be articulated relative to the washer, and the chest wall.

The port device may be removed from the body by reinserting the introducer in the port device such that the levers align with and enter the longitudinal grooves. The introducer is preferably coupled to the tubular body. The locknut is released, and the port device is moved slightly into the chest cavity to provide space for the swivels to fold. Then the knob of the introducer is rotated relative to the handle to cause the actuator to rotate relative to the swivels, and cause the swivels to fold against the tubular body into the closed configuration. The introducer and port device are then together withdrawn from the chest wall of the patient.

Figure 14:
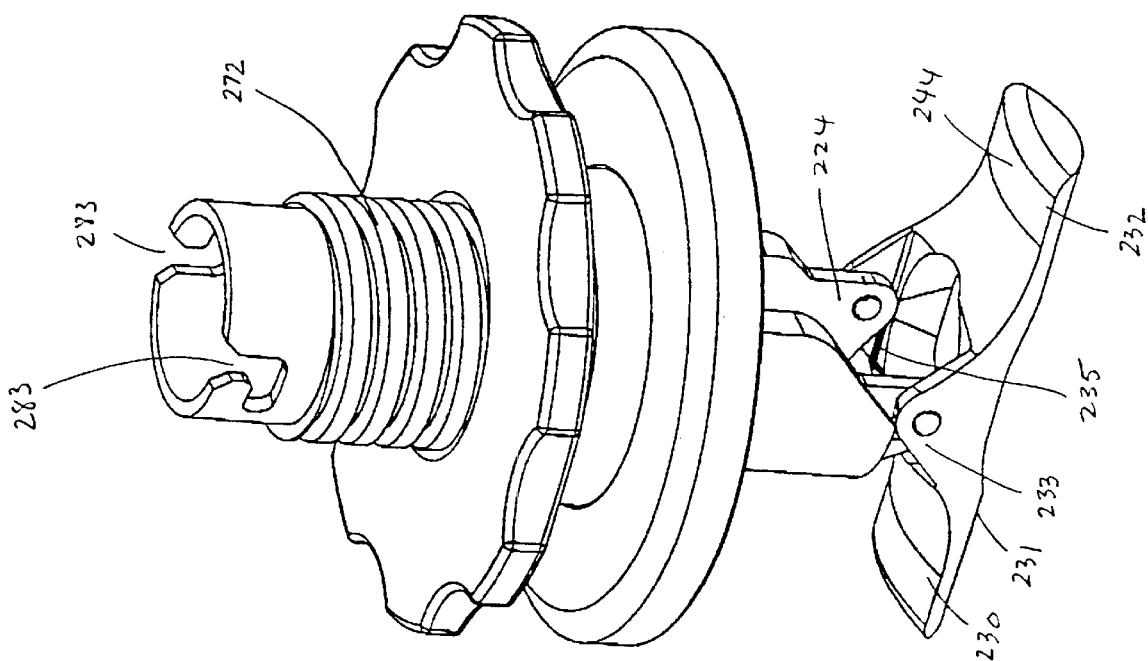
FIG. 14 is a top perspective view of the second embodiment of the port device, with the swivel shown in an open configuration.
Figure 15:
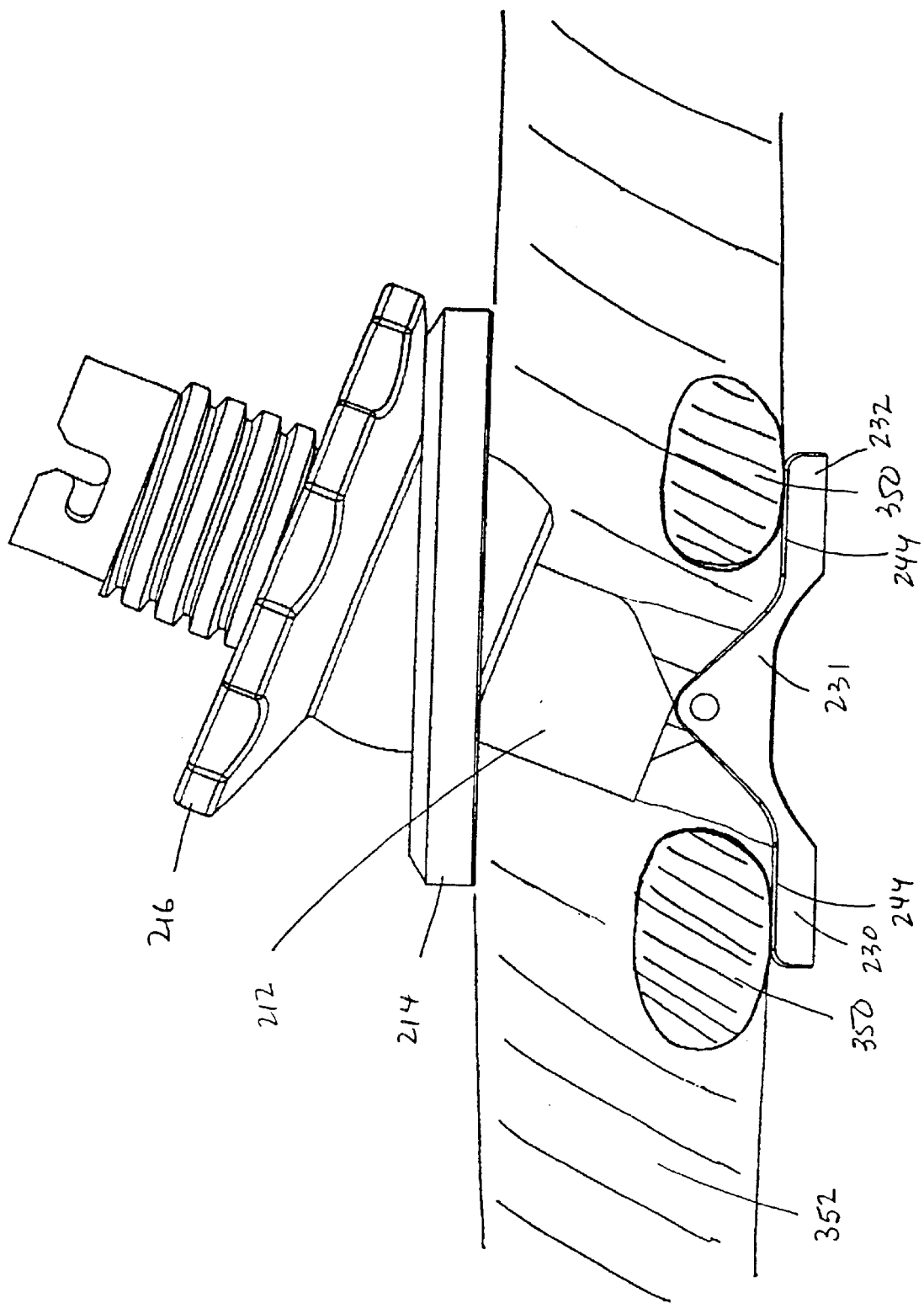
FIG. 15 is a side perspective of a second embodiment of the port device shown inserted in body tissue and between ribs of a patient.

Turning now to FIGS. 13 and 14, a second embodiment of a port device 210 according to the invention substantially similar to the first embodiment (with like parts having reference numerals incremented by 200) is shown. The tubular body 212 of the port device 210 includes a double helix thread 273 without interruptions. The proximal end of the port device includes a female bayonet coupling 283. The distal end of the tubular body includes a single swivel 231 including two arms 230, 232 and rotatably coupled at a central portion 233 to a clevis 224 formed at the distal end of the body. The inner contact surfaces 244 of the swivel are preferably provided with a contour to facilitate placement of the swivels against the ribs even when the tubular body is articulated through various angles relative to the washer. The swivel 231 is preferably biased with a spring 235 to move into an open configuration substantially perpendicular to the tubular body. As such, during insertion, a mandrel (not shown) is preferably positioned within the tubular body, and may be coupled to the female bayonet coupling, to maintain the swivel in a closed configuration substantially parallel to the tubular body. Then, when the proximal end of the swivel 231 is past the ribs (see FIG. 15), the mandrel is removed from the tubular body, and the spring 235 automatically rotates the swivel 231 into the open configuration with the swivel being captured by the ribs 350. The washer 214 and locknut 216, which are preferably the same as described in the first embodiment, are then tightened against the tissue 352 (as shown in FIG. 15), clamping the ribs 350 and tissue 352 between the washer and swivel.

The swivel 231 may be returned to the closed configuration for removal from the patient body by loosening the locknut and washer, pushing the swivel distally into the chest cavity, and inserting the mandrel back through the tubular body and causing contact against an arm of the swivel to force the swivel to rotate back into the closed configuration.

Figure 32:
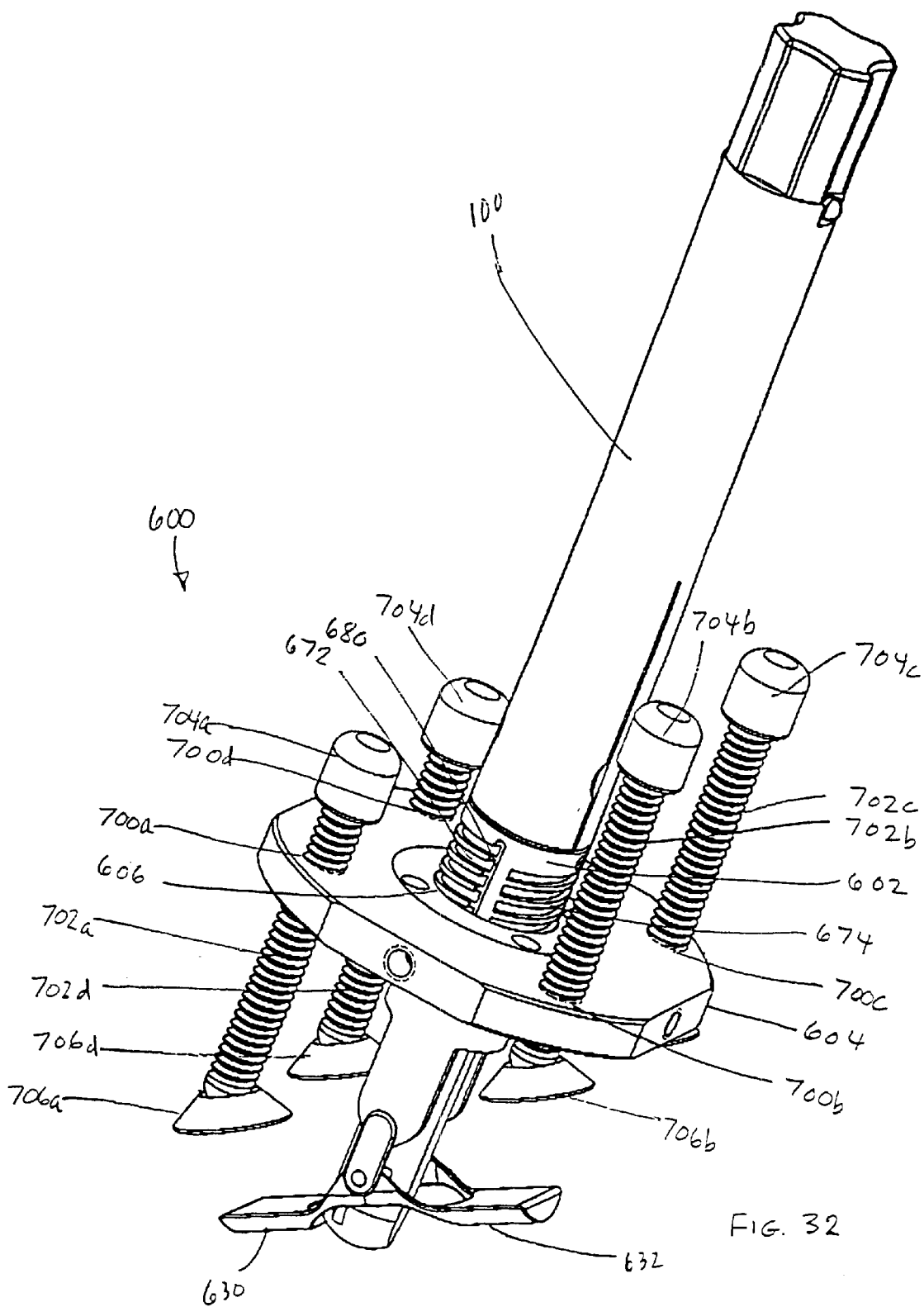
FIG. 32 is a perspective view of a third embodiment of a port device according to the invention.

Turning now to FIG. 32, a third embodiment of a port device 600 according to the invention is shown. The port device includes a tubular body 602 and an adjustable platform 604. The tubular body 602 includes swivels 630, 632 at a distal end thereof, and threads 672, 674 and longitudinal grooves 680 along the body, preferably the same as those described with respect the first embodiment. The platform 604 includes a central opening 606 and nubs which extend into the opening (the nubs are not shown, but are substantially similar to nubs 91, 92 in the first embodiment). The nubs permit the platform to travel in the longitudinal grooves 680 and threads 672, 674 to move and threadably lock the platform relative to the body 602. The platform 604 also includes a plurality of, e.g., four, threaded bores 700a–d preferably equally spaced about the central opening 606. Bolts 702a–d are thread partially through the bores 700a–d, and each is provided with a proximal handle 704a–d by which the bolt may be manually rotated, and a distal foot 706a–d pivotable about the end distal end of the bolt.

An introducer 100, shown coupled to the port device 600, is preferably utilized to insert and deploy the swivels 630, 632 of the port device 600 into the chest wall, and is then disengaged and removed from the port. The platform 604 is then angularly adjusted relative to the chest wall by rotating the bolts. That is, if it is desired to have the platform 604 be oriented substantially planar with the chest wall, each bolt 702a–d, by rotation of its respective handle 704–d, is tightened by substantially the same amount to cause the chest wall to be evenly clamped between the swivels 630, 632 and the feet 706a–d. However, if it is desired to cause the platform, and port body 602 therein, be at an angle relative to the chest wall (to provide better access to the surgical site), the bolts 706a–d may be thread into the bores 700a–d by different amounts to cause the platform 604 to assume a desired angle relative to the chest wall.

Figure 34:
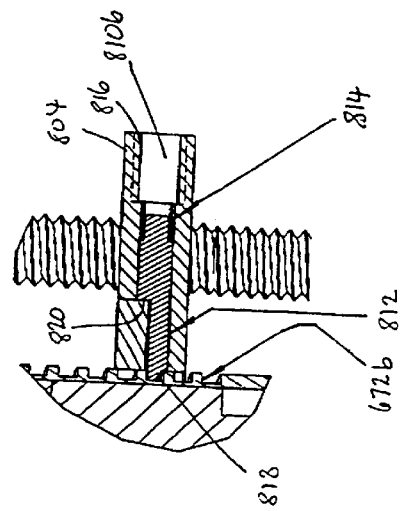
FIG. 34 is a partial section view across line 34—34 in FIG. 33 of the tubular body of the fourth embodiment of the port device of the invention.
Figure 33:
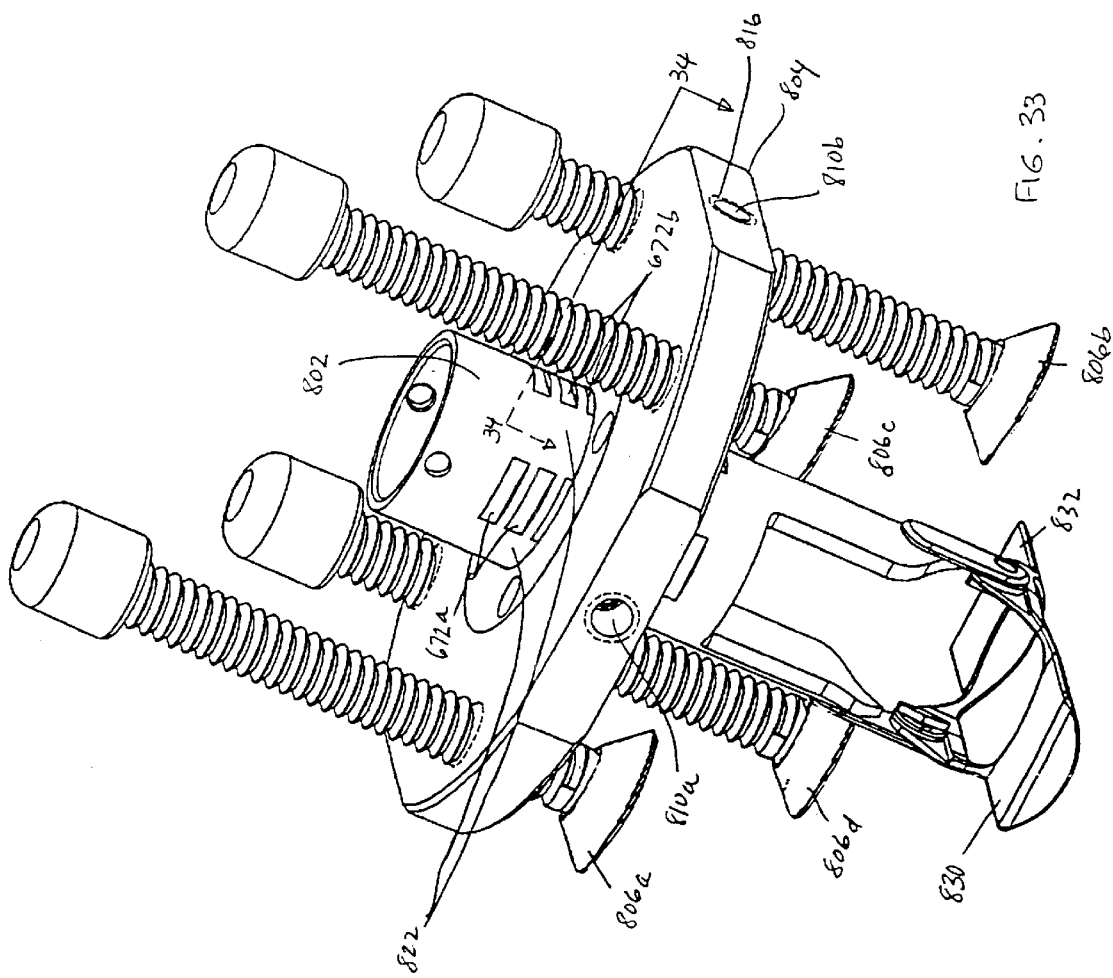
FIG. 33 is a perspective view of a fourth embodiment of a port device according to the invention.

Referring now to FIGS. 33 and 34, a fourth embodiment of a port device 800 according to the invention, substantially similar to the third embodiment 600, is shown. The tubular body 802 of the port device is provided with four sets of grooves 672a, 672b (672c and 672d not shown but located diametrically opposite 672a and 672b, respectively), rather than the threads 672, 674 of body 602 (FIG. 32). Each set of grooves 672a–d extends parallel to a respective tangent on the surface of the body and offset by ninety degrees about the body. The platform 804 includes four radial channels 810a, 810b (810c and 810d not shown) located ninety degrees apart. A ratchet pin 812 is provided in each of the channels 810a–d. A spring 814 is positioned within each channel 810a–d to bias each ratchet pin 812 toward a respective set of grooves 672a–d, and a locking collar 816 maintains the spring within the channel. The ratchet pin 812 is shaped to include a beveled edge 818 facilitating radial outward movement of the ratchet pin against the bias of the spring when the platform is moved distally over the grooves of the tubular body. In addition, the ratchet pin includes a stop 820 to limit inward radial movement. This configuration permits the platform to be readily and rapidly moved distally along the tubular body to a desired location with the ratchet pins locking within the grooves to prevent proximal movement of the platform, and thereby clamping the chest wall between the swivels 830, 832 and the feet 806a–d coupled to the platform. The feet may then be adjusted to orient the platform at an angle relative to the chest wall.

When it is desired to release the platform from about the tubular body, the feet are loosened from against the chest, and the platform is rotated approximately forty-five degrees such that the ratchet pins lie along smooth portions 822 of the tubular body. The platform may then be moved proximally relative to the tubular body without substantial resistance.

Figure 54:
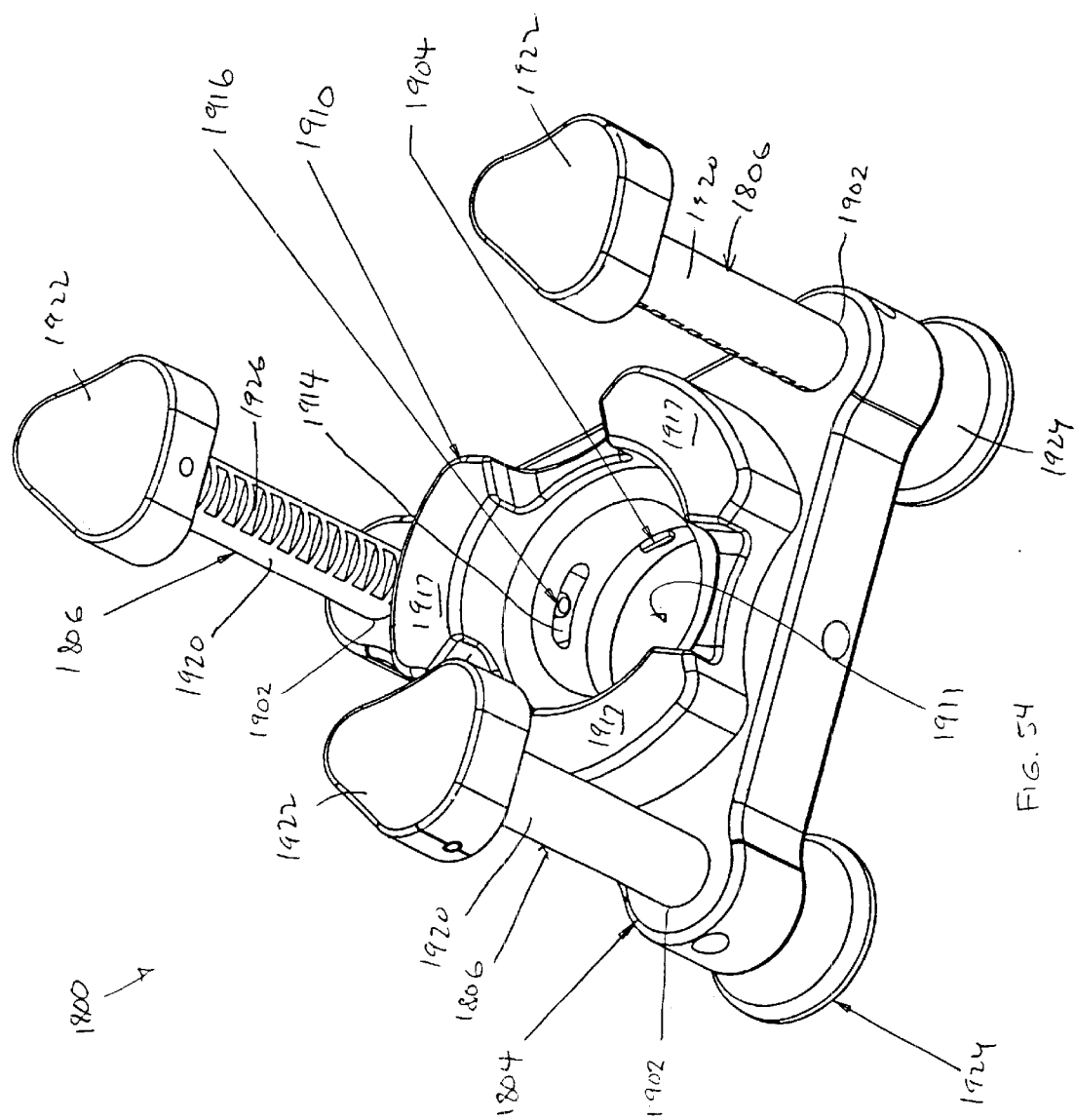
FIG. 54 is a top perspective view of a fifth embodiment of a port device according to the invention.

Turning now to FIGS. 54 through 58, a fifth embodiment of a port device 1800 according to the invention is shown. The port device 1800 includes a port tube (tubular body or port body) 1802 (FIGS. 57 and 58), a platform 1804 (FIG. 54), and a plurality of legs 1806 (FIG. 54). Referring to FIGS. 57 and 58, the port tube 1802, at a distal end, includes a pair of swivels 1830, 1832 coupled to the tube with axle members, as described above (see FIG. 2), and a proximal body 1812 having a plurality of longitudinally-spaced circumferential grooves 1872. The proximal end of the body includes preferably two diametrically opposite catches 1882 for receiving latches of an introducer, and coupling thereto, as described below.

Referring back to FIGS. 54 through 56, the platform 1804 is preferably generally triangular-shaped and includes a central opening 1900 (FIG. 56) in which to receive the port tube 1802, and three peripheral leg holes 1902 preferably located adjacent the corners of the platform in which to receive the legs 1806. Three ratchet pins 1904, each having a beveled lower edge 1905, are evenly spaced about the central opening 1900. The ratchet pins 1904 are biased by respective springs 1906 to extend radially inward into the central opening 1900. Each ratchet pin 1904 includes an upwardly extending convex boss portion 1908. A port tube release collar 1910 is provided within the central opening 1900 and includes a central passageway 1911. The ratchet pins 1904 extend into the central passageway 1911. The collar 1910 also includes a convex groove 1912 over each boss portion 1908. In addition, the collar includes a slot 1914 between each groove 1912. One peg 1916 extends through each slot 1914, and is fixed in the platform, permitting the collar 1910 to be rotated relative to the central opening 1900 a limited amount; i.e., the distance the peg 1916 may travel within the slot 1914. Moreover, the pegs 1916 couple the collar to the platform 1804 and prevent its release. When the collar 1910 is rotated relative to the platform 1804 from a first position in which the center of each groove 1912 is positioned over a respective boss portion 1908, the respective surfaces of the convex grooves contact the boss portions and move the ratchet pins 1904 against the bias of the springs 1906 to retract the ratchet pins from the central opening 1900. The collar 1910 preferably includes upper knob portions 1917 grippable by human fingers to facilitate the limited rotation of the collar 1910 relative to the platform and the resulting 'release' of the ratchet pins.

When the platform 1804 is distally forced over the port tube 1802, the grooves 1872 of the port tube 1802 contact the beveled ratchet pins 1904 and cause radial outward movement of the pins against the bias of the springs 1906. When the platform 1804 is moved a desired distance over the port tube 1802, the relative distal force is removed and the ratchet pins engage within the grooves to prevent proximal movement of the platform relative to the tube. The platform 1804 may then be released from over the port tube 1802 by rotation of the collar 1910 relative to the platform. This configuration permits the platform to be readily and rapidly moved distally along the port tube to a desired location with the ratchet pins locking within the grooves of the port tube to prevent proximal movement of the platform.

Each of the legs 1806 includes a generally cylindrical shaft 1920, an upper knob 1922 facilitating downward (distal) force to be placed on the leg, and a lower foot 1924 which is pivotable on the distal end of the shaft 1920. A portion along a length of the shaft 1920 includes a rack of teeth 1926 defined by grooves 1928 cut parallel to a tangent of the shaft. Each shaft 1920 is provided into a respective leg hole 1902 of the platform 1804. The platform includes, for each leg hole, a ratchet pin 1930 having a convex tip 1932 with a beveled upper surface 1934. The ratchet pin 1930 is biased by a spring 1936 to extend radially into the leg hole 1902. Each leg may be easily and rapidly moved distally relative to the platform 1804 by pushing the leg distally, causing the beveled upper surface 1934 to contact the teeth 1926 and be moved radially inward against the bias of the spring 1936 to permit movement of the leg 1920 through its respective leg hole 1902. However, the legs are prevented from relative proximal movement by the capture of the ratchet pin 1932 in a groove 1928 between the teeth 1926. Each leg may then be released by rotating the leg relative to the platform such that the inner surface of the groove 1928 in which the ratchet pin 1930 seats contacts the tip 1932 of the pin and moves the pin out of the leg hole. When the leg is sufficiently rotated to cause a cylindrical portion of the leg to be facing the ratchet pin 1934, the pin is prevented from entering the leg hole and cannot contact the teeth or enter the grooves, as the teeth and grooves are rotated out of the way. As such, the legs may then be freely moved proximally and distally. It will be appreciated that the legs may be independently moved relative to the platform to permit a variety of longitudinal and angular adjustments. In addition, the legs define a tripod which is extremely stable. Furthermore, the degree of adjustment and clamping ability is also facilitated by the adjustability of the platform relative to the tube.

Figure 31:
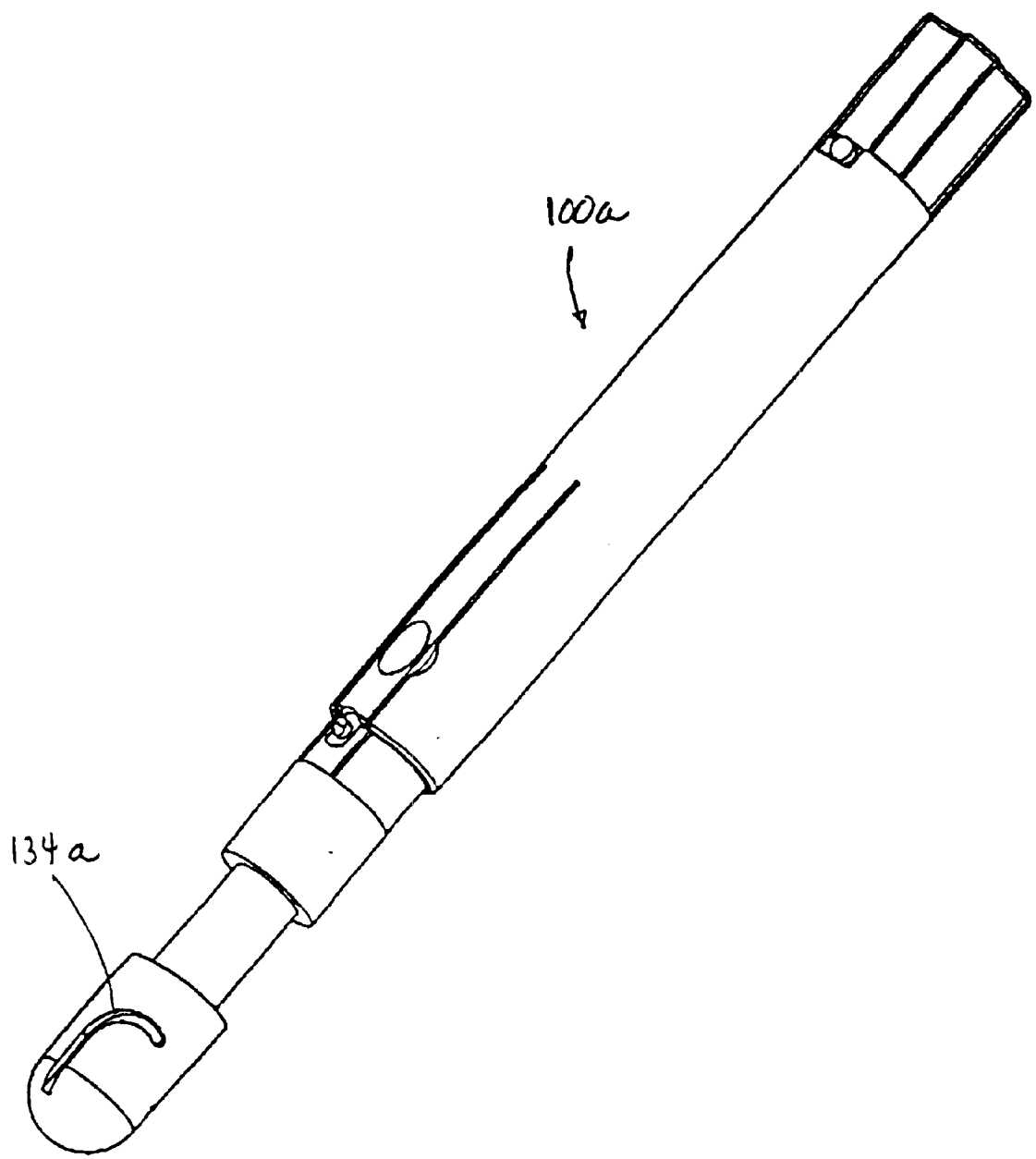
FIG. 31 is a perspective view of a second embodiment of a port introducer according to the invention.

Referring now to FIGS. 57 and 58, an introducer 2000 is coupled to the port device to aid insertion of the port device into the chest wall and to enable movement of the swivels into the clamping positions. The introducer includes a mandrel 2002 extending through a guiding sleeve 2004. The mandrel 2002 includes a handle 2006 at a proximal end, a central shaft portion 2008, and a distal actuator 2010. A pin 2012 is provided in a proximal portion of the shaft and protrudes above the surface of the shaft. The actuator 2010 includes a J-hook groove, as shown with respect to the J-hook groove 134a of the actuator 100a (FIG. 31). The sleeve 2004 includes a proximal J-hook slot 2016 and distal resilient fingers 2018 having tabs or latches 2020 adapted to engage the catches 1882 of the port tube 1802.

In operation, the swivels 1830 and 1832 of the port 1800 are first manually moved into an open configuration. Next, the sleeve 2004 of the introducer 2000 is coupled to the port 1800 by engaging the tabs 2020 of sleeve 2004 in the catches 1882 of the port tube 1802. The mandrel 2002 is then inserted through the sleeve 2004 such that the pin 2012 on the mandrel is aligned with the proximal end of the J slot 2016 of the sleeve. This causes the levers 62 (FIG. 2) of the open configuration swivels to be aligned with the distal end of the J-groove of the actuator 2010. Referring to FIG. 58, the handle 2006 is then moved distally and rotated relative to the sleeve 2004 to move the pin 2012 through the slot 2016 in the sleeve to the distal end of the slot. Consequently, the actuator is moved in a manner which causes the J-groove to guide the levers in a manner which rotates the swivels 1830, 1832 into a closed configuration.

The introducer 2000 is then maneuvered to insert the closed port tube 1802 through an opening in the chest wall. The handle is then operated in an opposite direction to open the swivels 1830, 1832 in the chest wall. The platform 1804 is then moved over the introducer 2000 and ratcheted over the port tube to clamp the chest wall between the open swivels and the feet 1924 of the legs 1920. The legs 1920 may then be ratcheted distally or released to be moved proximally relative to the platform to desirably orient the port tube relative to the chest wall. The introducer is then released by radially inwardly compressing the resilient fingers 2018 to release the tabs 2020 from the catches 1882 and then withdrawing the introducer 2000 from the port tube 1802. Endoscopic instruments may then be inserted through the port tube 1802, as discussed above.

When the procedure is complete, the introducer is again coupled to the port tube, and the platform may be released from over the port tube by releasing the ratchet engagement from the legs and port tube. The introducer is then operated to move the swivels into the closed position and the port tube is withdrawn from the chest wall.

While the port device has been disclosed with various swivel elements, it will be appreciated that other swivel elements, and means for opening the swivel elements, including springs and mechanical systems may be used as well. In addition, while particular types of connecting means for coupling devices, e.g., the introducer and surgical instruments to the port have been disclosed, it will be understood that other connecting means can be used. Also, while various means for orienting the port device relative to the heart wall have been disclosed, it will be appreciated that other such orienting means can be used was well. Furthermore, it will be appreciated that any one or more of the features of the individual port device embodiments may be incorporated into the other embodiments.

Figure 16:
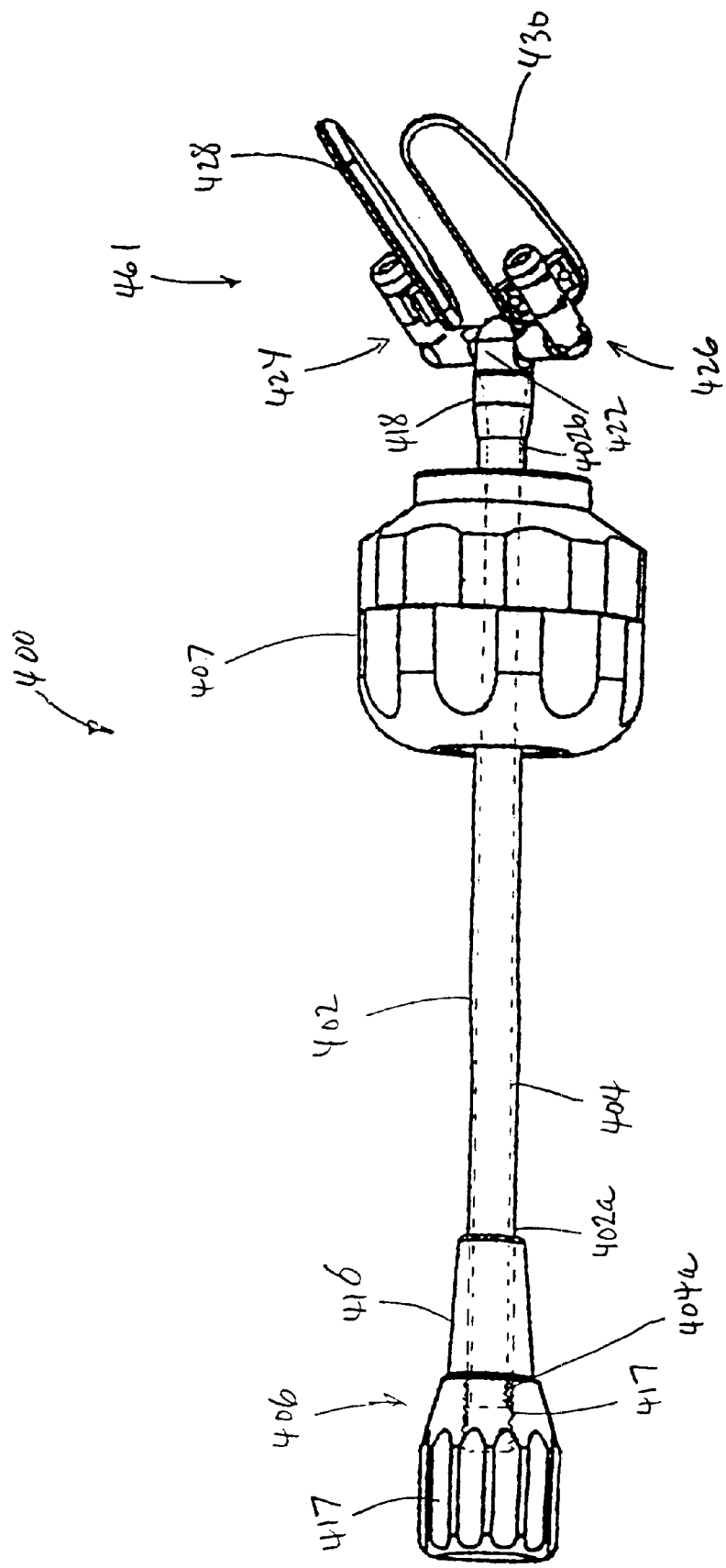
FIG. 16 is a side perspective view of a first embodiment of a heart stabilizer device according to the invention.

Turning now to FIG. 16, a first embodiment of the heart stabilizer 400 preferably includes a hollow shaft 402, a rod 404 extending through the shaft, and a proximal control handle 406 coupled to the proximal ends of the shaft 402 and rod 404 to move the rod longitudinally within the shaft, as described in more detail below. The shaft 402 and rod 404 are keyed (not shown) such that the rod cannot rotate relative to the shaft. A shaft lock 407 is provided about the shaft 402 and operates to lock the heart stabilizer 400 to a port device, such as port devices 10 (FIG. 1) and 210 (FIG. 13), and also permits locking the shaft 402 in numerous longitudinal and angular positions relative to the port device.

Figure 17:
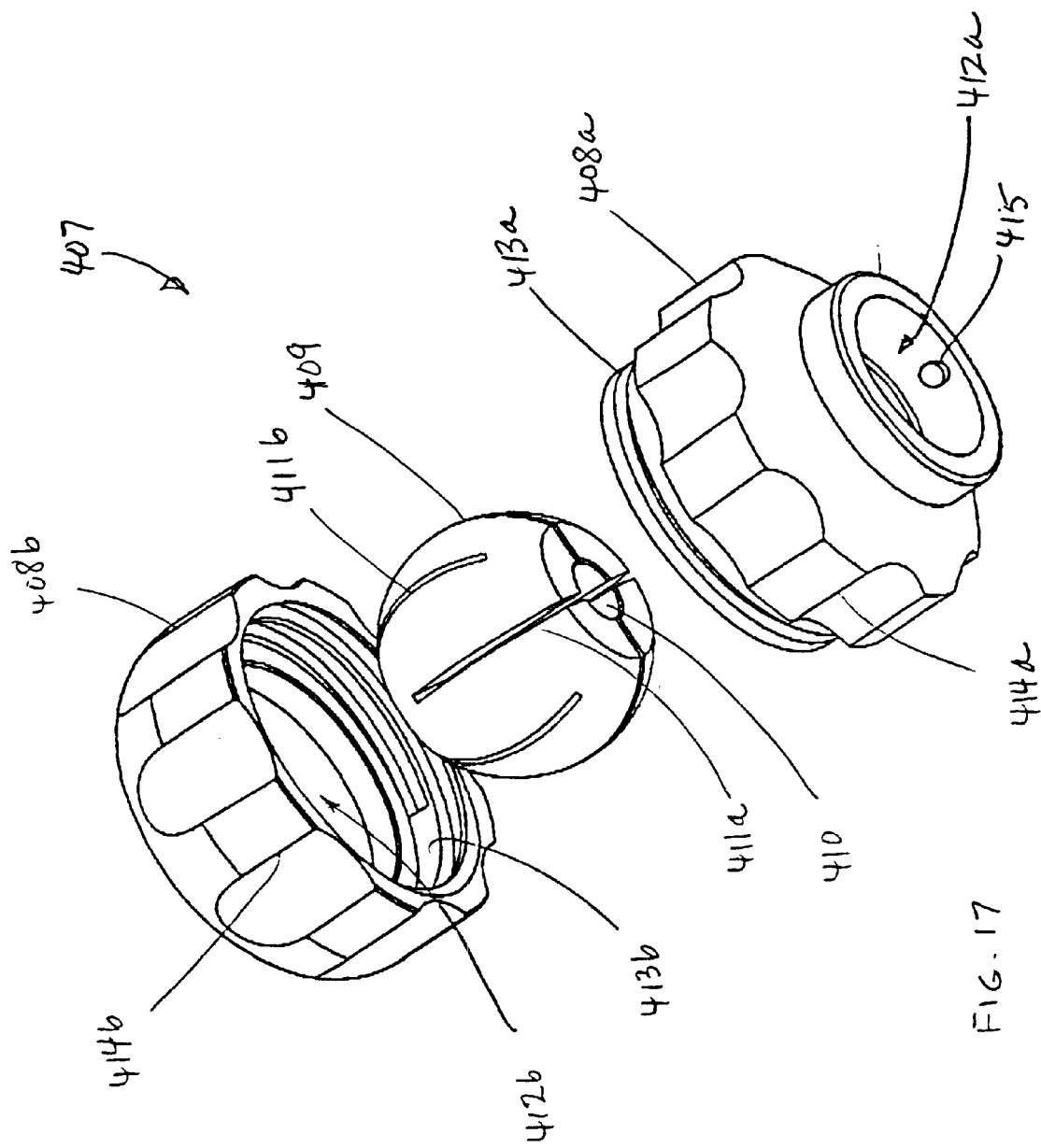
FIG. 17 is an exploded perspective view of the shaft lock of the heart stabilizer device of FIG. 16.

More particularly, referring to FIGS. 16 and 17, the shaft lock 407 includes a port connector 408a, a cap 408b, and a ball element 409 between the port connector and cap. The ball element 409 includes a shaft bore 410, a first set of diametric slots 411a in one end of the ball element, and a second set of diametric slots 411b in the other end of the ball element. The two sets of slots 411a and 411b permit radial compression of the ball element 409 to cause the diameter of the shaft bore 410 to decrease. The port connector 408a and cap 408b each include an opening 412a, 412b, a mating means 413a, 413b, e.g., threads, for mating with each other, and a finger gripping structure 414a, 414b to facilitate relative rotation of the port connector and cap about the mating means. The port connector 408a also includes a port mating structure 415, e.g., a bayonet, for mating with the female bayonet coupling 283 of a port 210 (FIG. 14). The shaft 402 extends through the shaft bore 410 and, when the port connector 408a, 408b are loosely mated with each other, the shaft and ball element 409 may be pivoted relative to the port connector and cap, and the shaft may be moved longitudinally within the bore 410 relative to the shaft lock. When the cap 408b is tightened on the port connector 408a, the ball element 409 and shaft 402 are locked in their respective positions.

Referring to back to FIG. 16, the control handle 406 includes a knob mount 416 fixedly coupled to the proximal end 402a of the shaft 402, and a knob 417 rotatably coupled to the mount 416. The knob 416 includes a threaded bore 417, and the proximal end 404a of the rod 404 is threaded, and threadably engaged within the bore of the knob 417. The rotation of the knob 417 relative to the mount 416 causes the rod 404 to move longitudinally relative to the shaft 402, as the keyed rod cannot rotate relative to the shaft.

Figure 18:
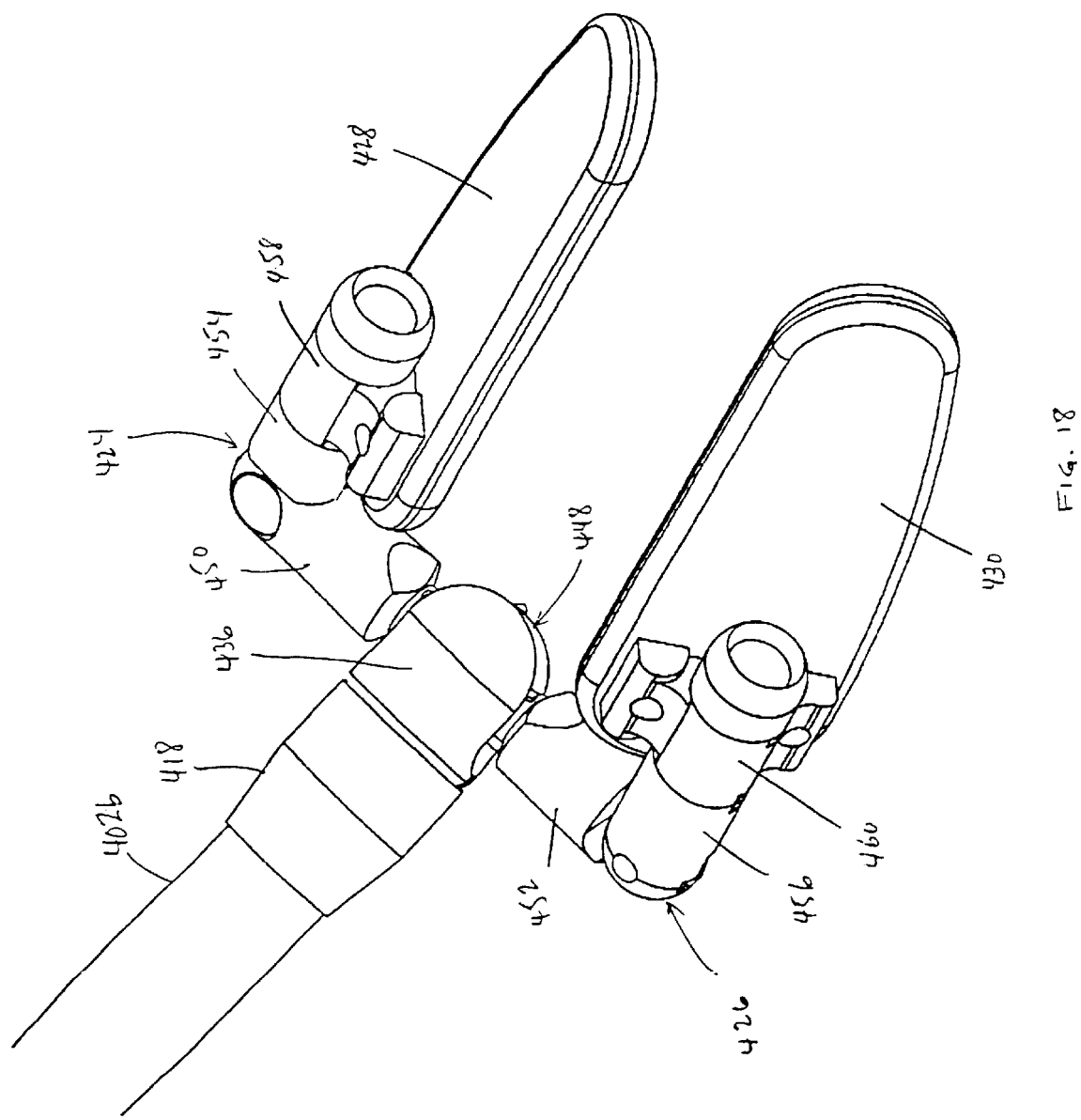
FIG. 18 is a perspective view of the stabilizing mechanism at the distal end of the heart stabilizer device of FIG. 16.
Figure 19:
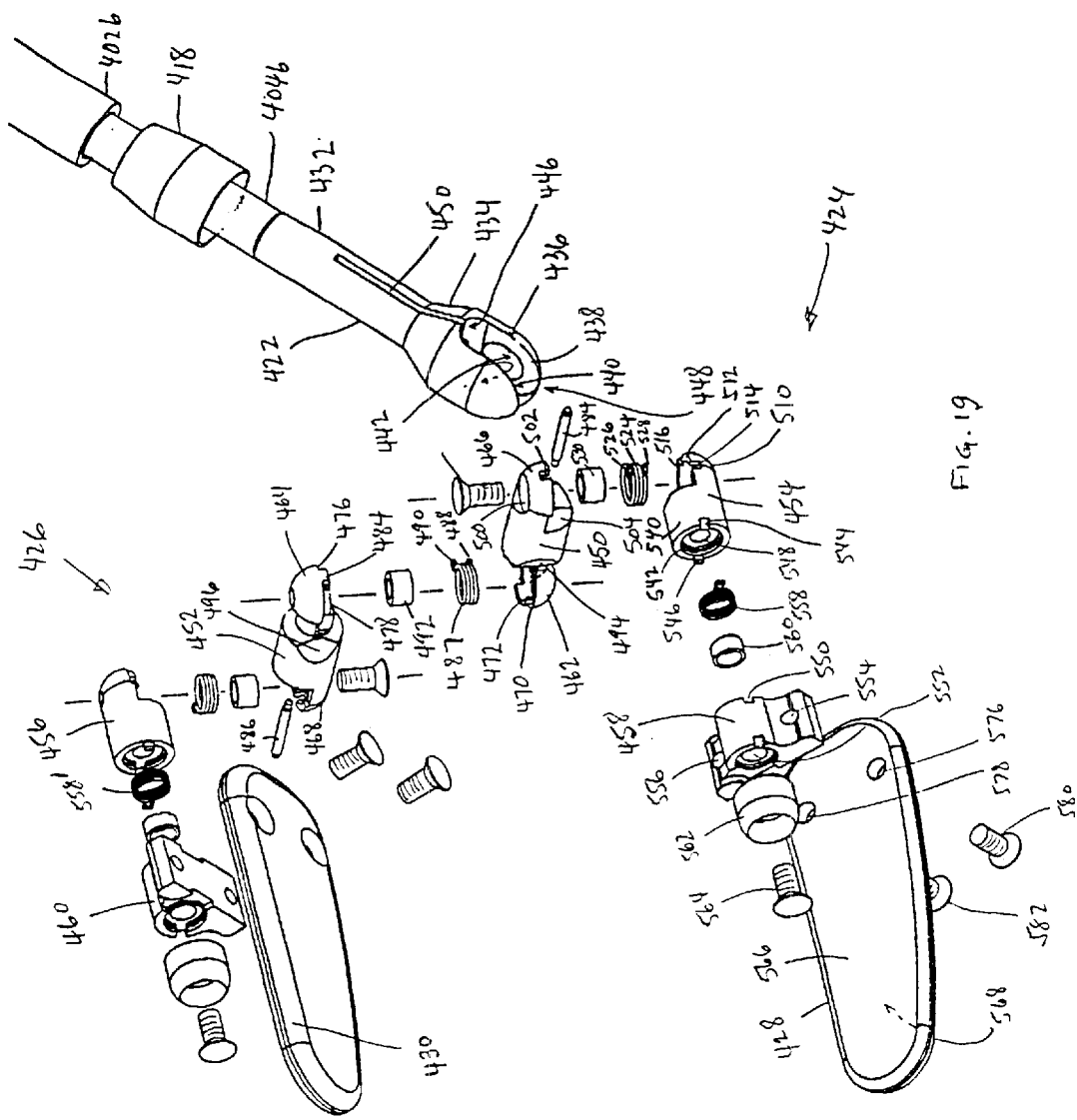
FIG. 19 is an exploded perspective view of the stabilizing assembly of the heart stabilizer device of FIG. 16.

Referring now to FIGS. 16, 18 and 19, the distal end 402b of the shaft 402 is provided with a collar 418. The distal end 404b of the rod 404 is coupled to a clevis 422. The clevis 422 includes a post portion 432 coupled to the rod 404, a frustoconical portion 434, and a U-shaped socket 436 including side walls 438, 440 with spherical concavities 442, a back wall 446, and a front opening 448 extending through an approximately 180° arc. A slot 450 extends from the back wall 446, through the frustoconical portion 434, and into the post portion 432. When the rod 404 is moved proximally relative to the shaft 402, by operation of the handle 406, the collar 418 rides against the frustoconical portion 434 of the clevis 422, causing compression of the socket 436. Conversely, when the rod 404 is moved distally relative to the shaft 402, the frustoconical portion 434 of the clevis 422 is released from the collar, permitting the socket 436 to slightly expand.

Referring to FIGS. 18 through 21, two articulating arms 424, 426 are coupled in the socket 436 of the clevis, and a rotatable stabilizing foot 428, 430 is coupled to the end of each arm. The first and second articulating arms 424, 426 each include an upper arm 450, 452, a lower arm 454, 456, and a wrist mount 458, 460. Stabilizing feet 428, 430 are coupled to the wrist mounts, 458, 460, respectively. The articulating arms 424, 426 and the feet together define a stabilizing assembly 461.

More particularly, each of the first and second upper arms 450, 452 includes a partly hollow, generally hemispherical shoulder 462, 464 at one end and an upper elbow portion 466, 468 at the other end. The first shoulder 462 (of the first upper arm) includes rim 470 defining a first upper cam 472, and the second shoulder 464 (of the second upper arm) includes a rim 476 defining a second upper cam 478. In addition, each of the first and second upper arms includes a pin bore 480, 482 extending longitudinally through the arms. Lock pins 484, 486, which function to limit the movement of the first and second upper arms 450, 452 relative to each other as described in more detail below, are provided within the pin bores 480, 482.

The first and second shoulders 462, 464 are oriented and configured such that they together substantially define a sphere. A shoulder spring 487 is positioned within the sphere defined by the shoulders, and the ends 488, 490 of the spring 487 are coupled to and about the rims 470, 476, respectively, with the spring 487 under helical compression to urge the upper arms 450, 452 away from each another. A spacer 492 is provided within the spring 487 to stabilize the spring within the shoulders. The shoulders together are provided in the socket 436, with each hemispherical shoulder residing partially within a respective one of the concavities 442. While the shoulders 462, 464 appear to form a ball within the socket 436, it will be appreciated that the shoulders provide additional function over a ball in that the two upper arms 450, 452 are permitted to independently rotate relative to each other at the shoulders. The spring 487 is adapted to bias the upper arms 450, 452 into an open position in which the two are in alignment; i.e., at substantially 180O relative to each other. Each upper arm 450, 452 also includes a front bevel 494, 496. As such, when the upper arms are moved against the bias of the spring 487 toward each other, an angle α as small as approximately 45°, and preferably 47°, may be defined therebetween (FIG. 20), with the bevels 494, 496 minimizing interference between the two upper arms which would otherwise limit the ability to define such a small angle α therebetween.

The description of the lower arms 454, 456 and the coupling of the lower arms to the upper arms will now be described with respect to upper arm 450 and lower arm 454 of the first articulating arm 424, with it being understood that the lower arms and their couplings of the second articulating arm 426 are each substantially the same as in the first articulating arm, but installed upside down relative to the first articulating arm.

The upper elbow portion 466 of upper arm 450 is rotatably coupled to a lower elbow portion of lower arm 454. The upper elbow portion 466 is generally hemispherical in shape and includes a countersunk screw hole 500 and a first elbow spring catch 502. The upper arm 454 is provided with a bevel 504 adjacent the upper elbow portion 466. The lower arm 454 includes a generally hollow, substantially hemispherical lower elbow portion 510 which mates with the upper elbow portion 466 of the upper arm 450. The lower elbow portion 510 includes a rim 512 defining a second elbow spring catch 514, and a lower arm cam 516 including a cam lock 518 and a cam stop 520. The elbow portion 510 also includes a threaded screw hole 522.

An elbow spring 524, under helical tension, is provided within the upper and lower elbow portions 466, 510. The elbow spring 524 includes ends 526, 528 which are coupled in the first and second elbow spring catches 502, 512, respectively, biasing the upper and lower arms toward a configuration having a relatively smaller angle therebetween. A tubular spacer 530 is provided within the elbow spring 524 to stabilize the spring within the shoulders and provide a pathway for a screw 532 which extends into the screw hole 500 and is threadably engaged in screw hole 522 to secure the upper and lower arms together in a manner which permits the lower arm to pivot relative to the upper arm.

The lower end of the lower arm includes an upper wrist portion 540 provided with a rim 542 oriented orthogonally to the rim 512, and a threaded bore 548. The rim 542 defines a first wrist spring catch 544 and a stop 546.

The wrist mount 458 includes a second wrist spring catch 550, a throughbore 552, and two threaded mounting holes 554, 556; one provided on either side of the throughbore 552. A wrist spring 558 is provided about a spacer 560 between the upper wrist portion and the wrist mount and engages the first and second wrist spring catches. The wrist spring 558 is biased to rotate the wrist mount 458 clockwise relative to the upper wrist portion 540 when viewed in the direction of the lower arm 454 toward the wrist mount 458. A wrist spring 558' in the second arm 426 rotates a respective wrist mount in an opposite direction such that the wrist mounts are urged to rotate away from each other.

A collar 562 is provided in alignment with the throughbore 552, and a screw 564 extends through the collar 562 and throughbore 552 and is secured in the threaded bore 548 of the upper wrist portion 540.

The foot 428 includes an outer surface 566, a contact surface 568, and two spaced apart bores 576, 578 which align with the threaded bores 554, 556 of the wrist mount 458. The foot 428 is coupled at its outer surface 566 to the wrist mount 458 with screws 580, 582 extending into the bores 576, 578 and threadably engaged within bores 554, 556 of the wrist mount 458.

Figure 20:
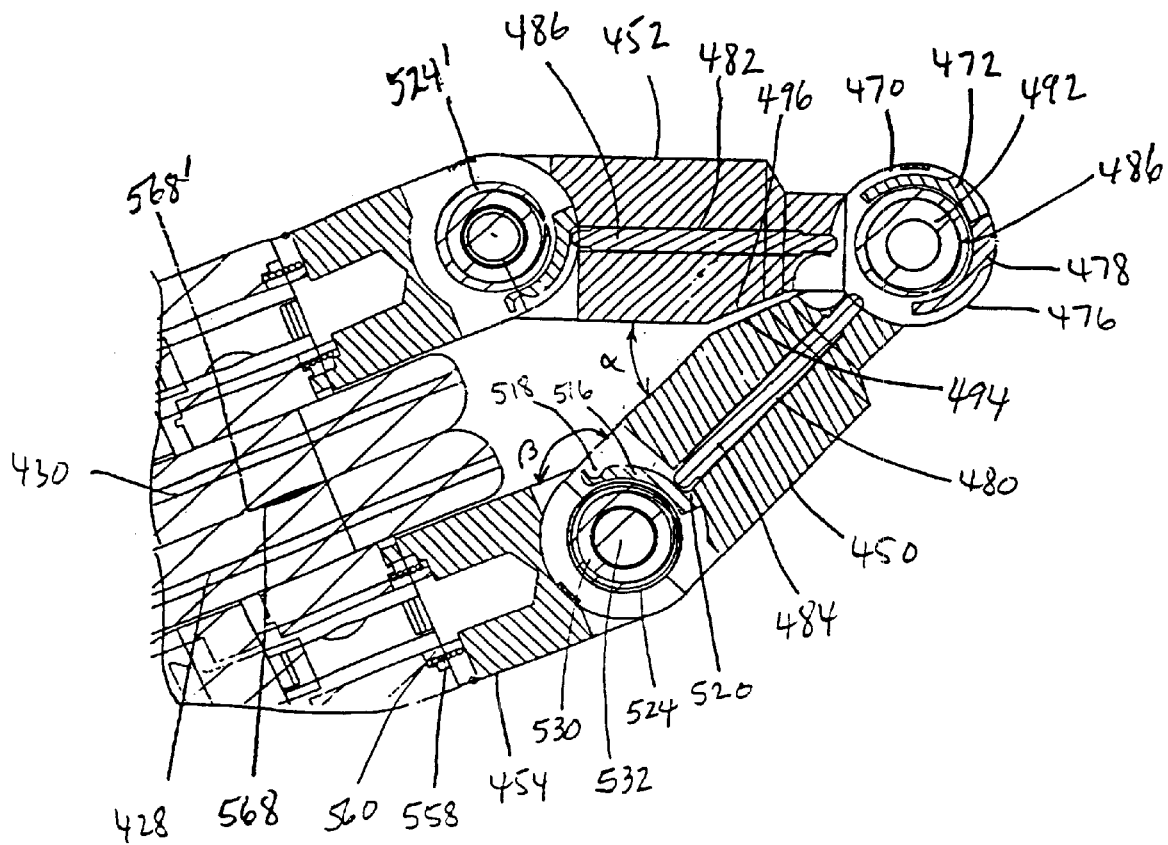
FIG. 20 is a broken longitudinal section view of the shoulders and upper arms of the stabilizing assembly of the heart stabilizer device of FIG. 16 shown in a closed position.
Figure 21:
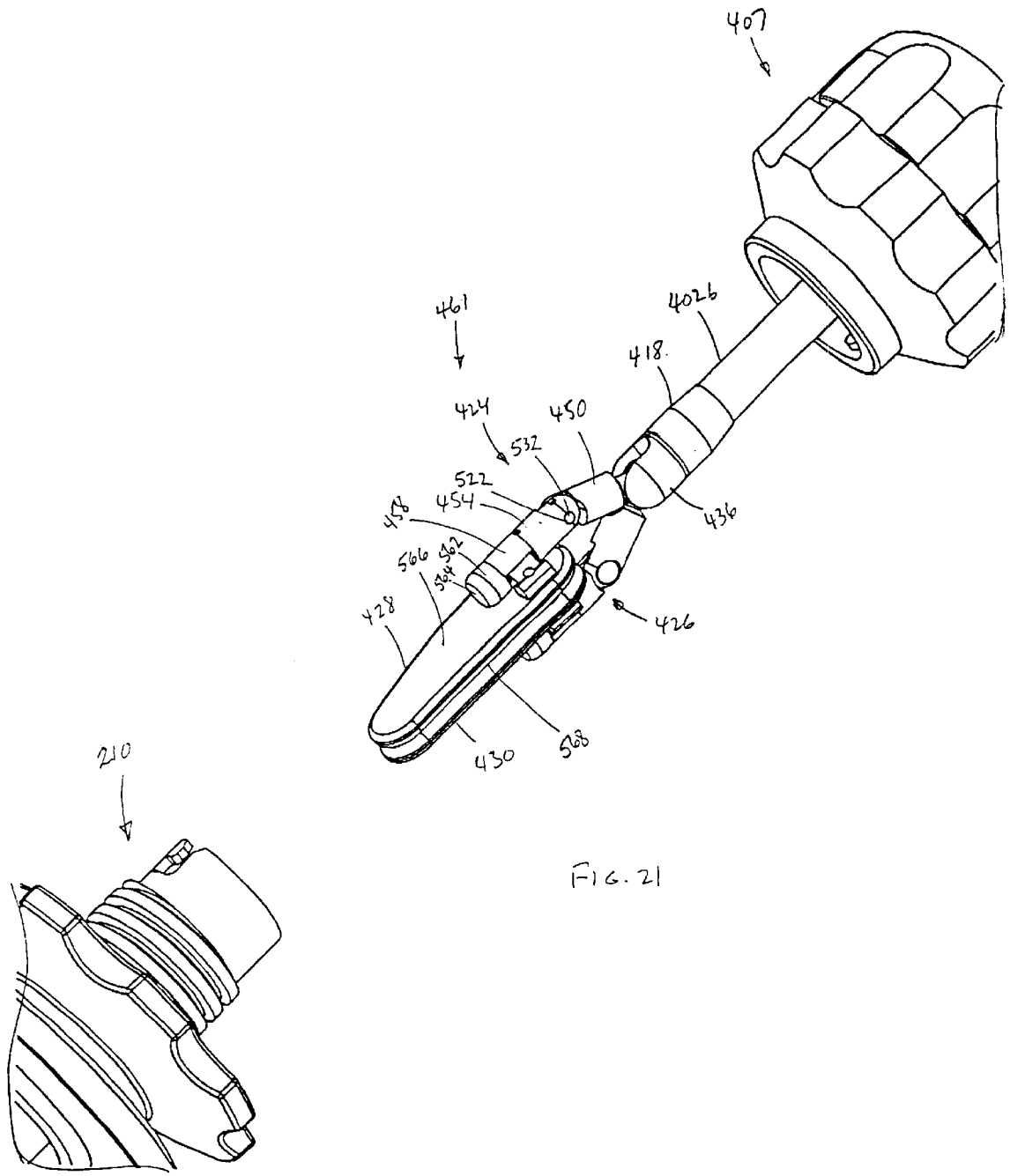
FIG. 21 is a broken bottom perspective view of the stabilizing assembly of the heart stabilizer device of FIG. 16 shown in a closed position and a port device according to the invention.

The operation of the heart stabilizer 410 and particularly the stabilizing assembly 461 will now be described, with reference numerals terminating in a prime referring to elements of the second articulating arm. Referring to FIGS. 20 and 21, the articulating arms 424, 426 and feet 428, 430 are manually folded into the illustrated configuration. That is, the upper arms 450, 452 are folded about the shoulders, and the feet 428, 430 are rotated inward toward each other such that the respective contact surfaces 568, 568' and in contact. In this configuration the upper arms 450, 452 have an angle α of approximately 47°, and the feet 428, 430 are oriented substantially parallel to the shaft 402 of the heart stabilization device 410. The handle 406 is then operated to cause the collar 418 to compress the socket 436 about the shoulders 462, 464 of the upper arms and thereby lock the upper arms 450, 452, lower arms 454, 456, and feet 428, 430 in their relative positions and present a relatively small cross-sectional area for insertion through a port 210.

Figure 22:
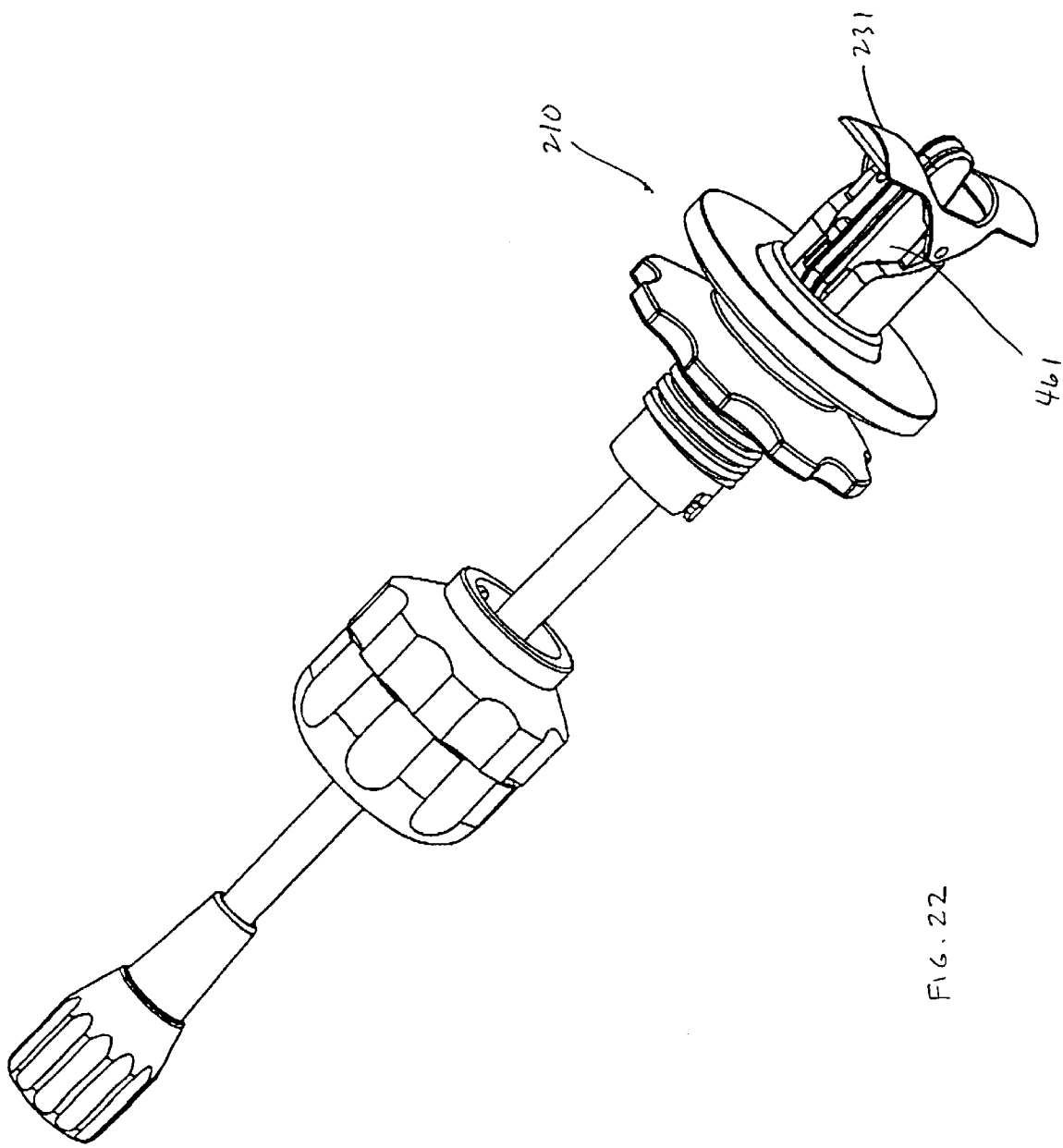
FIG. 22 is a perspective view of the heart stabilizer device, with the stabilizing assembly shown in a folded configuration and being inserted into the port device of the invention.
Figure 23:
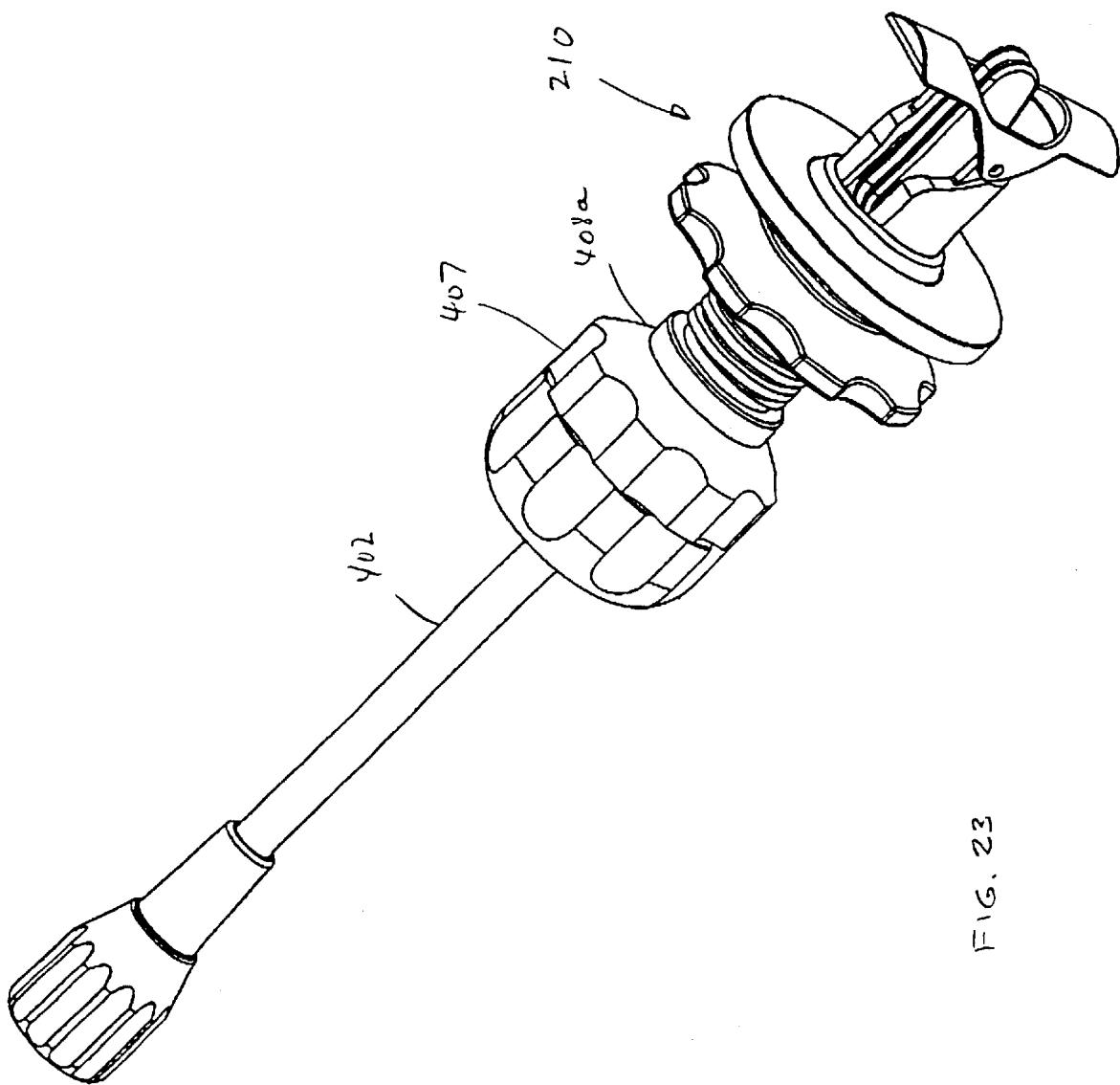
FIG. 23 is a perspective view of the heart stabilizer device, with the stabilizing assembly shown in a folded configuration and being inserted into the port device of the invention and also with a shaft lock being coupled to the port device.
Figure 24:
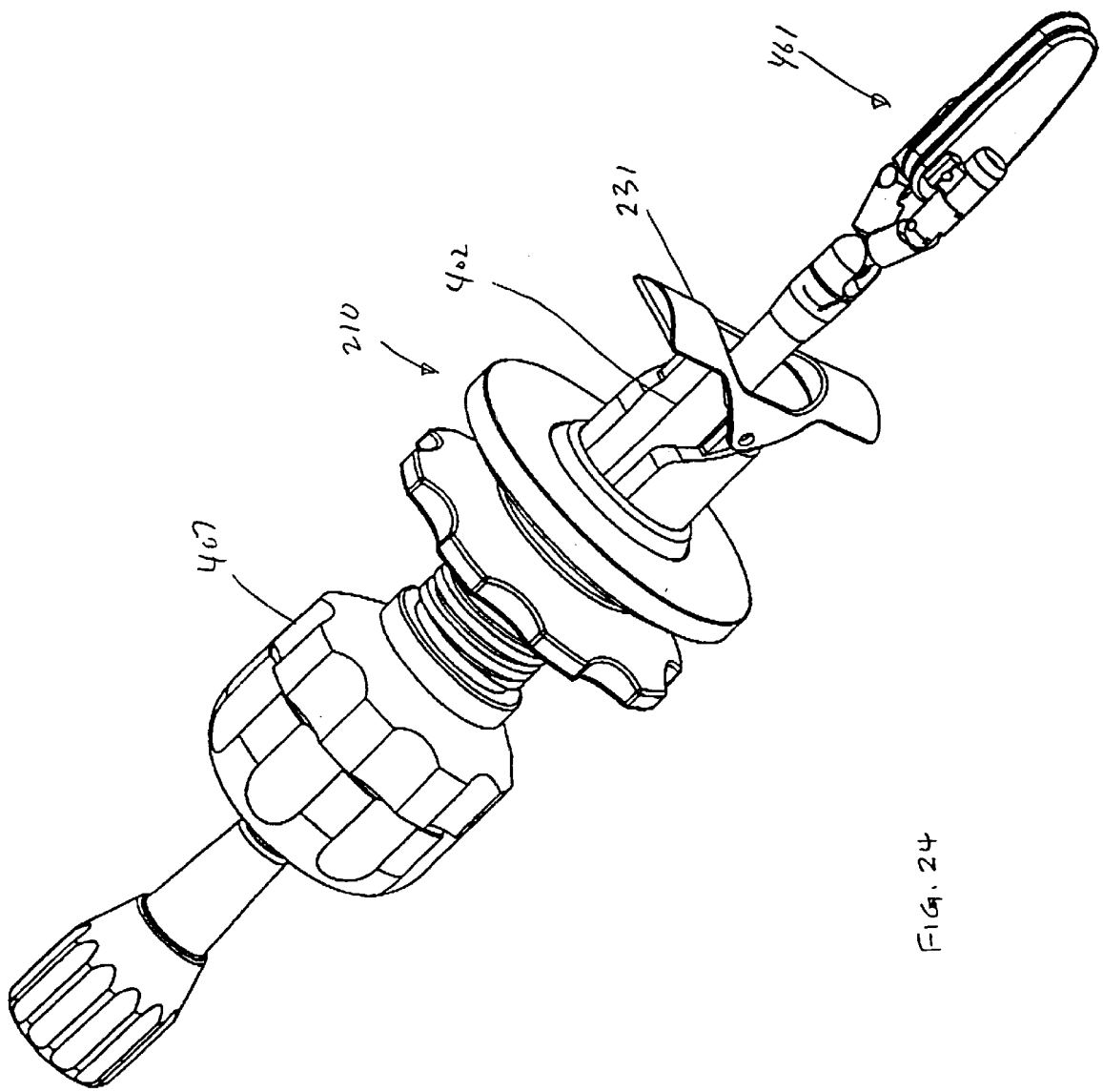
FIG. 24 is a perspective view of the heart stabilizer device, with the stabilizing assembly shown in a folded configuration and being extended through the port device of the invention.

The stabilizing assembly 461 is inserted into a port 210 (FIG. 22) which is mounted in a chest wall of a patient's body (not shown). The shaft lock 407, loosely provided about the shaft 402, is slid along the shaft 402 toward the port, and the port connector 408a of the shaft lock is then coupled to the port (FIG. 23). The shaft 402 is then moved through the shaft lock 407 until the stabilizing assembly 461 is moved beyond the swivel 231 of the port 210 to a location within the chest cavity permitting expansion of the stabilizing assembly 461 (FIG. 24). The shaft lock 407 is then tightened to retain the shaft 402 at the selected location relative to the port 210.

Figure 25:
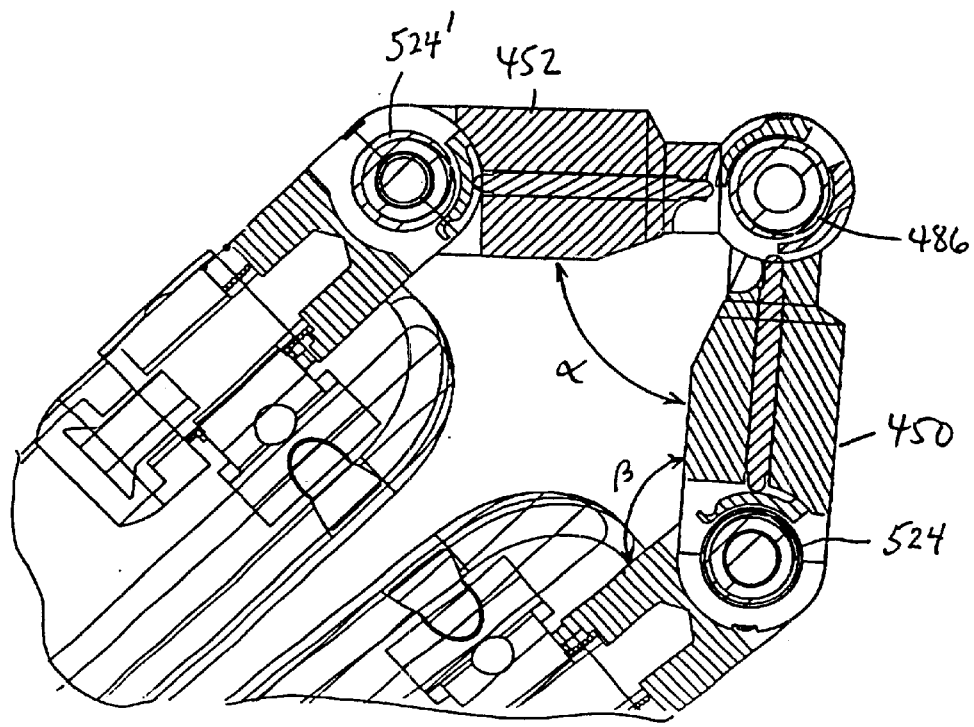
FIG. 25 is a partial longitudinal section view of the stabilizing assembly in a partially open first configuration.
Figure 26:
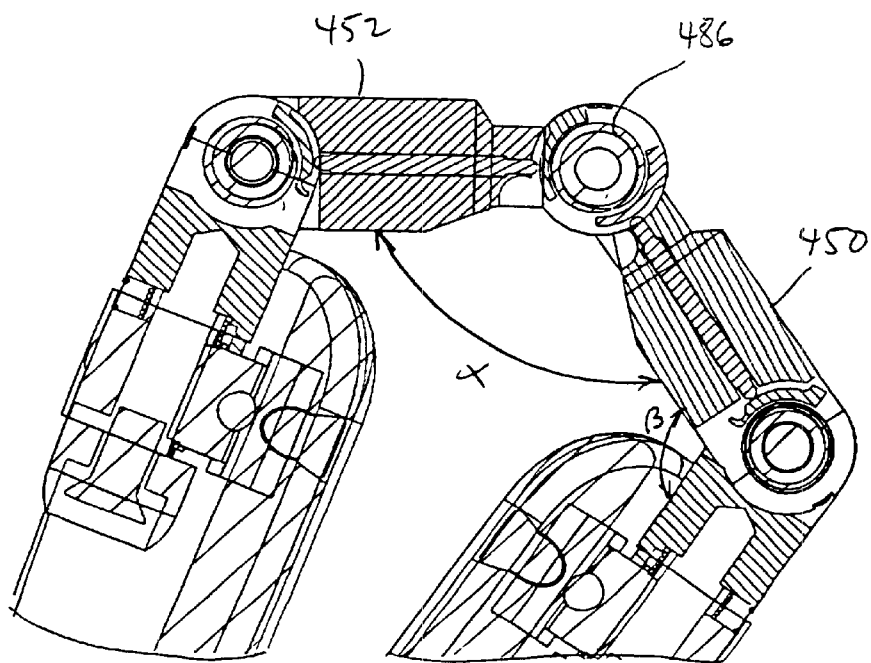
FIG. 26 is a partial longitudinal section view of the stabilizing assembly in a partially open second configuration more open that the first configuration.
Figure 27:
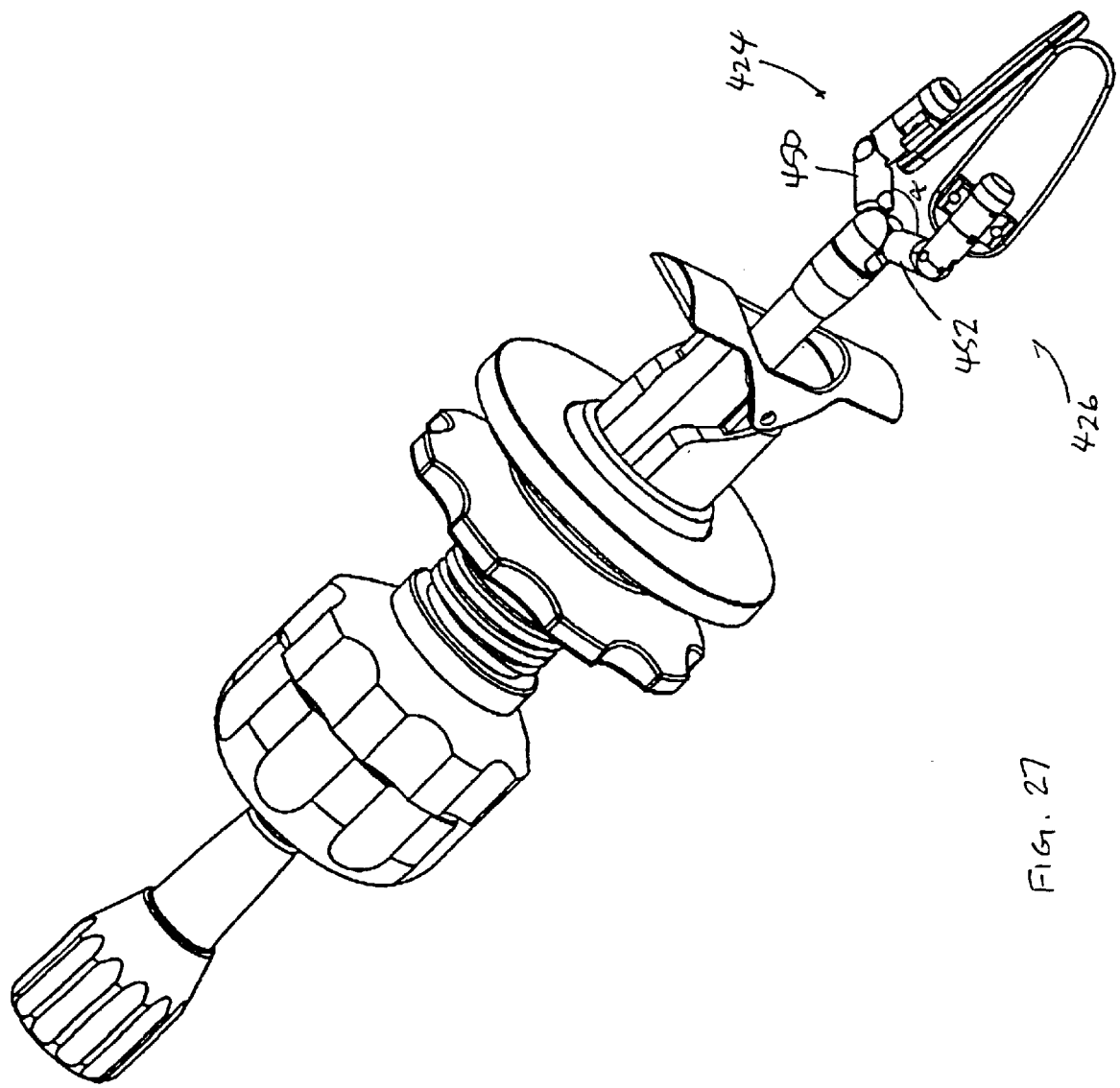
FIG. 27 is a perspective view of the heart stabilizer device, with the stabilizing assembly shown extended through the port device of the invention and in the second configuration.
Figure 28:
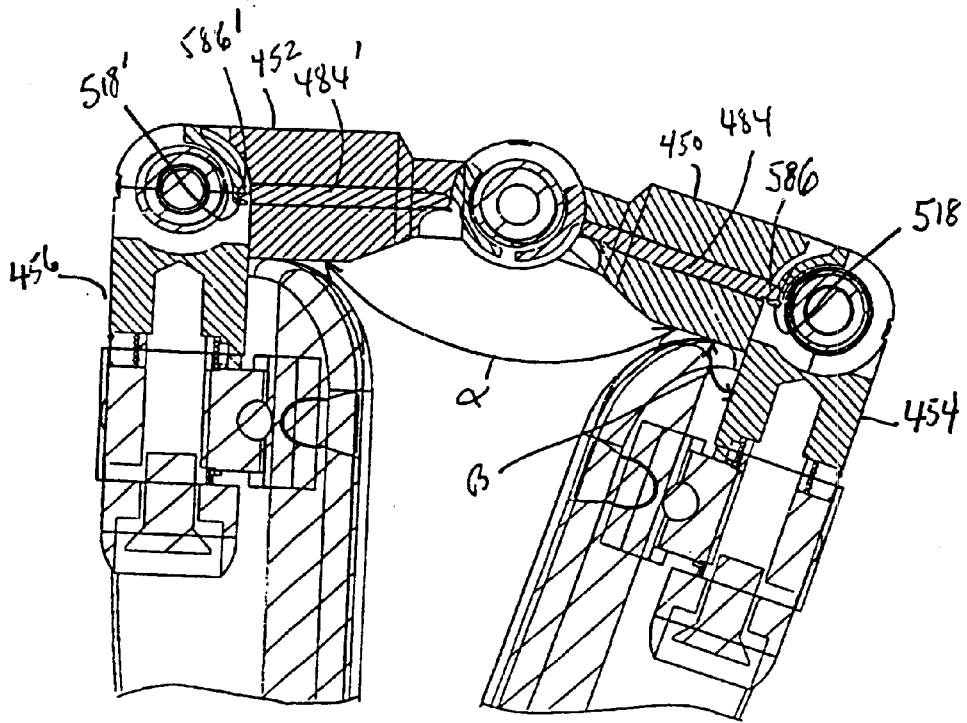
FIG. 28 is a partial longitudinal section view of the stabilizing assembly in a third configuration more open that the second configuration and in which the lock pins engage the lower arm cam locks.
Figure 29:
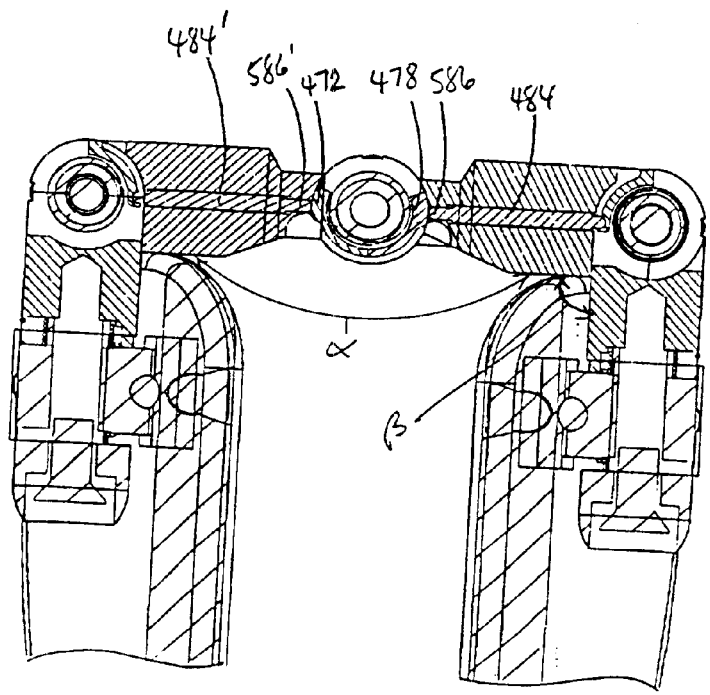
FIG. 29 is a partial longitudinal section view of the stabilizing assembly in a fully open fourth configuration in which the lower arms are locked relative to the upper arms.
Figure 30:
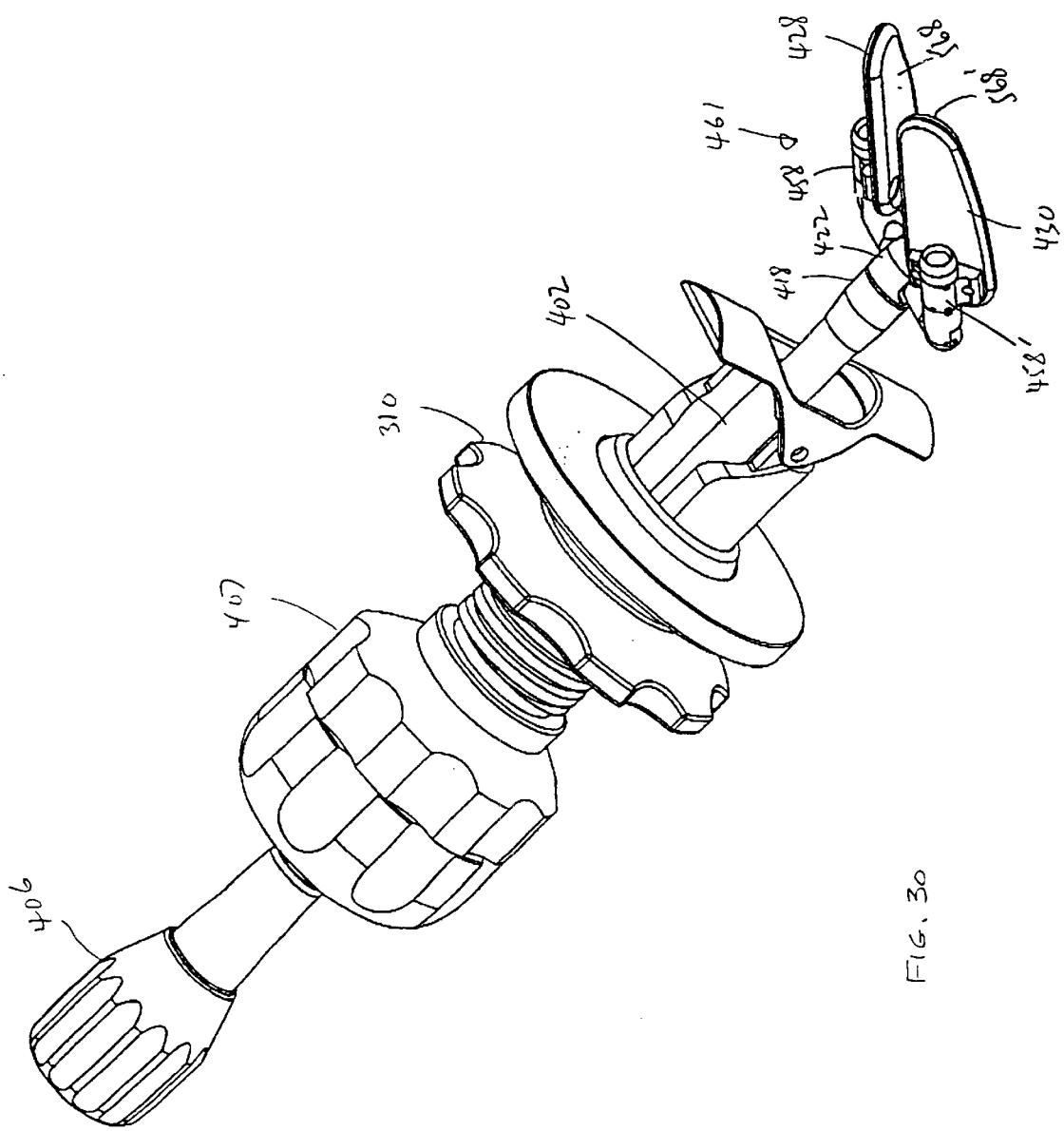
FIG. 30 is a perspective view of the heart stabilizer device, with the stabilizing assembly shown extended through the port device of the invention and in the fully open fourth configuration.

The knob 407 of the handle 406 is then operated to release the socket 422 from compression by the collar 418, thereby permitting movement of the articulating arms 424, 426 in accord with the forces of the springs and lock pins in the arms. More particularly, referring to FIGS. 20 and 25 through 27, when the socket is released, shoulder spring 487 operates to move the upper arms 450, 452 from a closed position (α equals approximately 47° in FIG. 20) toward a more open position (α equals approximately 87° in FIG. 25, and α equals approximately 126° in FIG. 26 and 27). In addition, elbow springs 524, 524' operate to bend the lower arms 454, 456 relative to the upper arms 450, 452 toward a smaller relative angle β. In FIG. 20, β is approximately 156°; in FIG. 25, β is approximately 135°; and in FIG. 26, β is approximately 111°. Referring to FIG. 28, when α is approximately 163°, β is substantially 90°, and the distal ends 586, 586' of the lock pins 484, 484' in the upper arms 450, 452 engage the cam locks 518, 518' of the elbows 510, 510' of the lower arms 454, 456. Then, as shown in FIG. 29, when the angle α is substantially 180°, the lock pins 484, 484' are engaged by the cams 472, 478 on the upper arms to lock the upper and lower arms at an angle β of 90°. It is noted that β is dependent on α only in that as α increases, so does β as a result of the springs in the elbow joints. The only fixed relationship between α and β are when the arms are fully folded, or fully deployed. It will be appreciated that this above described deployment and arm locking is automatic after the socket 436 is released from the collar 418. After deployment, the handle 406 may be operated to cause the collar to again clamp on the socket to prevent any relative movement of the upper arms which may otherwise potentially destabilize the stabilizer assembly 461.

Once the upper and lower arms are locked relative to each other, the shaft 402 (FIG. 16) may be unlocked from the shaft lock 407 and longitudinally moved such that the contact surfaces 568, 568' of the feet 428, 430 contact the heart wall. The feet are adapted to rotate at the wrist mounts 458, 460 relative to the lower arms to contour to the heart wall. The stops 546 on the lower arms (FIG. 19) preferably limit rotation of the feet to ninety degrees relative to the orientation shown in FIG. 21. The shaft 402 is again locked within the shaft lock such that the feet apply sufficient pressure against the wall of the heart to effectively immobilize motion of the heart wall between the feet such that the bypass procedure may be performed between the feet.

Furthermore, after the port off-pump coronary artery bypass procedure, when it is desired to withdraw the heart stabilizer through the port, the handle 406 may be operated to unlock the stabilizer assembly 461. The shaft of the stabilizer is then released from the shaft lock and/or the port connector of the shaft lock is released from the port, and then the stabilizer assembly is forced proximally. When the upper arms contact the port, the upper arms are forced to fold in a reverse operation to deployment, i.e., to a smaller angle α and release the lock pins from the cams and cam locks. As the upper arms fold about the shoulder, the contact surfaces of the feet contact each other and rotate such that the contact surfaces are substantially coplanar. This, in turn, causes the lower arms to rotate about the elbow such that an increased angle β is provided between the upper and lower arms permitting withdrawal of the assembly through the port.

According to various embodiments of the heart stabilizers the feet of the stabilizer may be further adapted to facilitate immobilization of the heart wall between the feet. In addition to compressive forces, the feet may be adapted to apply suction, chemical agents, electrical current, or thermal cooling to enhance the heart wall immobilization.

In addition, while various means for opening, and limiting the extent of opening, of the stabilizing assemblies of the heart stabilizer have been disclosed, it will be appreciated that other means providing the same function may be used. Moreover, while particular preferred angles between the elements of the stabilizing assemblies have been disclosed, it will be appreciated that other preferred angles can be used, with angles other than those disclosed causing engagement of the cams to lock the arms.

Figures 35, 36:
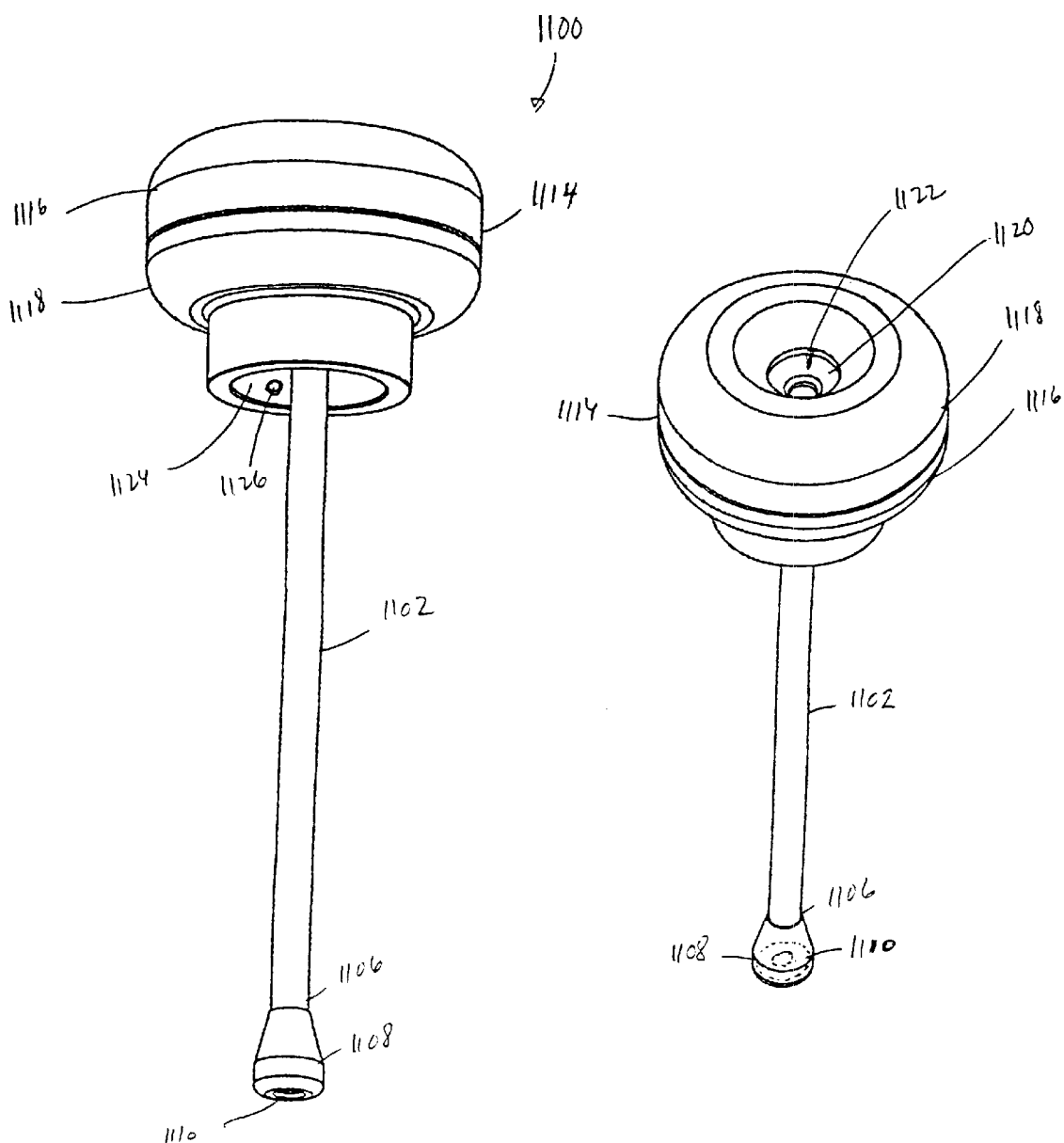
FIG. 35 is a lower perspective view of a first embodiment of an instrument stabilizer according to the invention.
FIG. 36 is a top perspective view of the first embodiment of the instrument stabilizer.
Figure 37:
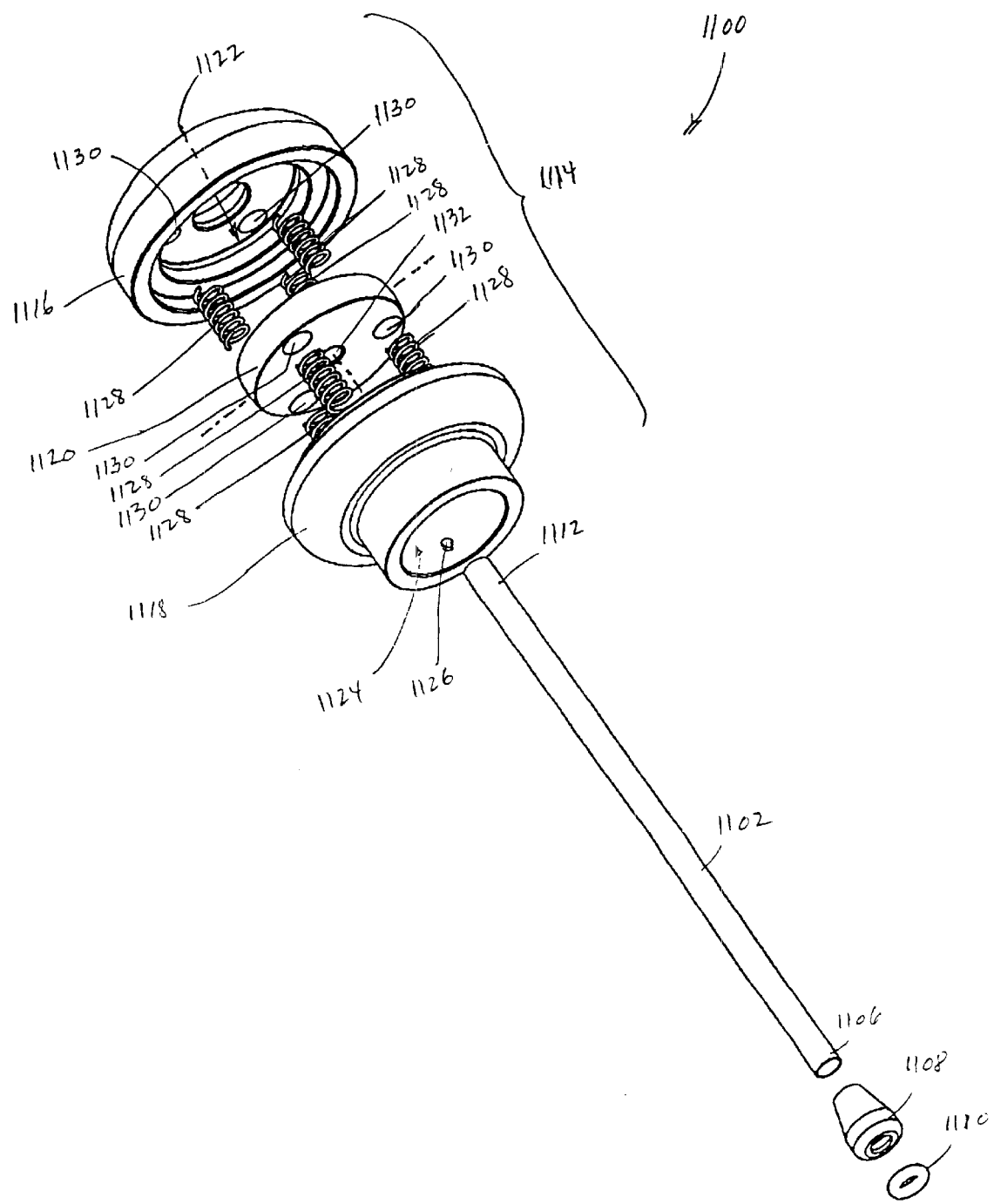
FIG. 37 is an exploded view of the first embodiment of the instrument stabilizer.

Referring now to FIGS. 35 through 37, a first embodiment of an instrument stabilizer 1100 is shown. The instrument stabilizer 1100 includes a cannula 1102 through which an endoscopic instrument, e.g., a laparoscopic instrument, can extend. Endoscopic instruments, in general, are instruments which are extendable through a scope, or operated in conjunction with a scope, used to view the inside of a body cavity. The distal end 1106 of the cannula 1102 is provided with a tapered ferrule 1108 including an O-ring 1110 adapted in size to contact an endoscopic instrument extending therethrough. The proximal end 1112 of the cannula 1102 is coupled to a proximal housing 1114 of the instrument stabilizer.

The proximal housing 1114 includes an upper shell 1116 and a lower shell 1118, and a disc 1120 stabilized therebetween. The upper shell 1116 includes a central opening 1122 through which an endoscopic instrument may extend. The lower shell includes a relatively larger central opening 1124, and optionally includes a mating structure, e.g., a nub 1126, adapted to couple the housing 1114 to a mating structure on one of the above described ports, or another port. The disc 1120 is preferably stabilized with preferably three equally-spaced springs 1128 provided on either side of the disc. To maintain the springs 1128 in their relative positions, each side of the disc and the corresponding interior surfaces of the upper and lower shells include recesses 1130 into which the ends of the springs are provided. The upper and lower shells 1116, 1118 are then coupled together about the disc 1120, e.g., via sonic welding, a threaded coupling, or a plurality of fasteners such as screws. The disc 1120 includes a central opening 1132 in which the proximal end 1112 of the cannula 1102 is fixed, e.g., by interference fit or gluing. Alternatively, the cannula 1102 may be snugly fit within the central opening 1132 and permitted to move longitudinally therein to adjust the extension of the distal end 1106 of the cannula relative to the housing 1114.

Turning now to FIGS. 38 and 39, the instrument stabilizer 1100 may be inserted through a port, e.g., port 210, provided in the body of a patient. The distal end 1106 of the cannula 1102 is extended through the port and the mating structure 1126 (FIG. 35) may then be coupled to the mating structure 283 on the port thereby rigidly fixing the instrument stabilizer and the port together (FIG. 39). An endoscopic instrument 1138 may then be inserted through the opening in the upper shell and through the cannula. As the endoscopic instrument 1138 exits the distal end of the cannula 1102, the instrument contacts the O-ring 1110 thereby creating an interference between-the instrument and the O-ring such that a slight resistance to movement of the endoscopic instrument is provided. The spring-stabilized disc 1120, in conjunction with the body tissue, operates to stabilize lateral movement of the endoscopic instrument 1138, while the O-ring 1110 operates to stabilize longitudinal movement of the instrument 1138. As a result, slight forces, e.g., hand tremors, to which the endoscopic instrument is subject are damped. Moreover, as the contact between the O-ring and the instrument is preferably located at the distal end of the cannula, an effective fulcrum for the instrument is provided relatively close to the surgical site, facilitating direction of the instrument and reducing muscle fatigue.

Referring now to FIGS. 40 and 41, a second embodiment of an instrument stabilizer 1200 according to the invention is shown. The instrument stabilizer 1200 includes a cannula 1202 and a housing 1214 having a stabilized disc 1220, as described with respect to the first embodiment. The cannula 1202 is preferably interference fit within an opening in the disc 1220 such that the cannula may be slid relative thereto, yet maintains its relative position unless subject to a sufficient relative longitudinal force. The proximal end 1212 of the cannula is provided with a ferrule 1240. In addition, the distal end 1206 of the cannula, rather than being provided with a ferrule and grommet (as in the first embodiment), is provided with a taper. The distal end 1206 may be tapered by providing one or more slits 1242 in the distal end and compressing the end about the slit or slits. The taper is sufficient to result in close contact between the cannula and an instrument extending through the cannula.

Referring to FIG. 40, in accord with one preferred aspect of the second embodiment, a trocar 1250 may be positioned within the stabilizer 1200 such that a sharp, boring tip 1252 of the trocar extends out the distal end of the cannula. Then, when it is desired to use the instrument stabilizer, the trocar tip and stabilizer are punctured through the tissue of the patient, and the trocar is then removed leaving the stabilizer in place. This permits quick and easy insertion of the stabilizer, creates only a relatively small entry hole, and does not necessitate the use of a port. As an alternative to a sharp tipped trocar, the trocar may include a blunt cautery tip, which permits cautery current to be applied to cut through the chest wall, but is sufficiently blunt to be relatively atraumatic when cautery current is not applied.

Referring to FIGS. 40 and 41, in accord with another preferred aspect of the second embodiment, a flange 1244 is provided about the circumference of the housing 1214. The flange includes a plurality of preferably evenly spaced-apart suture holes 1246. The suture holes 1246 provide locations at which the instrument stabilizer may be sutured directly to the patient. Other means for coupling the instrument stabilizer directly to the patient may also be used. For example, the lower surface 1219 of the lower shell 1218 is preferably convex and may be provided with an adhesive capable of temporarily adhering the instrument stabilizer to the skin of the patient. As yet another example, the lower shell 1218 may be adapted to apply a vacuum against the skin of the patient. Portions of the lower shell 1218 may be selectively coupled to the skin through the use of several suction zones (e.g., four, each extending through a quadrant of the lower shell) which can be individually selected to apply suction. As such, the stabilized disc is then clearly able to operate in conjunction with the damping properties of the flesh of the patient to dampen errant movement applied to an endoscopic instrument extending through the stabilizer 1200.

Figure 42:
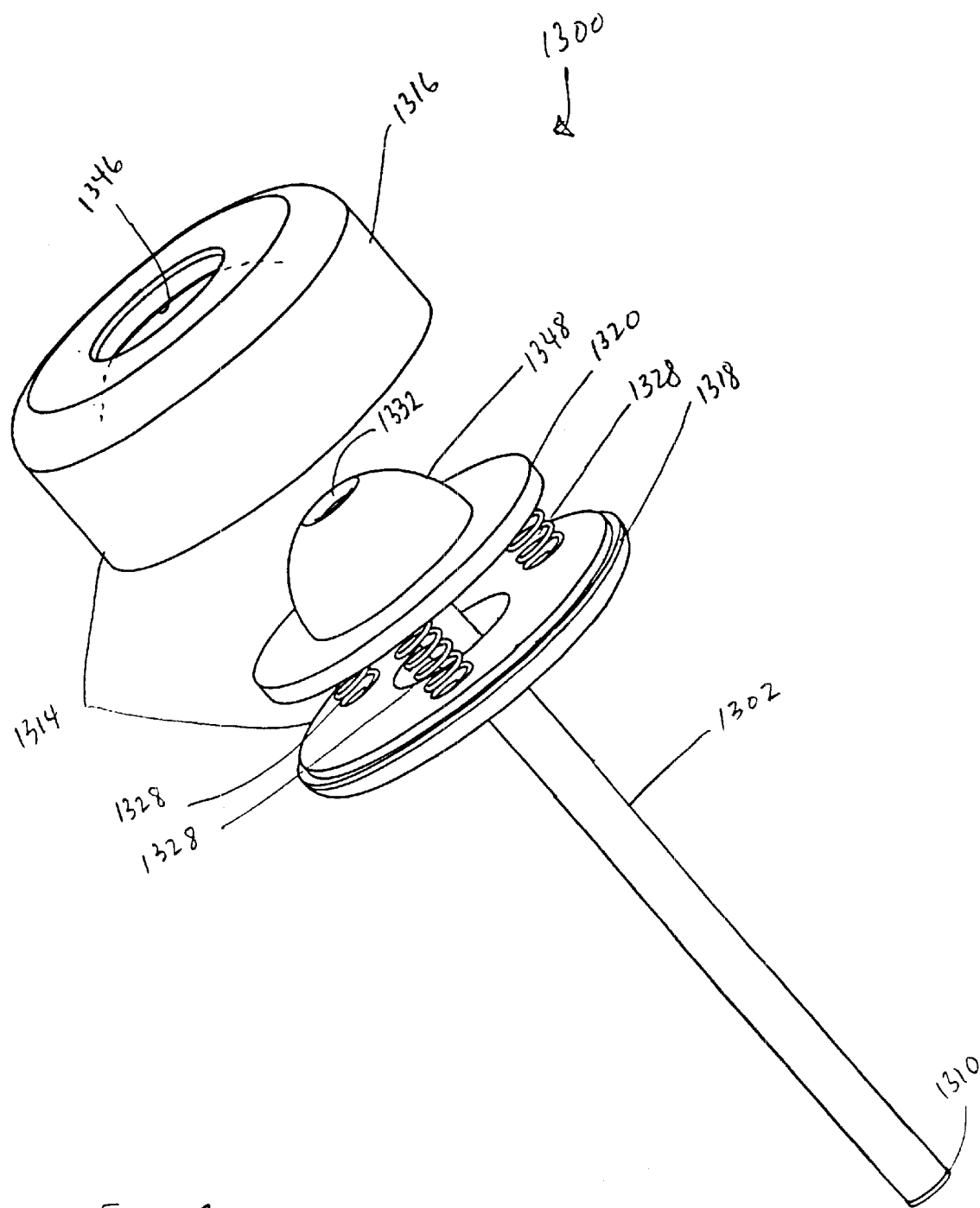
FIG. 42 is an exploded view of a third embodiment of the instrument stabilizer of the invention.

Turning now to FIG. 42, a third embodiment of an instrument stabilizer 1300, substantially similar to the first embodiment, is shown. The third embodiment includes a single set of springs 1328 located between the lower shell 1318 and the lower side of the disc 1320. The upper shell 1316 includes a concave, preferably hemispherical interior surface 1346. The upper side of the disc 1320 is provided with a hemispherical portion 1348. A central opening 1332 extends through the disc 1320 including the hemispherical portion 1348 of the disc. The hemispherical portion 1348 is forced by the springs against the concave interior surface 1346 of the upper shell. The cannula 1302 is provided with a distal bushing 1310 having an opening (not shown) sized to be in close contact with an instrument extending through the cannula. As the instrument is moved relative to the housing 1314, the hemispherical portion 1348 of the disc 1320 articulates relative to the interior surface 1346 of the upper shell 1316. However, movement of the instrument is damped by the springs 1328.

Figure 43:
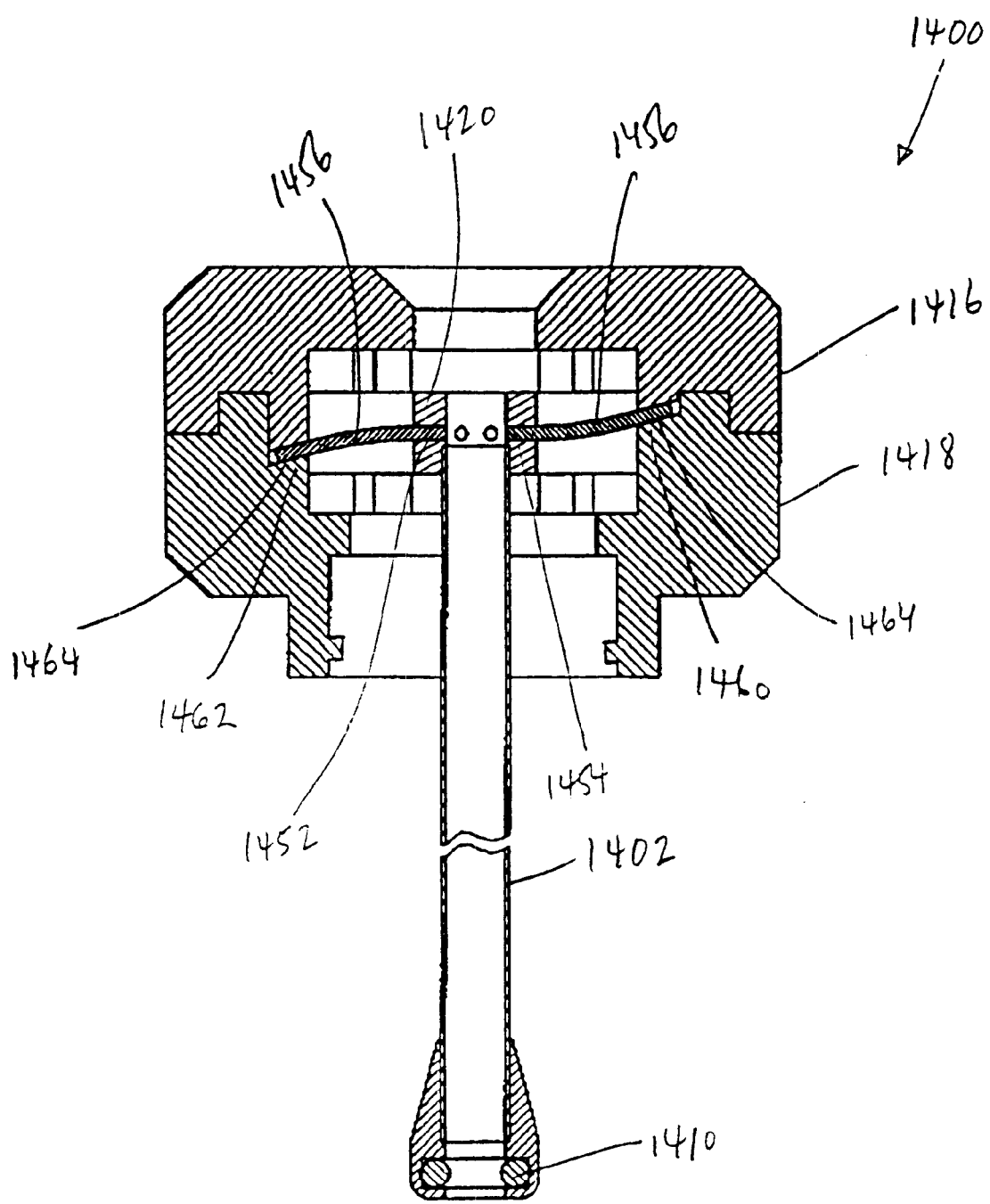
FIG. 43 is a longitudinal section view of a fourth embodiment of the instrument stabilizer of the invention.
Figures 44, 45:
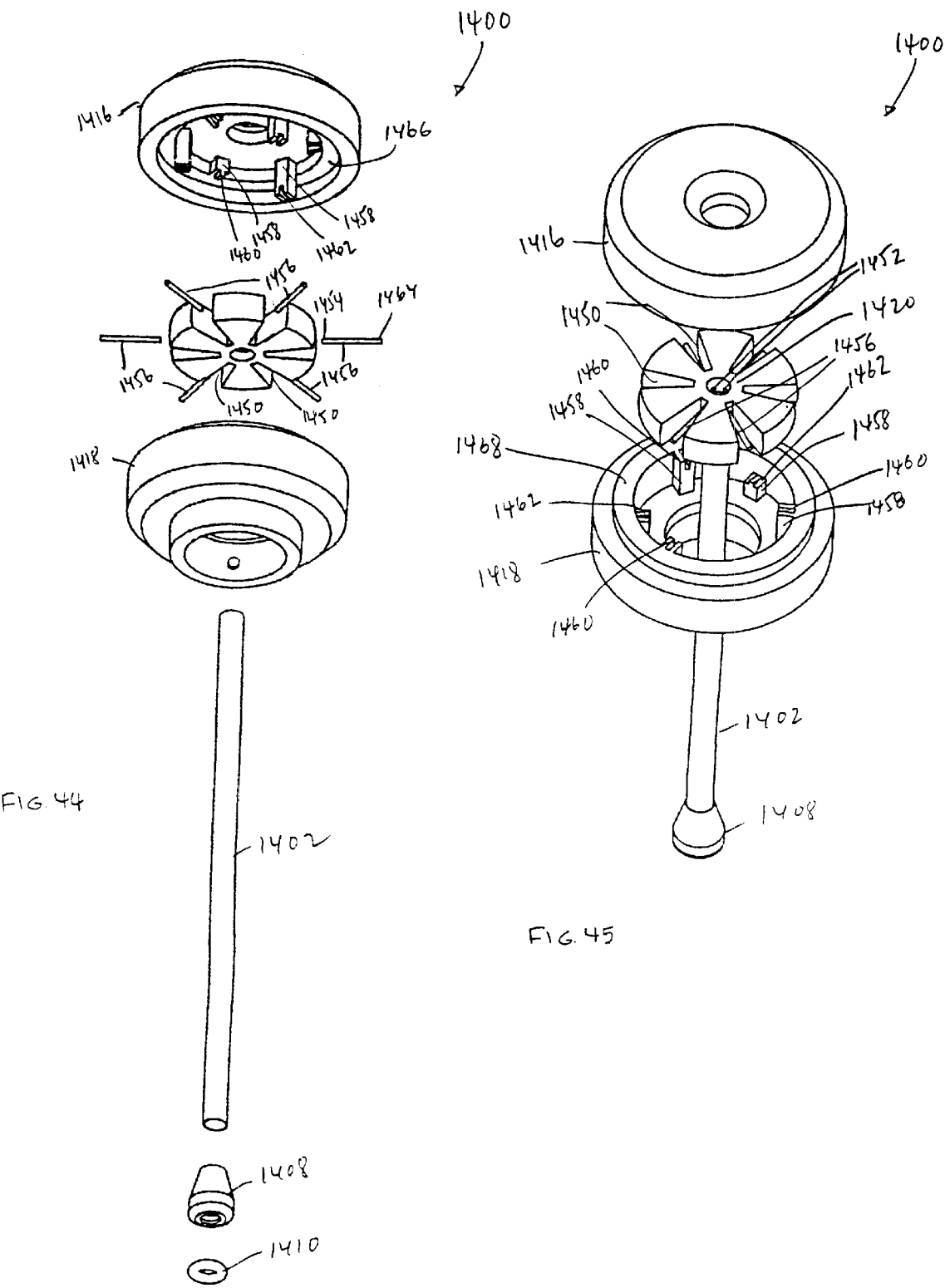
FIG. 44 is an exploded bottom perspective view of the fourth embodiment of the instrument stabilizer of the invention.
FIG. 45 is an exploded top perspective view of the fourth embodiment of the instrument stabilizer of the invention.

Referring now to FIGS. 43 through 45, a fourth embodiment of an instrument stabilizer 1400, substantially similar to the first embodiment, is shown. The instrument stabilizer 1400 includes upper and lower shells 1416, 1418, and a disc 1420 therebetween. The disc 1420 is provided between the upper and lower shells, and includes six radial slots 1450 and a radial bore 1452 centrally located relative to each slot. Each radial bore 1452 is provided with a first end 1454 of a strut 1456. The interior of each shell 1416, 1418 includes six circumferentially positioned, equally spaced apart strut mounts 1458. The strut mounts 1458 are provided with alternating upper and lower strut purchases 1460, 1462, angled downward and upward, respectively (FIG. 43), on which to receive a second end 1464 of a respective strut 1456. The upper shell 1416 includes a circular channel 1466, and the lower shell 1418 includes a circular ridge 1468 sized to fit within the channel 1466. The upper and lower shells 1416, 1418 are sandwiched about the disc 1420 such that second end 1464 of the struts 1456 are received by the respective strut mounts 1458 of the upper and lower shells, and such that the ridge 1468 fits within the channel 1466. The shells 1416, 1418 are then assembled together and sealed to each other, e.g., via sonic welding. With the shells assembled, alternating struts 1456 are bent in upward and downward configurations. Together the struts provide a stabilizing force to the disc. The cannula 1402 is coupled within the disc 1420, and movement of an endoscopic instrument through an O-ring 1410 in a ferrule 1408 of the cannula 1402, is thereby damped.

Figure 46:
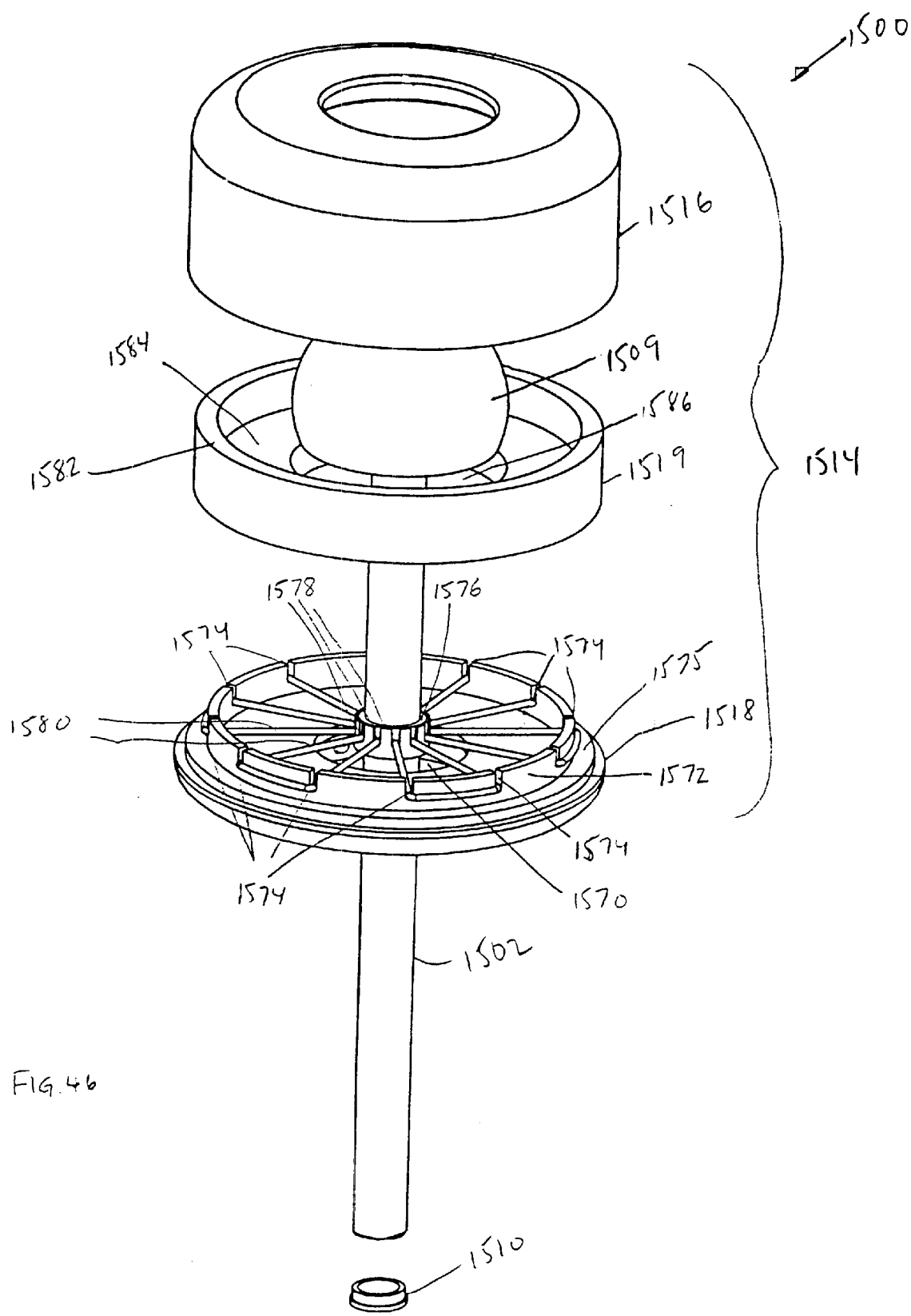
FIG. 46 is an exploded perspective view of a fifth embodiment of an instrument stabilizer of the invention.

Referring now to FIG. 46, a fifth embodiment of an instrument stabilizer 1500 is provided. The instrument stabilizer 1500 includes a cannula 1502 coupled to a housing 1514. The cannula 1502 is provided with a proximal hemispherical head 1509 providing an opening into the cannula, and a distal grommet 1510 sized to be in close contact with an endoscopic instrument extending through the cannula. The housing 1514 includes a lower platform 1518, an upper cap 1516, and a central ring 1519 therebetween. The upper cap 1516 includes a concave interior surface (not shown) on which the hemispherical head 1509 can articulate, and an interior lip (not shown). The lower platform 1518 includes a central opening 1570, a peripheral circular ridge 1572 provided with a plurality of spaced apart slots 1574, and an outer-lip 1575. A collar 1576 is rigidly coupled about a portion of the cannula 1502, and positioned within the ridge 1572 of the platform 1518. The collar 1576 includes a plurality of slots 1578 corresponding to the slots 1574 on the ridge 1572. One or more elastic or resilient band or bands 1580 extend between and within the slots 1574 and 1578 to stabilize the collar 1576 relative to the opening 1570 of the platform 1518. The central ring 1519 includes an outer wall 1582 and a plate portion 1584 with a central opening 1586. When the upper cap 1516 is joined with the platform 1518, the outer wall 1582 is held between the interior lip of the upper cap 1516 and the outer lip 1575 of the platform 1518. The plate portion 1584 operates to prevent disengagement of the bands 1580 from the slots 1574, 1578 when the housing 1514 is assembled and the cannula 1502 is moved relative to the housing. When an instrument is positioned through the cannula 1502 and in contact with the grommet 1510, movement of the instrument is damped and stabilized by the close fit arrangement of the grommet 1510 and the forces of the bands 1580 on the collar 1576 and cannula 1502.

Figure 46A:
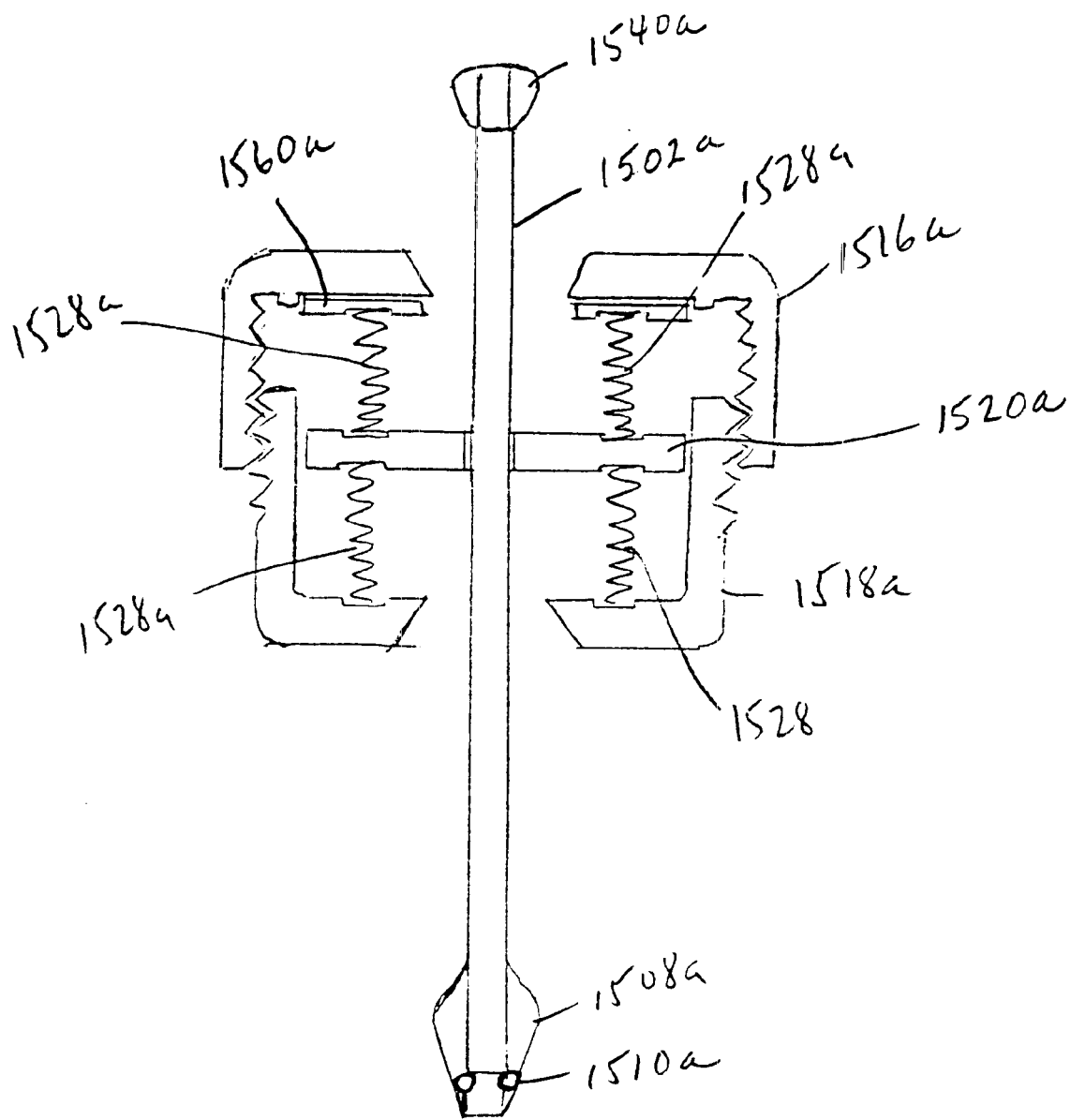
FIG. 46a is a longitudinal section view of a sixth embodiment of the instrument stabilizer of the invention.

Referring now to FIG. 46a, a sixth embodiment of an instrument stabilizer 1500a is shown. The instrument stabilizer 1500a includes a cannula 1502a interference fit in a disc 1520a, as described in the second embodiment. The proximal end 1512a of the cannula 1502a is provided with a ferrule 1540a, and the distal end 1506a is provided with a ferrule and-grommet, as in the first embodiment. Upper and lower shells 1516a, 1518a. in a threaded engagement surround the disc 1520a. A plate 1560a is provided against the interior upper surface of the upper shell and permitted to rotate relative thereagainst. Compression springs 1528a. are provided on each side of the disc, as described with respect to the first embodiment, such that the disc 1520a 'floats' between the upper and lower shells. The shells 1516a and 1518a may be rotated relative to each other such that the shells the springs are further compressed (e.g., via clockwise rotation) and reduced in compression (e.g., via counterclockwise rotation), thereby controllably altering the stabilizing force upon the cannula. Other mechanisms to alter the amount of force on the cannula can also be used.

Figure 46B:
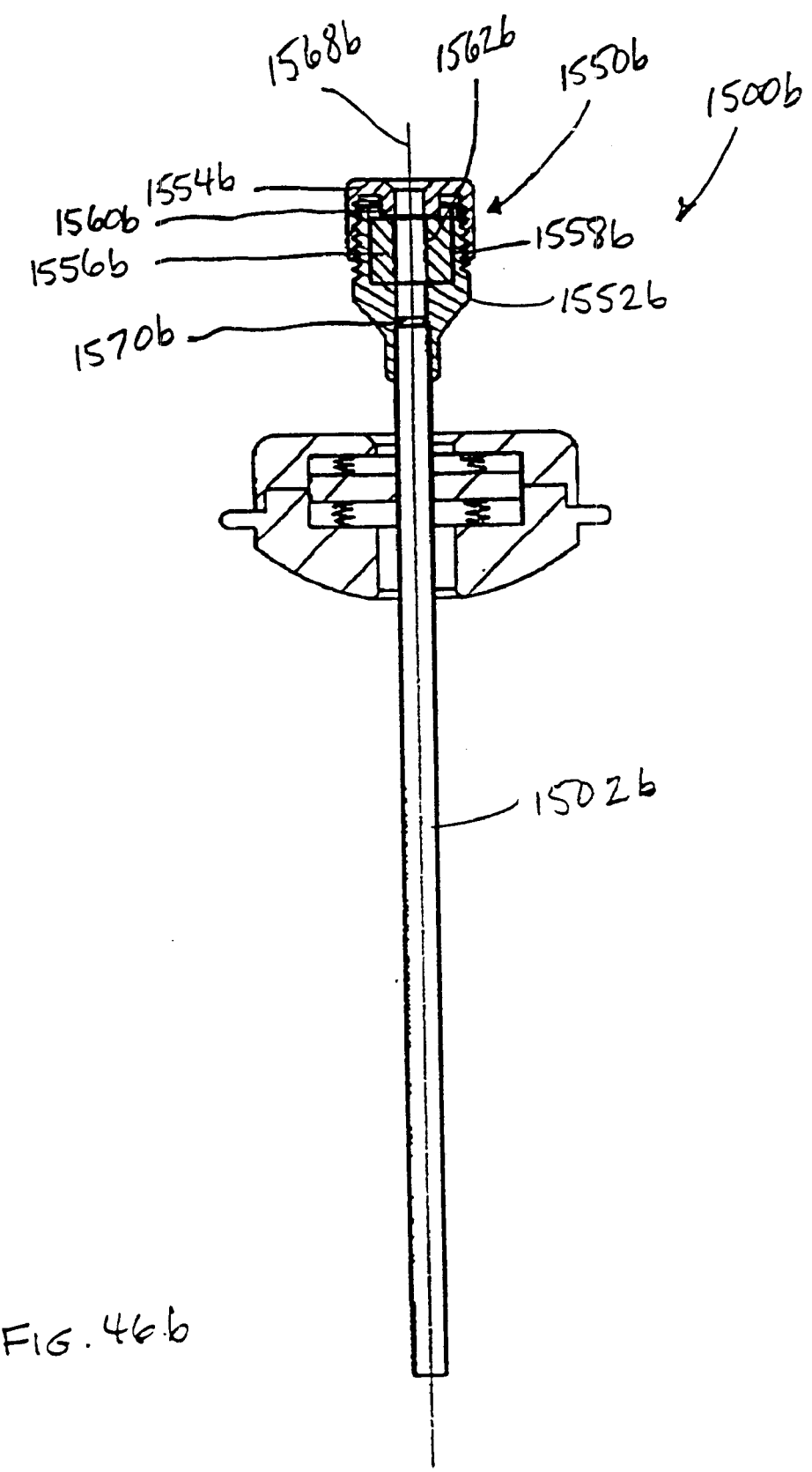
FIG. 46b is a longitudinal section of a seventh embodiment of the instrument stabilizer of the invention.

Furthermore, in any of the above embodiments of an instrument stabilizer, the bushing may be adjusted to affect the amount of friction applied to the instrument extending therethrough. For example, as shown in FIG. 46b, a bushing assembly 1550b may be provided at the proximal end of the instrument stabilizer 1500b. Positioning the bushing assembly 1550b at the proximal end of the stabilizer 1500b permits manipulation of the bushing assembly while the stabilizer is inserted into a human body. The bushing assembly 1550b includes a body 1552b which is rigidly coupled to the cannula 1502b, a cap 1554b which is thread onto the body 1552b, and an elastomeric bushing 1556b in a cavity 1558b of the body. The bushing 1556b seats snugly within the cavity 1558b. Threadably tightening the cap 1554b on the body 1552b about the bushing causes a center portion 1560b of the cap to compress the bushing. This results in the diameter of the open center 1562b of the bushing 1556b decreasing and tightening about an instrument extending through the cannula.

In addition, still referring to FIG. 46b, in any of the above embodiments, the pathway 1568b for the endoscopic instrument may optionally be provided with a valve 1570b to permit the instrument stabilizer to be used for surgical procedures requiring insufflation of the body cavity in which the instrument stabilizer is inserted. The valve 1570b may be provided within the cannula 1502b or at a location proximal or distal of the cannula. In FIG. 46b, the valve is located within the bushing assembly 1550b. When the valve 1570b is in a closed position, fluid is substantially prevented from passing through the cannula. Preferably, insertion of an endoscopic instrument through into the cannula and against the valve automatically opens the valve such that the endoscopic instrument may be moved through the cannula.

Figure 47:
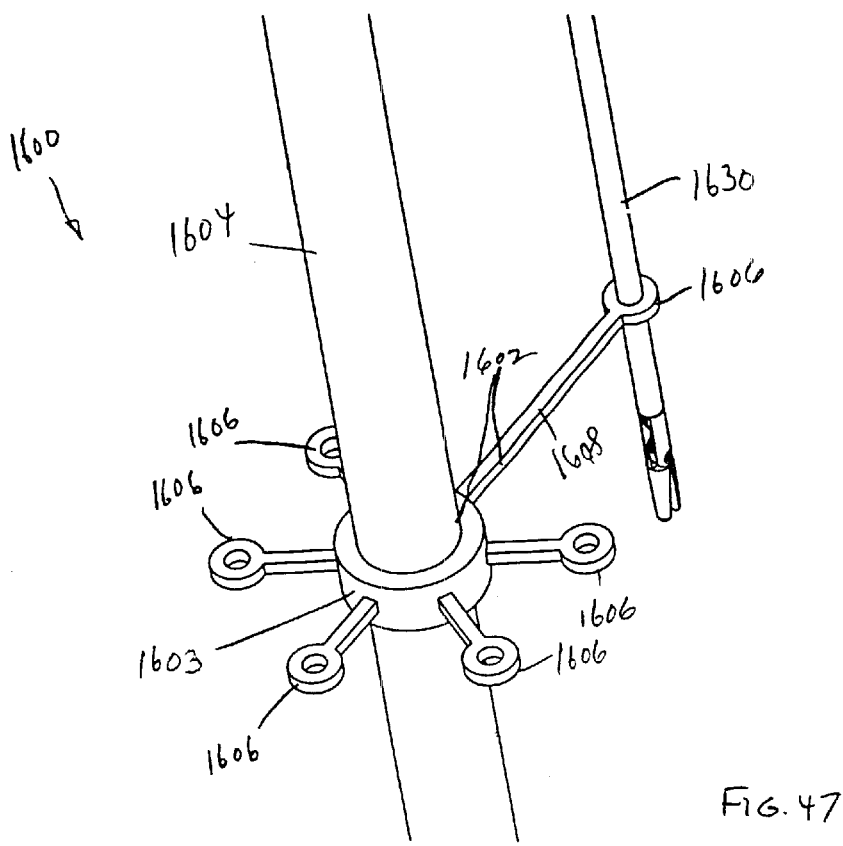
FIG. 47 is a perspective view of an eighth embodiment of the instrument stabilizer of the invention.
Figure 48:
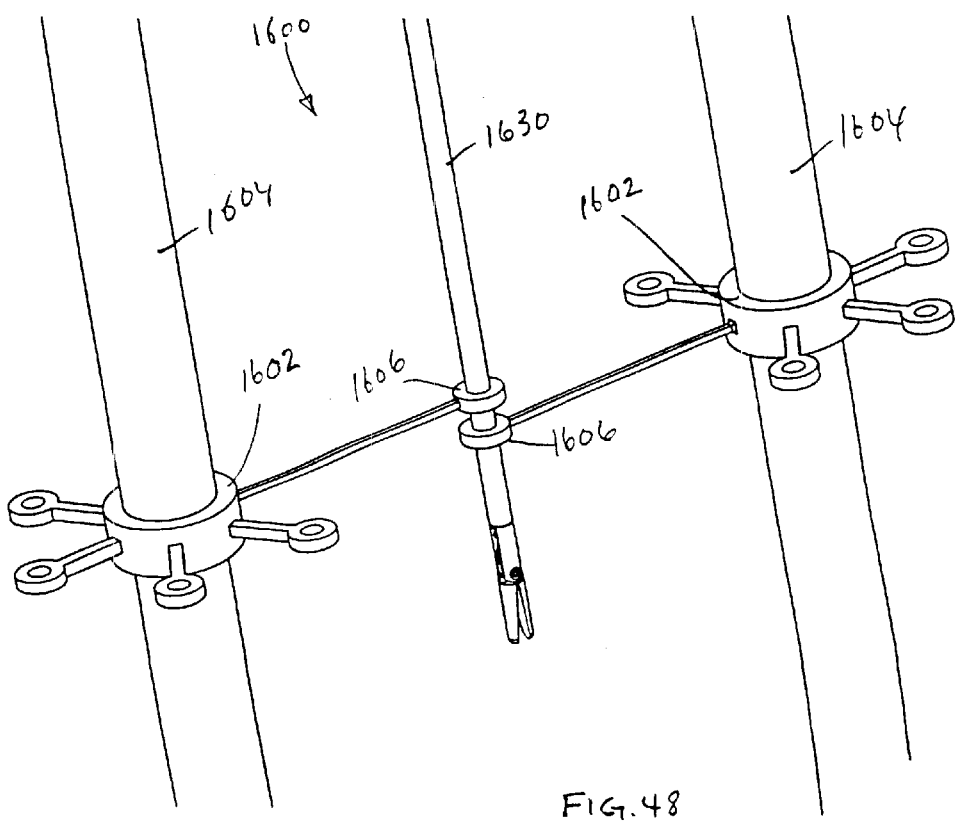
FIG. 48 is a perspective view of a ninth embodiment of the instrument stabilizer of the invention.

Turning now to FIG. 47, an eighth embodiment of an instrument stabilizer 1600 is shown. The instrument stabilizer 1600 includes an instrument coupler 1602 and a preferably stable shaft 1604. The instrument coupler 1602 is preferably elastic and preferably includes a central collar 1603 and plurality of rings 1606 or other instrument gripping means, e.g., ties, collars, tubes, clamps, etc., coupled via an elastic tether 1608 to the preferably ring-shaped shaft collar 1603. The shaft 1604 may be dedicated to the instrument stabilizer, or optionally may be a stabilized shaft of another instrument, e.g., the above described heart stabilizer or another instrument which is substantially stable during a surgical procedure. A surgical instrument 1630 is inserted through one of the rings 1606. Several rings may be occupied by several surgical instruments; the rings being preferably selected based on those which provide best access to the surgical site. The elastic tethers extending from the rings to the shaft collar operate to dampen the unwanted movements to which the surgical instruments are subject. In addition, referring to FIG. 48, instrument coupler 1602 may be used on a plurality of shafts 1604 such that a single instrument 1630 is stabilized by more than one coupler 1602, further damping forces to which the instrument 1630 is subject.

It is intended that the various features of the several embodiments may be utilized in other combinations. Also, while various means for coupling an instrument stabilizer to a patient's body or a port or a shaft (in the case of the sixth embodiment), have been disclosed, it will be appreciated that other suitable means may be used. Furthermore, while in the first through seventh embodiments of the instrument stabilizer, the cannula is coupled to a disc which is stabilized within the housing, plates other than disc-shaped, e.g, triangular, may be used. Moreover, other damping means may be used. For example, a rubber or other resilient-material plate held within the housing can be used. Such a rubber plate is self-damping and does not require any springs, bands, etc. In addition, while various means having been disclosed for stabilizing and damping the forces to which a surgical instrument and a cannula are subject, it will be appreciated that other means may likewise be used. Furthermore, while an O-ring, a grommet, and a tapered cannula have been disclosed for providing a close fit arrangement with a cannula, other close fitting bushings, e.g., a diaphragm or piece of sponge, may be used. In addition, such bushings may be provided anywhere along the length of the cannula. However, if the bushing is provided at the proximal end, it is preferable that a close fit between the instrument and the stabilizer also be provided at the distal end. Moreover, an instrument stabilizer may be provided which includes only one of the stabilized disc and the close fit bushing without the other.

Turning now to FIGS. 49 and 50, a stabilizer swivel 1700 according to the invention is shown. The stabilizer swivel, as described further below, permits an instrument stabilizer, such as stabilizer 1100, to be maintained at an angle relative to a location on the body of a patient. The stabilizer swivel 1700 includes upper and lower complementary wedge elements 1702, 1704, respectively, together preferably defining a cylinder, and a disc 1720.

The upper wedge element 1702 includes: an upper surface 1705 provided with a tubular mating portion 1706 defining an opening 1707 through element 1702, a lower surface 1711 including a circular recess 1708 having a periphery 1709, and three threaded bores 1710 spaced about the opening 1707 and extending into the recessed portion of the upper wedge in a direction preferably normal to the surface 1712 of the recess 1708. The upper surface 1705 and lower surface 1711 are preferably at an approximately 22.5° angle relative to each other. In addition, a locking screw 1714 extends through the upper wedge in a direction preferably normal to the upper surface 1705 of the upper wedge.

The lower wedge 1704 includes: an upper surface 1715, a lower surface 1716, a central opening 1717 which is preferably relatively larger than the opening 1707, and three threaded bores 1718 extending into the lower wedge preferably normal to the upper surface 1715 of the lower wedge and preferably equally spaced apart about the opening 1717. The upper surface 1715 and the lower surface 1716 of the lower wedge element are preferably at an approximately 22.5° relative to each other.

The disc 1720 includes a circumferential bevel 1722 on one side and three holes 1724. The disc 1720 is provided in the recess 1708 between the upper and lower wedges 1702, 1704. Preferably three screws 1726, each having a tapered and substantially flat head 1728, are engaged in the three threaded bores 1718, with the taper of the head of the screws 1726 lying complementary to the bevel 1722 on the disc 1720 such that the screws 1726 surround and retain the disc while still permitting the disc to rotate relative to the lower wedge 1704. A second set of screws 1730 extend up through the holes 1724 of the disc and secure the disc in the recess 1708 of the upper wedge 1702. The disc 1720 and periphery 1709 of the recess together define a track through which the heads 1728 of the screws 1726 may be rotated. As such, the upper and lower wedges are coupled to each other and are also permitted to rotate relative to each other such that the tubular mating portion 1706 may be directed at various angles relative to the central opening 1717 of the lower wedge 1704 (FIGS. 51 and 52), and therefore the surface on which the lower wedge is seated. With the given angles of the surfaces of the upper and lower wedges, the tubular mating portion may be directed between 0° and 45° relative to the opening of the lower wedge. It will be appreciated that by providing other relative angles to the respective upper and lower surfaces, a different range of angles at which the mating portion may be directed is obtained. Other mechanisms permitting relative rotational configurations of the upper and lower wedges may also be used.

Referring to FIG. 52, the central opening 1717 is sized such that even when a maximum angle is provided between the mating portion 1706 and the central opening, the pathway through the mating portion is unobstructed at preferably all locations, as indicated by arrow A. Once a desired relative angle is provided, the locking screw 1714 is tightened in to contact with the lower wedge, thereby causing the upper and lower wedges to be forced apart at one side and resulting in sufficient resistance to rotation at the opposite side. Loosening of the locking screw 1714 again permits relative rotation of the upper and lower wedges 1702, 1704.

Figure 53:
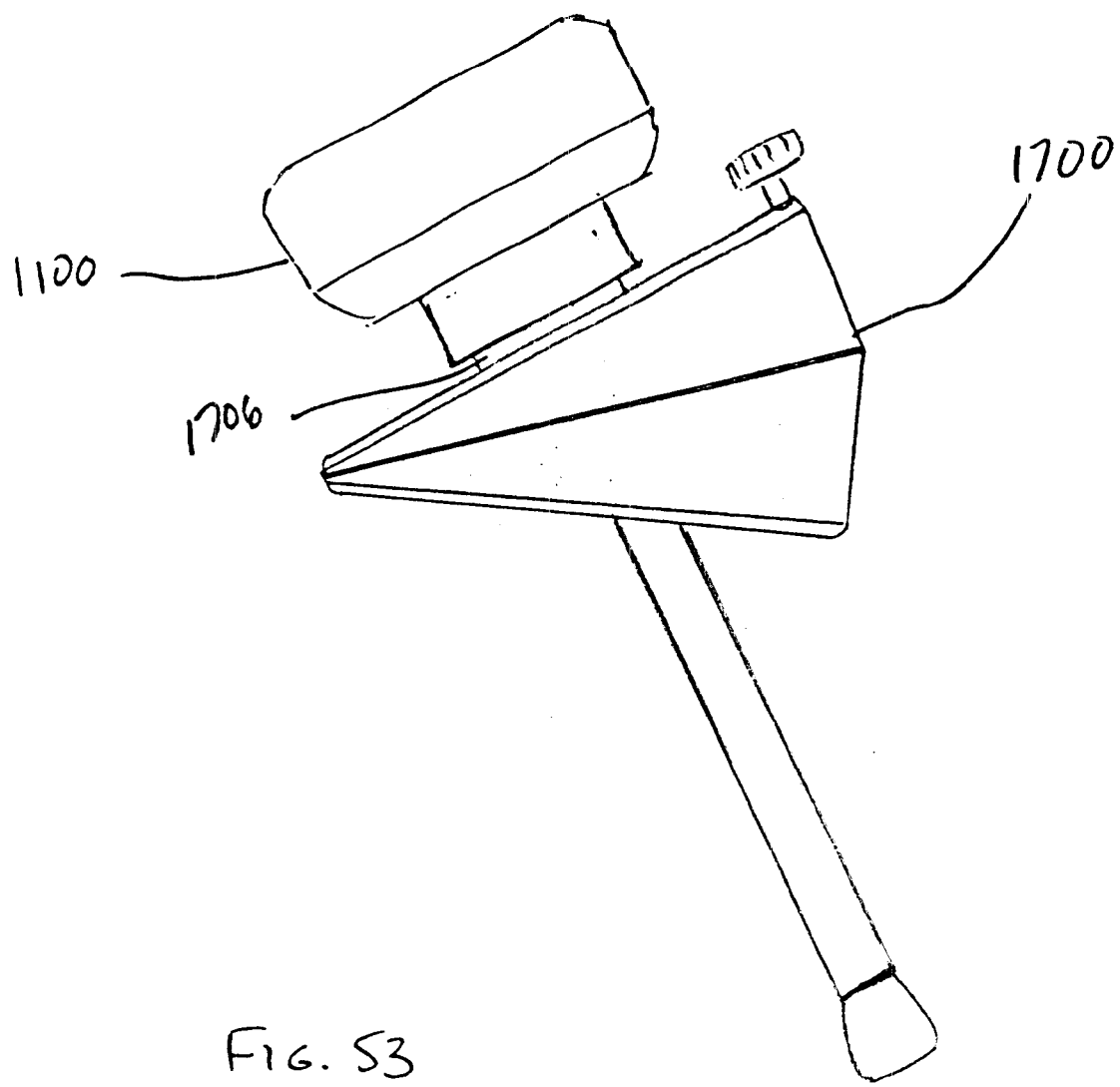
FIG. 53 is a side view of an instrument stabilizer coupled to the stabilizer swivel in the second angular orientation.

Turning now to FIG. 53, an instrument stabilizer, e.g., stabilizer 1100, may be coupled to the stabilizer swivel 1700 at the tubular mating portion 1706. The stabilizer 1100 may then be angled relative to the surface on which the stabilizer swivel is seated, i.e., the patient, to facilitate maintaining the stabilizer, and therefore an instrument extending therethrough, at a desired orientation. Moreover, it will be appreciated that the swivel 1700 can be integrated into an instrument stabilizer such that the two are in a common instrument.

According to a preferred method which utilizes the system, a port device is stably positioned, e.g. clamped, in the chest wall and directed as necessary for operation on the heart wall. A heart stabilizer is coupled to the port, and operated to apply a compressive force against the heart wall surrounding a location of the required bypass such that the location is substantially immobilized. An instrument stabilizer is inserted through a puncture hole in the chest cavity, and the distal tip of the cannula of the stabilizer is located adjacent to the surgical site. A first surgical instrument, e.g., a scalpel or needle holder, is passed through the cannula and operated to perform at least a portion of the procedure. If other surgical instruments are required, the first instrument may be removed and other instruments may be extended therethrough. Alternatively, an instrument stabilizer may be provided for each instrument. Once the bypass procedure is complete, the instruments and instrument stabilizers are removed from the locus of the surgery, and the heart stabilizer is also removed through its port. Then, the clamping forces on the port is loosened and the port is withdrawn from the chest wall. Finally, the incision and puncture holes in which the port and instrument stabilizer were located are closed. This method eliminates the need for many-open heart procedures, as well as the need to stop the heart.

There have been described and illustrated herein several embodiments of a system for performing port off-pump coronary artery bypass surgery and a port device and heart stabilizer therefor. While particular embodiments of the invention have been described, it is not intended that the invention be limited thereto, as it is intended that the invention be as broad in scope as the art will allow and that the specification be read likewise. Therefore, while the elements of the system have been particularly described for use in a port off-pump coronary artery bypass procedure, it will be appreciated that each element may be used alone or in combination for other procedures. In addition, while the port and instrument stabilizer have been described with respect to their use with endoscopic instruments, each may be used with other types of surgical instruments. It will therefore be appreciated by those skilled in the art that yet other modifications could be made to the provided invention without deviating from its spirit and scope as claimed.

What is claimed is:

1. A method of performing a port off-pump beating heart coronary artery bypass surgical procedure through a chest wall, comprising:
   a) inserting a first port device into the chest wall; and
   b) extending a heart stabilizer through said first port device and locking said heart stabilizer to said first port device such that sufficient pressure is applied to a beating heart wall surrounding a location of the required bypass such that the location is substantially immobilized.

2. A method according to claim 1, further comprising:
   c) inserting a second port device into the chest wall; and
   d) extending a surgical instrument through said second port device.

3. A method according to claim 2, further comprising:
   e) prior to extending said surgical instrument through said second port device, extending an instrument stabilizer having a tubular portion through said second port device,
      wherein when said surgical instrument is extended through said second port device, said surgical instrument is also extended through said tubular portion of said instrument stabilizer, said instrument stabilizer adapted to provide a damping force to said surgical instrument to reduce extraneous movement at a distal end of said surgical instrument.

4. A method according to claim 3, further comprising:

f) using said surgical instrument to at least partly perform a coronary artery bypass procedure.

5. A method according to claim 2, further comprising:

e) rigidly fixing at least one of said first port device and said second port device to the chest wall.

6. A method according to claim 5, further comprising:

f) angularly directing at least one of said first port device and said second port device relative to the chest wall.

7. A method according to claim 2, further comprising:

e) angularly directing at least one of said first port device and said second port device relative to the chest wall.

8. A method according to claim 1, further comprising:

c) extending at least a portion of a cannula of an instrument stabilizer through tissue of the patient and into a chest cavity; and d) extending a surgical instrument through said cannula of said instrument stabilizer, wherein said instrument stabilizer is adapted to provide a damping force to said surgical instrument to reduce extraneous movement at a distal end of said surgical instrument.

9. A method according to claim 8, wherein:

said extraneous movement reduced is longitudinal relative to said cannula.

10. A method according to claim 8, wherein:

said extraneous movement reduced is non-parallel relative to said cannula.

11. A method according to claim 8, wherein:

said cannula is provided with a distal boring tip adapted to puncture the tissue of the patient thereby permitting the extension of said at least said portion of said cannula through the tissue.

12. A method according to claim 8, further comprising:

e) using said surgical instrument to at least partly perform a coronary artery bypass procedure.

13. A method according to claim 8, further comprising:

e) coupling said instrument to the patient with sutures or adhesive.

14. A method of performing a port off-pump beating heart coronary artery bypass surgical procedure through a chest wall, comprising:

a) inserting a first port device into the chest wall;

b) clamping the first port device about the chest wall; and c) extending a heart stabilizer through said first port device and locking said heart stabilizer to said first port device such that sufficient pressure is applied to a beating heart wall surrounding a location of the required bypass such that the location is substantially immobilized.

15. A method according to claim 14, further comprising:

d) inserting a second port device into the chest wall; and e) extending a surgical instrument through said second port device.

16. A method according to claim 15, further comprising:

f) prior to extending said surgical instrument through said second port device, extending an instrument stabilizer having a tubular portion through said second port device, wherein when said surgical instrument is extended through said second port device, said surgical instrument is also extended through said tubular portion of said instrument stabilizer, said instrument stabilizer adapted to provide a damping force to said surgical instrument to reduce extraneous movement at a distal end of said surgical instrument.

17. A method according to claim 16, further comprising:

g) using said surgical instrument to at least partly perform a coronary artery bypass procedure.

18. A method according to claim 15, further comprising:

f) angularly directing at least one of said first port device and said second port device relative to the chest wall; and g) fixing said at least one of said first port device and said second port device to the chest wall at a first angle which is oblique relative to a normal of the chest wall at a location of the chest wall at which said at least one of said first port device and said second port device is located.

19. A method according to claim 14, wherein:

said clamping occurs about at least one rib.

20. A method according to claim 14, further comprising:

d) prior to said clamping, angularly directing said first port device relative to the chest wall.

* * * * *